United States Patent
Takeuchi

(10) Patent No.: US 10,556,099 B2
(45) Date of Patent: Feb. 11, 2020

(54) LEVER LOCK MALE CONNECTOR AND MALE CONNECTOR ASSEMBLY

(71) Applicant: JMS CO., LTD., Hiroshima-shi, Hiroshima (JP)

(72) Inventor: Masahiko Takeuchi, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 168 days.

(21) Appl. No.: 15/551,837

(22) PCT Filed: Feb. 17, 2016

(86) PCT No.: PCT/JP2016/054618
§ 371 (c)(1),
(2) Date: Aug. 17, 2017

(87) PCT Pub. No.: WO2016/133139
PCT Pub. Date: Aug. 25, 2016

(65) Prior Publication Data
US 2018/0064923 A1 Mar. 8, 2018

(30) Foreign Application Priority Data

Feb. 18, 2015 (JP) ................................. 2015-030007

(51) Int. Cl.
*A61M 39/10* (2006.01)
*F16L 37/133* (2006.01)

(52) U.S. Cl.
CPC ........ *A61M 39/1011* (2013.01); *F16L 37/133* (2013.01); *A61M 2039/1066* (2013.01)

(58) Field of Classification Search
CPC .......... A61M 39/1011; A61M 39/1088; A61M 39/10; A61M 2039/1066;
(Continued)

(56) References Cited

U.S. PATENT DOCUMENTS 5,362,111 A 11/1994 Harbin
2010/0228231 A1 9/2010 Weigel et al.
(Continued)

FOREIGN PATENT DOCUMENTS

DE 20 2012 101 283 7/2013
JP 7-103222 4/1995
(Continued)

OTHER PUBLICATIONS

Translation of JP-2012-075495A2 (Year: 2012).*
Extended European Search Report issued in corresponding European Patent Application No. 16752525.2, dated Sep. 21, 2018, 8 pages.

*Primary Examiner* — Bhisma Mehta
*Assistant Examiner* — Hamza A Darb
(74) *Attorney, Agent, or Firm* — Hamre, Schuamnn, Mueller & Larson, P.C.

(57) ABSTRACT

A male luer (10) is surrounded by a hood (20). A lever (30) is connected to a base end portion (13) of the male luer via a base (15). The lever includes a locking portion (31) and an operating portion (35). A locking claw (32) protrudes from the locking portion toward the male luer. The locking portion is disposed in a cut-out (23) that is formed in the hood. The lever is elastically pivotable so that when an outer surface of the operating portion is pressed, the locking claw moves away from the male luer. When viewed along a central axis (3a), a connector main body (3) has a major axis (15a) in the direction in which the male luer opposes the lever.

14 Claims, 37 Drawing Sheets

(58) Field of Classification Search
CPC .. A61M 2039/1027; A61M 2039/1072; A61M 39/14; A61M 2039/1016; F16L 37/133; F16L 37/08
See application file for complete search history.

(56) References Cited

U.S. PATENT DOCUMENTS

| | | | |
|---|---|---|---|
| 2013/0079730 A1* | 3/2013 | Mosler | A61M 39/10 604/244 |
| 2013/0317483 A1* | 11/2013 | Reichart | A61M 27/00 604/541 |
| 2015/0008664 A1 | 1/2015 | Tachizaki | |
| 2015/0105753 A1* | 4/2015 | Okiyama | A61M 39/045 604/535 |
| 2015/0297830 A1 | 10/2015 | Okiyama | |

FOREIGN PATENT DOCUMENTS

| | | |
|---|---|---|
| JP | 7-148271 | 6/1995 |
| JP | 2004-000483 | 1/2004 |
| JP | 2012-075495 | 4/2012 |
| JP | 2013-529478 | 7/2013 |
| JP | 2013-165830 | 8/2013 |
| JP | 2013-252165 | 12/2013 |
| JP | 2014-064681 | 4/2014 |
| WO | 97/36636 | 10/1997 |
| WO | 2011/110888 | 9/2011 |
| WO | 2014/021390 | 2/2014 |

\* cited by examiner

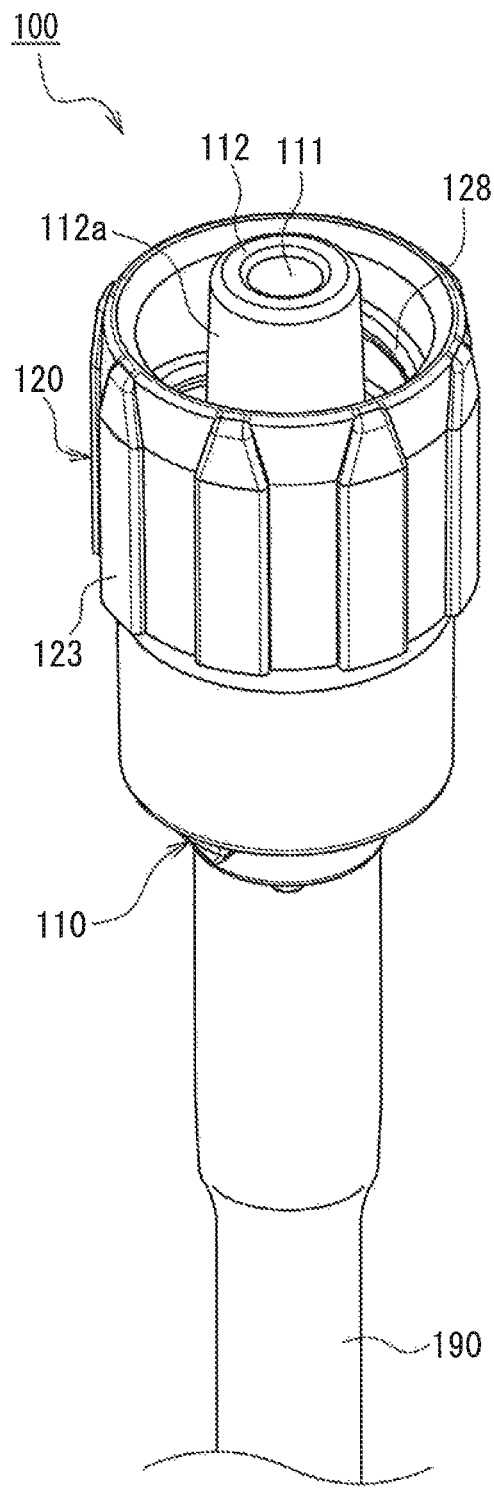
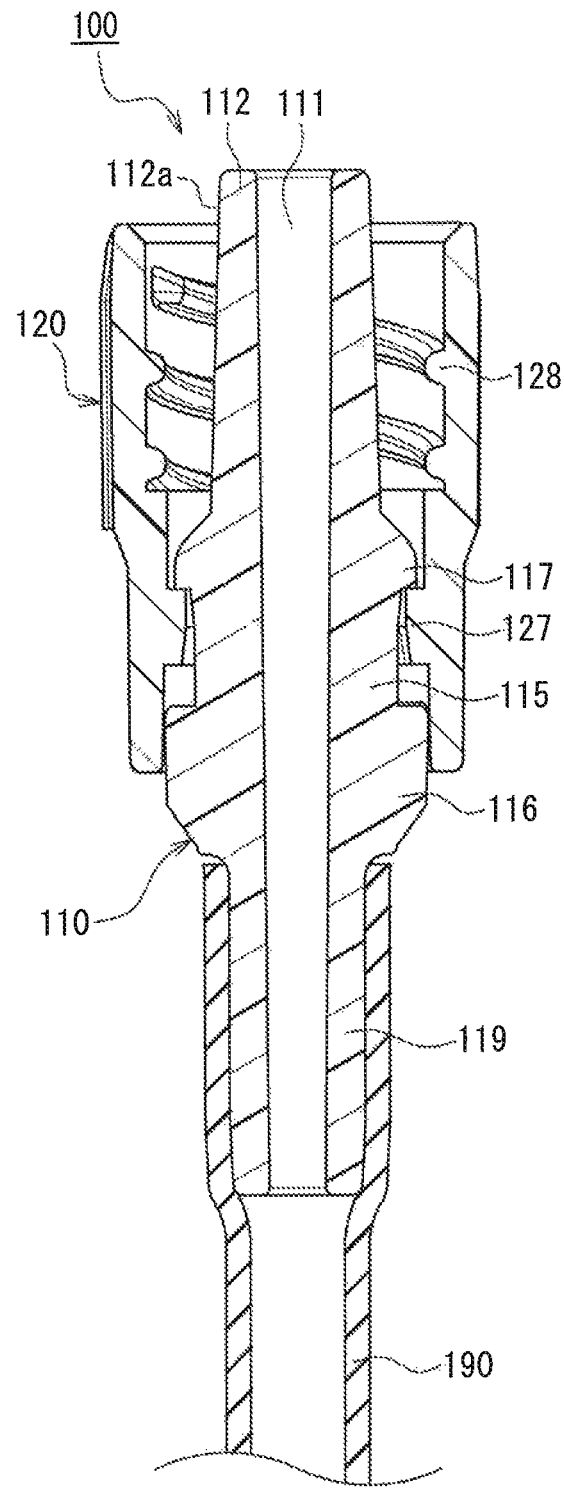
FIG. 8A
FIG. 8B

LEVER LOCK MALE CONNECTOR AND MALE CONNECTOR ASSEMBLY

TECHNICAL FIELD

The present invention relates to a male connector including a lever-type lock mechanism for maintaining a state in which the male connector is connected to a female connector. The present invention also relates to a male connector assembly including the male connector.

BACKGROUND ART

In the field of medicine, circuits (lines) are used to convey various liquids such as medicinal solutions, infusion solutions, and blood. Such circuits are generally formed by connecting containers, various instruments, tubes, and the like. In order to connect different members, a connecting device constituted by a male connector and a female connector is used.

Many connecting devices for medical use are provided with a lock mechanism for locking a connected state in which the male connector and the female connector are connected to each other so as to prevent unintentional disconnection of the male connector and the female connector during treatment.

Patent Document 1 discloses a screw lock mechanism using a screw. The male connector includes a male luer on which a male tapered surface that becomes gradually narrower at one end is formed, and a lock nut that is rotatable around the male luer. A female thread is formed in the lock nut. The female connector includes a female tapered surface that can be fitted to the male tapered surface of the male luer and a male thread that can be screwed into the female thread of the lock nut. In a state in which the male luer is inserted into the female connector, the female thread of the lock nut is screwed onto the male thread of the female connector (locked state).

A screw lock mechanism has a problem in that it is difficult for a user to accurately know the screwed state of the male thread and the female thread. Thus, if the male thread and the female thread are excessively strongly screwed together, problematic situations, such as the threads breaking and the screwed connection becoming difficult to release, may occur. Conversely, if the male thread and the female thread are loosely screwed together, problematic situations, such as loosening of the screwed connection between the male thread and the female thread as well as the resulting leakage of a liquid through a gap between the male tapered surface and the female tapered surface, disconnection of the male connector and the female connector, and the like, may occur.

Patent Document 2 discloses a lever lock mechanism serving as a lock mechanism that addresses the above-described problem with screw lock mechanisms, the lever lock mechanism including elastically pivotable levers. The male connector includes a pair of levers such that the male luer is disposed therebetween. The levers are each held in a seesaw manner. A claw is formed at a leading end of each lever. The male luer is inserted into the female connector, and the claws are engaged with the female connector (locked state). In order to disconnect the male connector and the female connector from each other, the levers are caused to pivot by pressing the portions (operating portions) of the levers that are located on the opposite side to the claws. Thus, the claws are disengaged from the female connector.

With a lever lock mechanism, the male connector and the female connector can be easily connected and disconnected to and from each other, and therefore, the ease of operation is favorable. Moreover, switching between the locked state and a non-locked state depends on whether or not the claws of the levers are engaged with the female connector, and therefore, the connected state is highly stable and reliable.

CITATION LIST

Patent Documents

Patent Document 1: JP H7-148271A
Patent Document 2: JP 2004-483A

DISCLOSURE OF INVENTION

Problem to be Solved by the Invention

In a conventional lever lock mechanism, if an external force is applied to the operating portions of the levers, engagement of the claws with the female connector can be easily released. For this reason, there is a problem in that, for example, even when an unintentional external force acts on the operating portions as a result of the male connector being pinned under a patient's body, the claws are disengaged from the female connector.

The present invention was made to address the above-described problem with conventional lever lock mechanisms, and it is an object thereof to reduce the likelihood of a locked state being unintentionally cancelled, while maintaining favorable ease of operation.

Means for Solving Problem

A lever lock male connector of the present invention has a connector main body including a rod-shaped male luer, a tubular hood surrounding the male luer, and a lever connected to a base end portion of the male luer via a base. The male luer is disposed coaxially with a central axis of the connector main body. The lever includes a locking portion that is disposed on the same side as the male luer relative to the base, an operating portion that is disposed on the opposite side to the male luer relative to the base, and a locking claw that protrudes toward the male luer from a surface of the locking portion that is located on a side facing the male luer. The locking portion is disposed within a cut-out that is formed in the hood. The lever is elastically pivotable so that, when an outer surface of the operating portion is pressed, the locking claw moves away from the male luer.

In a first lever lock male connector, when the connector main body is viewed along the central axis, the connector main body has a major axis in a direction in which the male luer opposes the lever.

A second lever lock male connector further has a lever pivotal movement prevention mechanism that prevents the lever from pivoting such that the locking claw moves away from the male luer. When the male connector is viewed along the central axis, the male connector has a major axis in the direction in which the male luer opposes the lever.

A male connector assembly of the present invention includes the above-described first or second lever lock male connector of the present invention and a screw lock connector. The connector main body further includes a tubular portion on the opposite side to the male luer relative to the base, the tubular portion being in communication with the male luer. A female tapered surface is formed on an inner circumferential surface of the tubular portion, the female tapered surface having an internal diameter that increases as the distance to a leading end of the tubular portion decreases. A male thread is formed on an outer circumferential surface of the tubular portion. The screw lock connector includes a luer main body provided with a male tapered surface that can be fitted to the female tapered surface of the tubular portion and a lock nut that is rotatable around the luer main body. The lock nut is provided with a female thread that can be screwed onto the male thread of the tubular portion.

Effects of the Invention

The connector main body includes the lever that is held by the base in a seesaw manner. The lever includes the locking claw that is engageable with the female connector. Therefore, as is the case with a male connector including a conventional lever lock mechanism, the male connector and the male connector assembly of the present invention, which have the connector main body, provide excellent ease of operation for connection and disconnection to and from the female connector.

When viewed along the central axis, the connector main body or the male connector has the major axis in the direction in which the male luer opposes the lever. Therefore, if the male connector or the male connector assembly is pinned under a patient with the central axis extending in the horizontal direction, the male connector or the male connector assembly can easily rotate so that the direction of the major axis becomes the horizontal direction. Therefore, the likelihood of an unintentional external force acting on the operating portion is low. Consequently, the likelihood of a state (locked state) in which the locking claw of the lever is engaged with the female connector being unintentionally cancelled is low.

BRIEF DESCRIPTION OF DRAWINGS

FIG. 8A is a perspective view of a screw lock connector according to the embodiment of the present invention, and FIG. 8B is a cross-sectional view of the screw lock connector.

DESCRIPTION OF THE INVENTION

Figure 1:
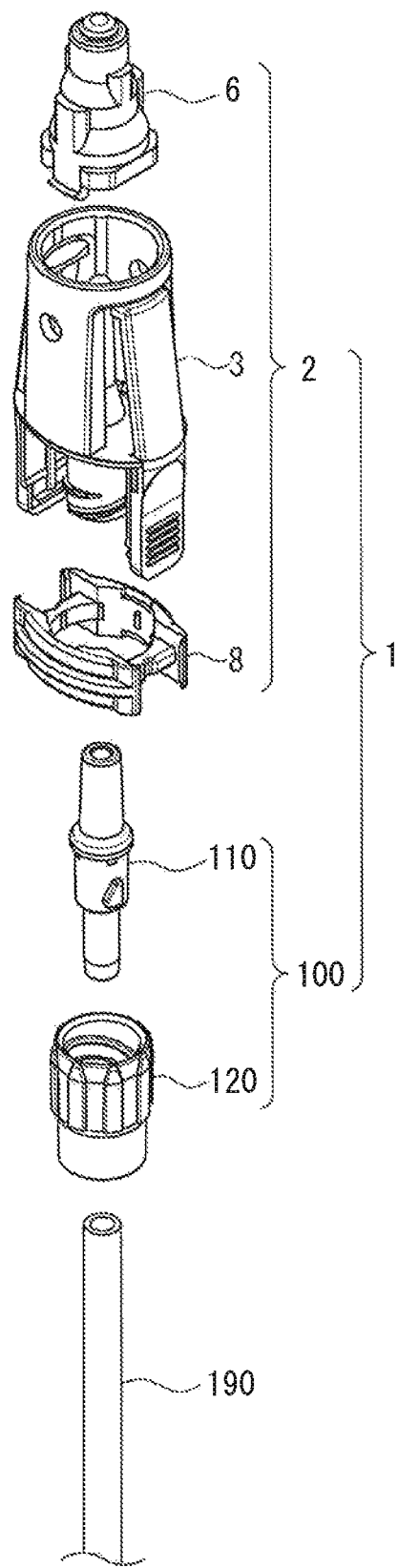
FIG. 1 is an exploded perspective view of a male connector assembly according to an embodiment of the present invention.

In the present invention, the "major axis" means an axis extending along a direction in which the external dimension is largest. Therefore, a connector main body (or a male connector) "having a major axis in the direction in which the male luer opposes the lever" when viewed along the central axis (i.e., in plan view) means that the external dimension of the connector main body (or the male connector) when viewed along the central axis is largest in the direction in which the male luer opposes the lever. The "external dimension" is defined by the distance between two points at which a straight line that is orthogonal to the central axis intersects an outline (projected shape along the central axis) that defines the external shape of the connector main body (or the male connector) when viewed along the central axis.

In the present invention, as long as the connector main body (or the male connector) when viewed along the central axis has the major axis in the direction in which the male luer opposes the lever, the outline shape (i.e., projected shape along the central axis) of the connector main body (or the male connector) when viewed along the central axis can be any shape. Preferably, the outline shape is symmetrical with respect to the major axis. Also, preferably, a minor axis of the outline shape intersects the major axis at right angles on the central axis. The "minor axis" as used herein means an axis extending along a direction in which the external dimension is smallest. Preferably, the outline shape has only one major axis. Also, preferably, the outline shape has only one minor axis. Therefore, shapes (e.g., regular polygonal shapes such as squares) having two or more major axes and circles having a constant external dimension in any direction around the central axis are not preferred as the outline shapes of the connector main body and the male connector. Even when an outline shape has a protrusion or a recess, if the protrusion or the recess is minute in comparison with the overall outline shape, and it is judged that the protrusion or the recess has substantially no effect on the rotation of the male connector or the male connector assembly when pinned under the patient, the major axis, the minor axis, and the outline shape can be defined in disregard of such protrusion or recess.

In the above-described first lever lock male connector of the present invention, it is preferable that the connector main body has a substantially elliptical outline when viewed along the central axis. With this preferred configuration, if the male connector or the male connector assembly including the above-described connector main body is pinned under the patient with the central axis extending in the horizontal direction, the male connector or the male connector assembly can more easily rotate so that the direction of the major axis of the substantially elliptical shape becomes the horizontal direction. Therefore, the likelihood of the state (locked state) in which the locking claw of the lever is engaged with the female connector being unintentionally cancelled is further reduced.

The above-described first male connector of the present invention may further include a lever pivotal movement prevention mechanism that prevents the lever from pivoting such that the locking claw moves away from the male luer. With this preferred configuration, the likelihood of the state (locked state) in which the locking claw of the lever is engaged with the female connector being unintentionally cancelled is further reduced.

It is preferable that, when the first male connector is viewed along the central axis, the lever pivotal movement prevention mechanism does not protrude outward from the connector main body (in particular, the substantially elliptical outline of the connector main body). With this preferred configuration, if the male connector or the male connector assembly is pinned under the patient, the male connector or the male connector assembly can easily rotate so that the direction of the major axis becomes the horizontal direction.

In the above-described second lever lock male connector of the present invention, it is preferable that the male connector has a substantially elliptical outline when viewed along the central axis. With this preferred configuration, if this male connector or a male connector assembly including the male connector is pinned under the patient with the central axis extending in the horizontal direction, the male connector or the male connector assembly can more easily rotate so that the direction of the major axis of the substantially elliptical shape becomes the horizontal direction. Therefore, the likelihood of the state (locked state) in which the locking claw of the lever is engaged with the female connector being unintentionally cancelled is further reduced.

In the above-described second male connector, the substantially elliptical outline may be constituted by the connector main body and the lever pivotal movement prevention mechanism. With this configuration, the degree of freedom of design of the connector main body and the lever pivotal movement prevention mechanism is improved.

The lever pivotal movement prevention mechanism may be disposed so as to abut against an inner surface of the operating portion. With this preferred configuration, the configuration of the lever pivotal movement prevention mechanism can be simplified, and the reliability of the operation of the lever pivotal movement prevention mechanism can be improved. Moreover, the lever pivotal movement prevention mechanism that does not protrude from the substantially elliptical outline of the connector main body when viewed along the central axis can be easily realized.

It is preferable that the lever pivotal movement prevention mechanism can be displaced to a first position at which the lever pivotal movement prevention mechanism allows the lever to pivot and a second position at which the lever pivotal movement prevention mechanism does not allow the lever to pivot. With this preferred configuration, activation/deactivation of the lever pivotal movement prevention mechanism can be switched through an extremely simple operation of moving the lever pivotal movement prevention mechanism.

The above-described male connector of the present invention may include a first movement prevention mechanism that prevents the lever pivotal movement prevention mechanism at the first position from moving toward the second position or a second movement prevention mechanism that prevents the lever pivotal movement prevention mechanism at the second position from moving toward the first position. Furthermore, the male connector of the present invention may include both the first movement prevention mechanism and the second movement prevention mechanism. With the first movement prevention mechanism, the ease of operation for connecting the male connector and the female connector to each other can be prevented from deteriorating as a result of the lever pivotal movement prevention mechanism at the first position moving toward the second position. With the second movement prevention mechanism, the engagement of the locking claw of the lever with the female connector can be prevented from being unintentionally cancelled as a result of the lever pivotal movement prevention mechanism at the second position moving toward the first position.

A leading end of the hood may have a circular shape that is coaxial with the central axis. In this case, it is preferable that an external diameter of the hood at the leading end is equal to or smaller than a minor diameter of the substantially elliptical shape along the minor axis. With this preferred configuration, the size of a portion that is located above (on the hood side of) the base can be reduced.

The operating portion of the lever may be located nearer to the central axis than a portion of the lever that is connected to the base. With this preferred configuration, when the male connector collides with a neighboring device or the male connector is pinned under the patient's body, the likelihood of an unintentional external force acting on the operating portion is low. For this reason, the likelihood of the state (locked state) in which the locking claw of the lever is engaged with the female connector being unintentionally cancelled is further reduced.

A portion of the male connector that protrudes furthest from the central axis in the radial direction may be a portion (lever base portion) of the lever that is connected to the base. With this preferred configuration, an unintentional external force is more likely to be applied to the lever base portion, and less likely to be applied to the operating portion. Thus, the likelihood of the state (locked state) in which the locking claw of the lever is engaged with the female connector being unintentionally cancelled is further reduced.

A flow channel through which a liquid flows may be provided in the male luer. An opening that is in communication with the flow channel may be provided in an outer circumferential surface of the male luer. In this case, the male connector may further include a shield that closes the opening. It is preferable that, when the male luer is inserted into the female connector, the shield is compressively deformed in a longitudinal direction of the male luer, and the opening is exposed. Thus, when the male connector or the male connector assembly is not connected to the female connector, leakage of a liquid to the outside through the opening can be prevented. Therefore, even if the lever lock mechanism or the lever pivotal movement prevention mechanism does not function for some reason, and the male luer is unintentionally dislodged from the female connector, the liquid can be prevented from leaking.

The above-described male connector of the present invention may include two of the levers. In this case, it is preferable that the two levers are arranged at symmetrical positions with respect to the central axis. With this preferred configuration, the female connector can be stably held with two locking claws, and thus, the locked state can be stably maintained.

The above-described male connector assembly of the present invention may further include a rotation prevention mechanism that prevents the lock nut from rotating in a state in which the male tapered surface of the luer main body has been fitted to the female tapered surface of the tubular portion and the female thread of the lock nut has been screwed onto the male thread of the tubular portion. With this configuration, loosening of the screwed connection between the female thread of the lock nut and the male thread of the tubular portion can be prevented, which is advantageous in preventing the occurrence of an unforeseen situation, such as leakage of the liquid from between the male luer and the tubular portion or dislodgement of the male luer from the tubular portion.

It is preferable that the rotation prevention mechanism also functions as a lever pivotal movement prevention mechanism that prevents the lever from pivoting such that the locking claw moves away from the male luer. With this preferred configuration, the number of members constituting the male connector assembly can be reduced, and the configuration of the male connector assembly can be simplified.

The rotation prevention mechanism may have an annular shape with an opening formed at the center thereof. In this case, it is preferable that the tubular portion or the luer main body is disposed in the opening of the rotation prevention mechanism. With this preferred configuration, the rotation prevention mechanism that prevents rotation of the lock nut by being engaged with or fitted to the lock nut can be easily realized.

Hereinafter, the present invention will be described in detail while showing preferred embodiments thereof. However, it goes without saying that the present invention is not limited to the embodiments below. In the drawings that will be referred to in the following description, only the main members of constituent members of the embodiments of the present invention are shown in a simplified manner for the sake of convenience of description. Accordingly, the present invention may include optional members that are not shown in the drawings below. Moreover, it should be understood that the members shown in the drawings below may be changed or omitted within the scope of the present invention.

FIG. 1 is an exploded perspective view of a male connector assembly 1 according to an embodiment of the present invention. The male connector assembly 1 includes a lever lock male connector (hereinafter simply referred to as "male connector") 2 and a screw lock connector 100. The male connector 2 includes a connector main body 3, a shield 6, and a lock ring 8. The screw lock connector 100 includes a luer main body 110 and a lock nut 120. A flexible tube 190 is connected to the male connector 2 via the screw lock connector 100.

Hereinafter, the various portions will be sequentially described.

1. Male Connector 1. 1. Connector Main Body

Figure 2A:
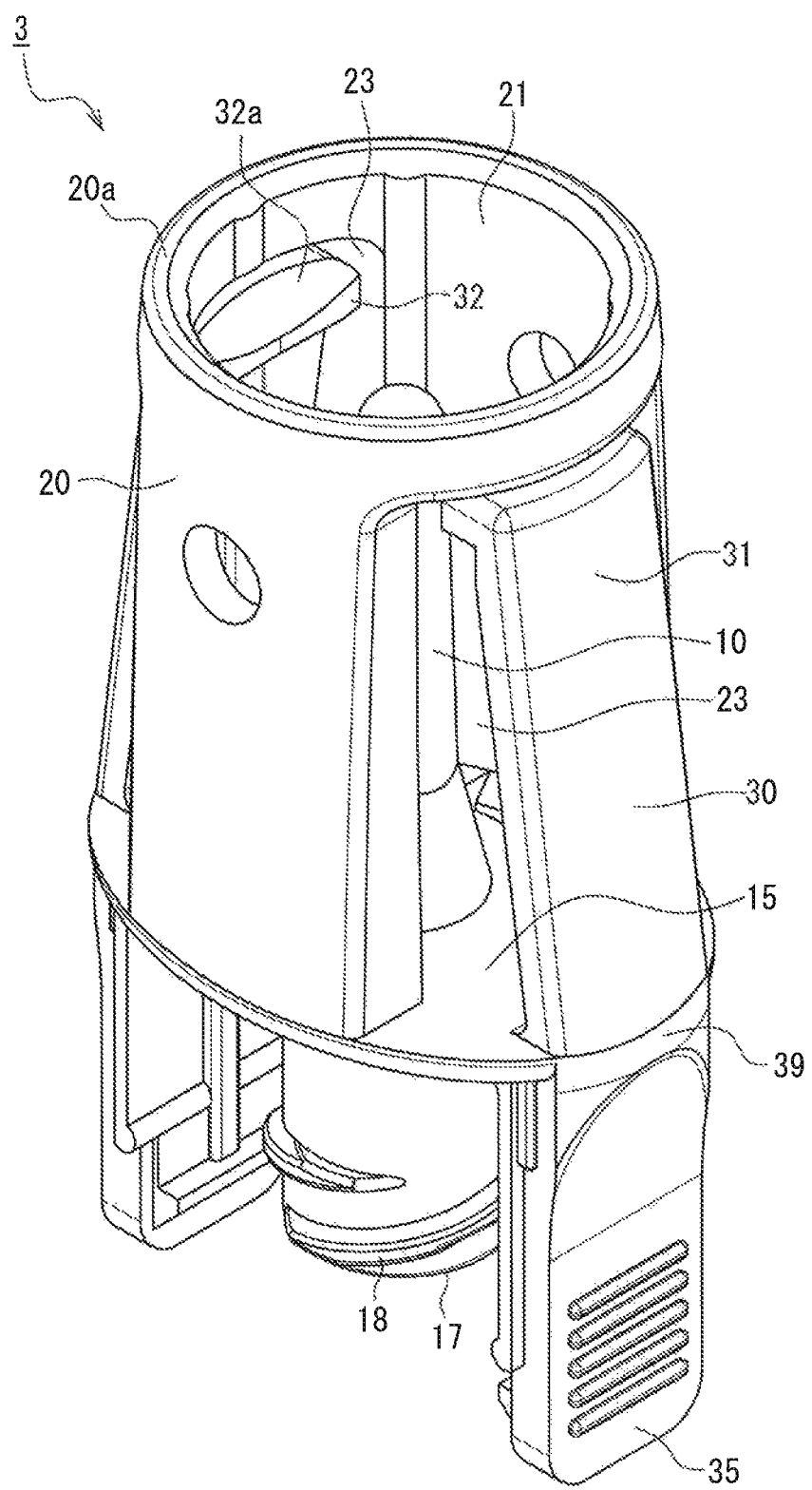
FIG. 2A is a perspective view of a connector main body according to the embodiment of the present invention when viewed from above.
Figure 2B:
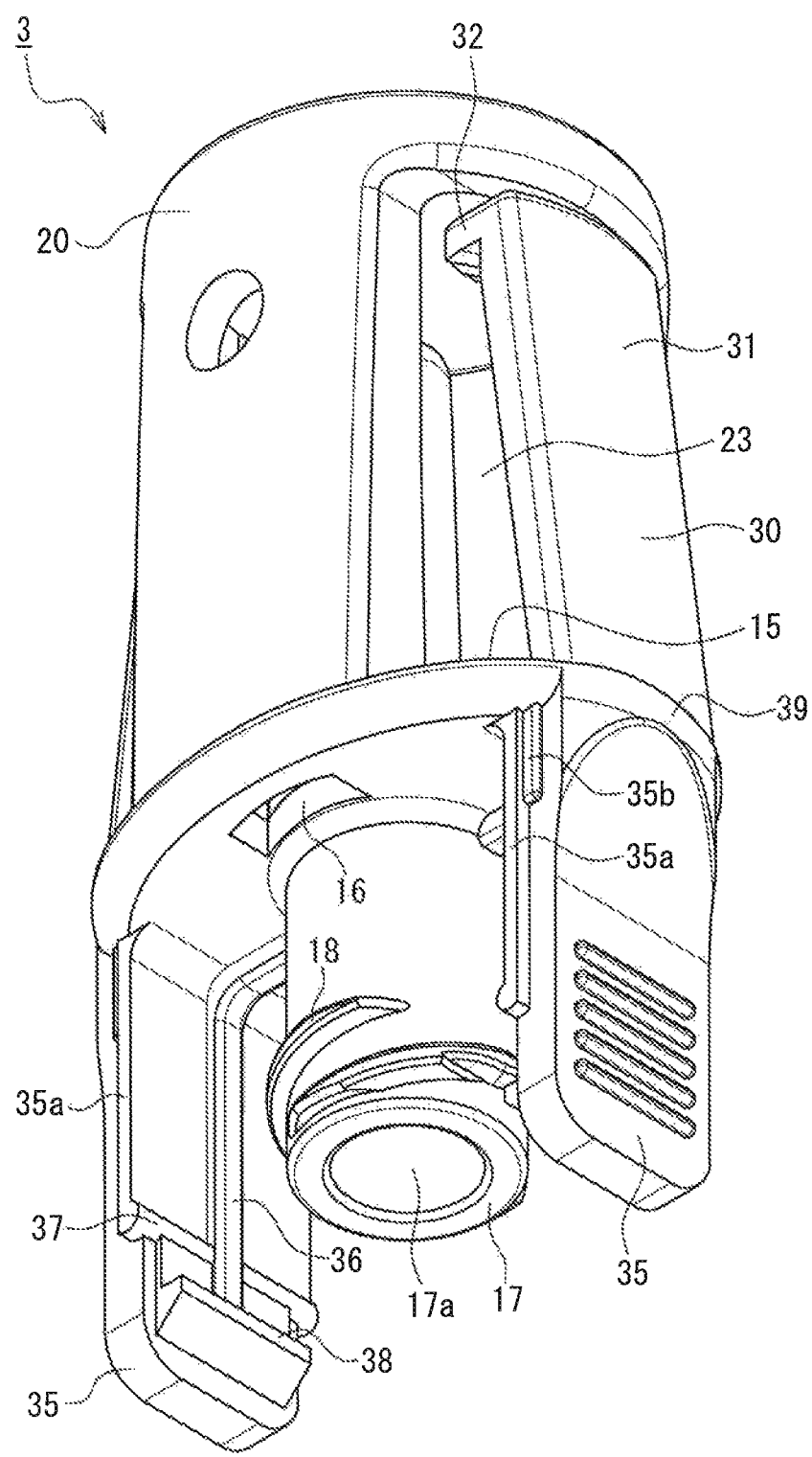
FIG. 2B is a perspective view of the connector main body when viewed from below.
Figure 2C:
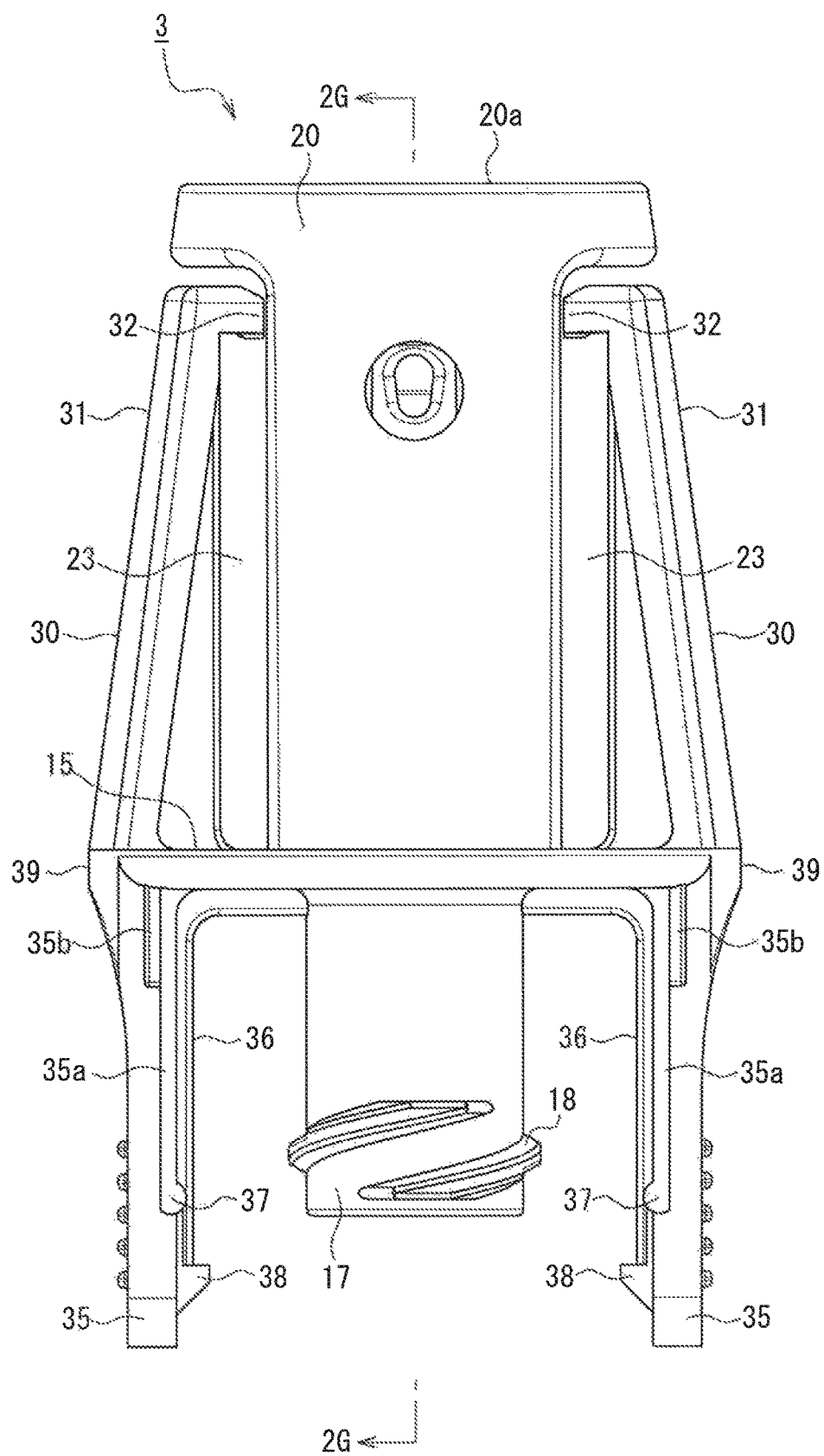
FIG. 2C is a front view of the connector main body.
Figure 2D:
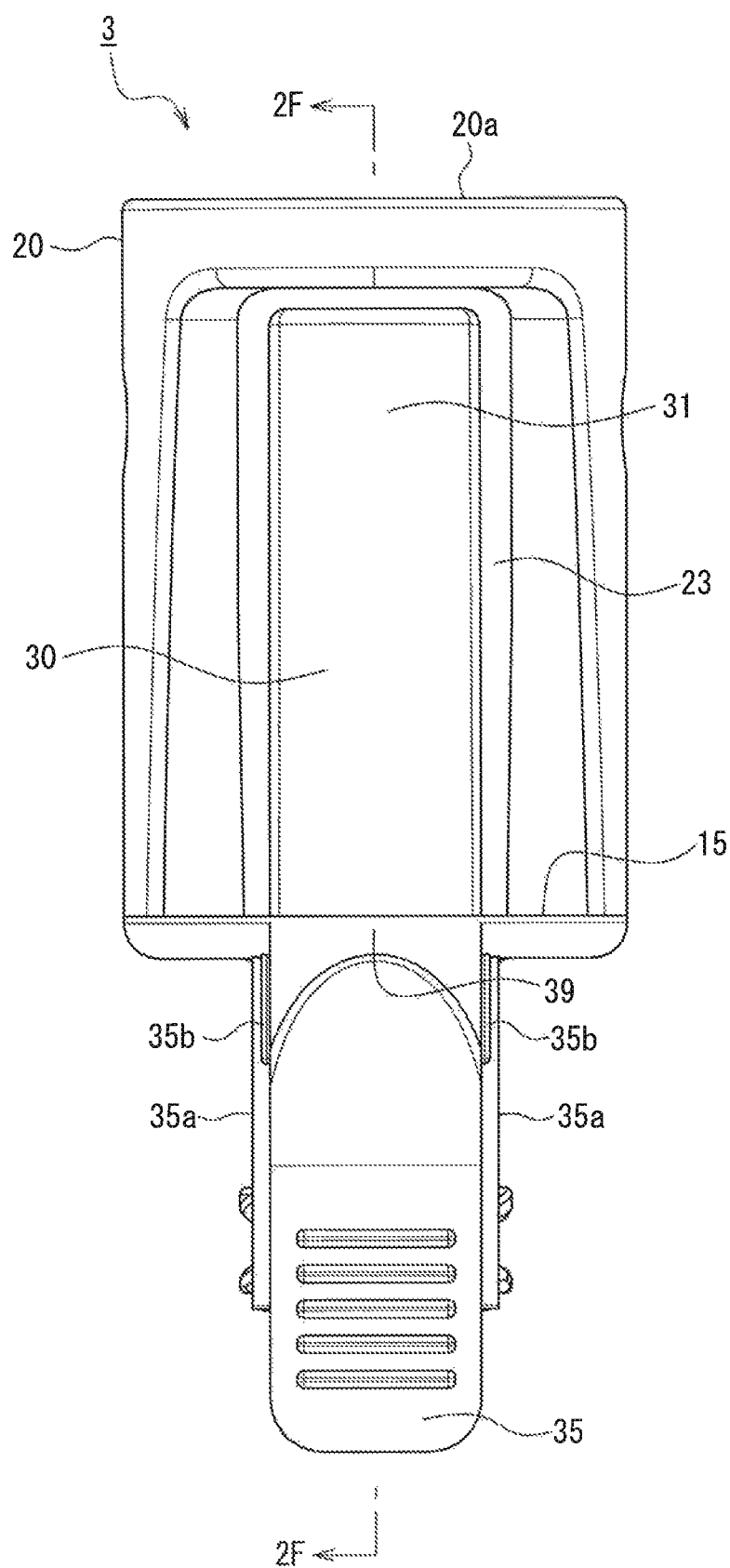
FIG. 2D is a side view of the connector main body.
Figure 2E:
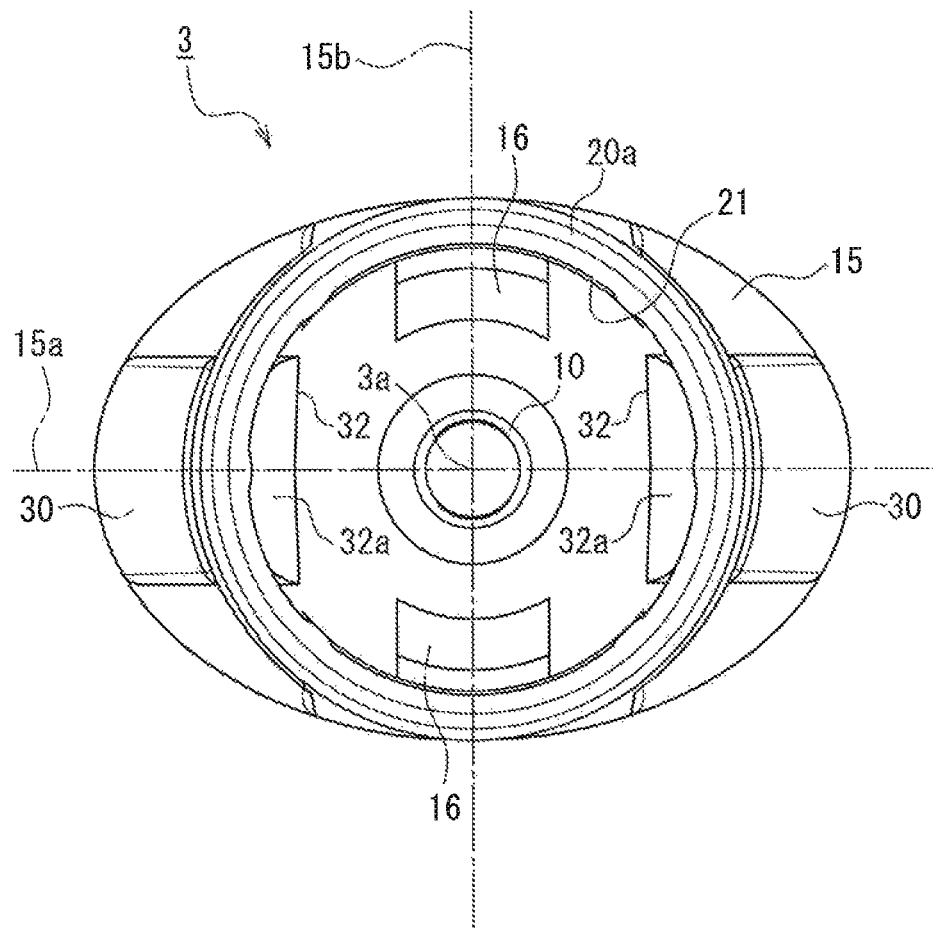
FIG. 2E is a plan view of the connector main body.
Figure 2F:
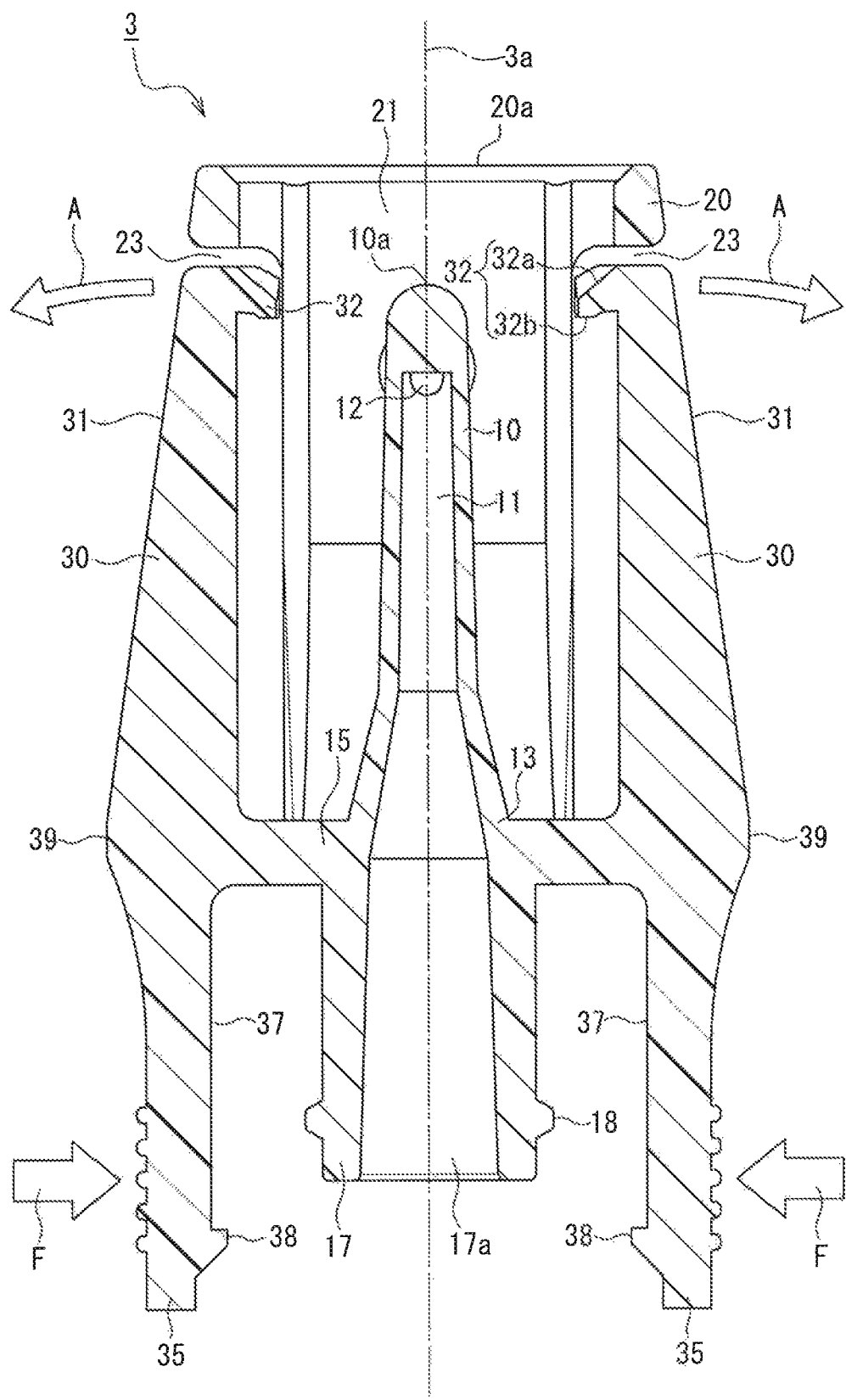
FIG. 2F is a cross-sectional view of the connector main body taken along a vertical plane containing line 2F-2F in FIG. 2D.
Figure 2G:
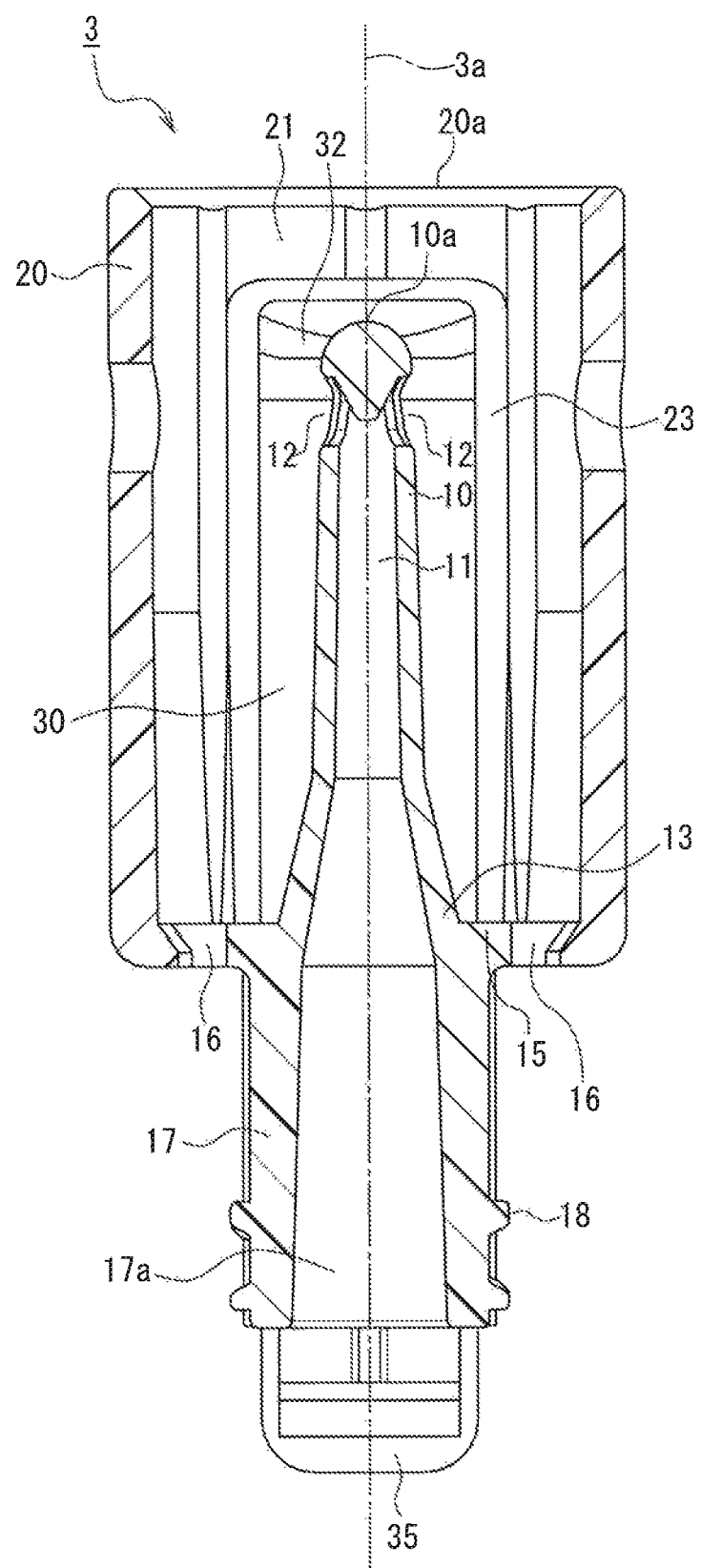
FIG. 2G is a cross-sectional view of the connector main body taken along a vertical plane containing line 2G-2G in FIG. 2C.

The connector main body 3 constituting the male connector 2 will be described. FIG. 2A is a perspective view of the connector main body 3 when viewed from above, and FIG. 2B is a perspective view of the connector main body 3 when viewed from below. FIGS. 2C, 2D, and 2E are a front view, a side view, and a plan view, in that order, of the connector main body 3. FIG. 2F is a cross-sectional view of the connector main body 3 taken along a vertical plane containing line 2F-2F in FIG. 2D. FIG. 2G is a cross-sectional view of the connector main body 3 taken along a vertical plane containing line 2G-2G in FIG. 2C. In FIGS. 2F and 2G, a long dashed short dashed line 3a represents the central axis of the connector main body 3. The central axis 3a also serves as the central axis of all the members (see FIG. 1) that constitute the male connector assembly 1.

For the sake of convenience of the following description, a direction that is parallel to the central axis 3a is referred to as "vertical direction", a direction that is parallel to a plane that is perpendicular to the central axis 3a is referred to as "horizontal direction", a direction that is orthogonal to the central axis 3a is referred to as "radial direction" or "diameter direction", and the direction of rotation about the central axis 3a is referred to as "circumferential direction". With respect to the radial direction, the side nearer the central axis 3a is referred to as "inner side", and the side further from the central axis 3a is referred to as "outer side". "Up" and "down" are defined based on FIGS. 1 and 2A. However, the "vertical direction" and the "horizontal direction" do not mean the actual orientation of the male connector 2 and the male connector assembly 1 during usage.

As shown in FIGS. 2F and 2G, the connector main body 3 includes a male luer 10 serving as a male member. The male luer 10 is a rod-shaped member extending along and coaxially with the central axis 3a. In the present embodiment, an outer circumferential surface (side surface) of a portion of the male luer 10 that is near a leading end 10a and that is to be inserted into a female member (septum 210, which will be described later) constitutes a cylindrical surface whose external diameter is constant with respect to the direction of the central axis 3a, and an outer circumferential surface of a portion of the male luer 10 that is near a base end portion 13 constitutes a tapered surface (conical surface) whose external diameter decreases as the distance to the leading end 10a decreases. However, the shape of the outer circumferential surface of the male luer 10 is not limited to the above-described shape, and can be selected as desired. For example, the outer circumferential surface of the male luer 10 may constitute a cylindrical surface whose external diameter is constant from the base end portion 13 to the leading end 10a. Alternatively, the outer circumferential surface of the male luer 10 may constitute a smooth curved surface whose external diameter gradually decreases from the base end portion 13 toward the leading end 10a.

A flow channel 11 is formed along the central axis 3a within the male luer 10. The flow channel 11 is not open in the leading end 10a of the male luer 10. Two lateral holes 12 that are in communication with the flow channel 11 are formed in the outer circumferential surface of the male luer 10 at respective positions near the leading end 10a. Each lateral hole 12 penetrates the male luer 10 in the radial direction and is open in the outer circumferential surface of the male luer 10. It should be noted that the number of lateral holes 12 is not necessarily required to be two, and may also be one, or three or more.

A base 15 protrudes outward from the base end portion 13 of the male luer 10. The base 15 is a flat plate-shaped member that is parallel to the horizontal direction. As can be understood from FIG. 2E, when viewed along the central axis 3a, the base 15 has a substantially elliptical shape.

A tubular portion 17 protrudes downward from the base 15. The tubular portion 17 has a substantially cylindrical tubular shape that is coaxial with the central axis 3a, and a flow channel that is in communication with the flow channel 11 of the male luer 10 is formed in the tubular portion 17. An inner circumferential surface 17a of the tubular portion 17 constitutes a female tapered surface (e.g., a 6% tapered surface) whose internal diameter increases as the distance from the base 15 increases. A male thread 18 is formed on an outer circumferential surface of the tubular portion 17.

A hood 20 extends upright from an outer end edge of the base 15 toward the same side as the male luer 10. The hood 20 has a hollow tubular shape that surrounds the male luer 10. The hood 20 is open upward. A leading end (upper end) 20a of the hood 20 that surrounds an opening 21 has a circular shape that is coaxial with the central axis 3a. The leading end 20a of the hood 20 is located at a higher position than the leading end 10a of the male luer 10.

A pair of cut-outs 23 are provided in a side wall of the hood 20. The cut-outs 23 are holes (openings) penetrating the hood 20 in the radial direction. The pair of cut-outs 23 oppose each other with the male luer 10 disposed therebetween. The direction in which the pair of cut-outs 23 oppose each other is the same as the direction of a major axis 15a (see FIG. 2E) of the base 15 having the substantially elliptical shape. Each cut-out 23 has an inverted "U"-shape (see FIG. 2D), and a lower end thereof reaches the base 15. However, the cut-outs 23 do not reach the leading end 20a of the hood 20.

As is best shown in FIG. 2F, a pair of levers 30 oppose each other with the central axis 3a disposed therebetween. The direction in which the pair of levers 30 oppose each other is the same as the direction of the major axis 15a (see FIG. 2E) of the base 15 having the substantially elliptical shape. The levers 30 are rectangular strip-shaped members that extend substantially parallel to the central axis 3a. The longitudinal direction of the levers 30 extends along a vertical plane containing the central axis 3a and the major axis 15a. The levers 30 are connected to the outer end edge of the base 15. Each lever 30 includes a locking portion 31 that is disposed on the same side (upper side) as the male luer 10 relative to the base 15 and an operating portion 35 that is disposed on the opposite side (lower side) to the male luer 10 relative to the base 15. A portion of each lever 30 which is located between the locking portion 31 and the operating portion 35 and to which the base 15 is connected is referred to as a lever base portion 39.

The locking portions 31 are disposed within the respective cut-outs 23 that are formed in the hood 20. In other words, the locking portions 31 are surrounded by the respective inverted "U"-shaped slits 23 that penetrate the hood 20 in the radial direction (see FIG. 2D).

A locking claw 32 protrudes toward the male luer 10 from a surface (inner surface) of each locking portion 31 that opposes the male luer 10. Each locking claw 32 includes an inclined surface 32a and an engagement surface 32b. The inclined surface 32a is inclined such that the distance from the male luer 10 increases as the distance from the base 15 increases. The engagement surface 32b is a flat surface that is disposed nearer to the base 15 than the inclined surface 32a and that is substantially parallel to a horizontal plane (plane that is orthogonal to the central axis 3a). As shown in FIG. 2E, when viewed from above, the top portion (portion that is nearest to the male luer 10) of each claw 32 protrudes toward the male luer 10 beyond the leading end 20a that surrounds the opening 21 of the hood 20.

As will be described later, when the male connector 2 is connected to a female connector, the locking claws 32 are engaged with the female connector (see FIG. 13D, which will be described later). The levers 30 function as a "lever lock mechanism" that maintains the state in which the male connector 2 and the female connector are connected to each other. Since the two levers 30 are disposed at respective positions that are symmetrical with respect to the central axis 3a (i.e., the male luer 10), the two locking claws 32 can be engaged with the female connector at respective positions that are symmetrical with respect to the central axis 3a. Accordingly, the female connector can be stably held, and thus, the reliability of the lever lock mechanism is improved. The state in which the locking claws 32 are engaged with the female connector is referred to as "locked state".

Each lever 30 has a mechanical strength that is high enough for the entire lever 30 from the upper end (locking portion 31) to the lower end (operating portion 35) to be regarded as a substantially rigid body. In contrast, the mechanical strength of the base 15 that joins the base end portion 13 of the male luer 10 to each lever 30 is relatively low. Therefore, when a force F acting toward the central axis 3a is applied to outer surfaces of the operating portions 35 as shown in FIG. 2F, the base 15 can elastically deform and bend, thereby allowing the levers 30 to pivot (or swing) such that the locking portions 31 and the locking claws 32 formed on the respective locking portions 31 move away from the male luer 10 (in the directions of arrows A).

As shown in FIG. 2B, a rib 36 protruding toward the central axis 3*a* from an inner surface (surface that opposes the tubular portion 17) of each operating portion 35 extends in the vertical direction. A stopping projection 38 is provided at a lower end of each rib 36, the stopping projection 38 protruding further toward the central axis 3*a* than the rib 36. A locking projection 37 protruding toward the central axis 3*a* is provided at a position that is slightly spaced upward from the stopping projection 38. The amount by which each locking projection 37 protrudes from the inner surface of a corresponding one of the operating portions 35 is smaller than that of the stopping projection 38. In a natural state (initial state) in which no external force is applied to the levers 30, the distance between the mutually opposing operating portions 35 is constant with respect to the vertical direction. Sliding ribs 35*a* extending in the vertical direction protrude from respective side surfaces of each operating portion 35. Furthermore, pressure contact ribs 35*b* protrude from positions on the respective side surfaces of each operating portion 35 that are near the base 15, the pressure contact ribs 35*b* being adjoined to the sliding ribs 35*a* on the side of the sliding ribs 35*a* away from the tubular portion 17.

As shown in FIGS. 2B and 2G, a pair of holes 16 penetrating the base 15 in the vertical direction are formed in the base 15. The holes 16 are disposed on a minor axis 15*b* (see FIG. 2E) of the base 15 having the substantially elliptical shape.

As shown in FIG. 2C, when viewed along a direction that is orthogonal to the central axis 3*a* and the major axis 15*a* (in front view), the connector main body 3 has the largest horizontal dimension at the position of the base 15 (i.e., lever base portions 39). A portion of the connector main body 3 that is located above the base 15 has a tapered shape (or a trapezoidal shape) whose horizontal dimension gradually decreases as the distance from the base 15 increases in the upward direction. The locking portion 31 of each lever 30 and a portion of the hood 20 that is located above the locking portions 31 extend along a common straight line. On the other hand, the operating portion 35 of each lever 30 is located nearer to the tubular portion 17 (or the central axis 3*a*) than the lever base portion 39. In this manner, of the lever base portion 39, the locking portion 31, and the operating portion 35 of each lever 30, the lever base portion 39 protrudes furthest outward from the central axis 3*a* in the horizontal direction.

As shown in FIG. 2D, when viewed along a direction that is orthogonal to the central axis 3*a* and the minor axis 15*b* (in side view), the portion of the connector main body 3 that is located above the base 15 has a rectangular shape whose horizontal dimension is substantially constant from the base 15 to the leading end 20*a* of the hood 20. The horizontal dimension of the operating portion 35 of each lever 30 is smaller than the horizontal dimensions of the base 15 and the portion of the connector main body 3 that is located above the base 15.

As shown in FIG. 2E, when viewed from above along the central axis 3*a* (in plan view), the external dimension of the connector main body 3 is largest in the direction in which the male luer 10 opposes the levers 30 (left-right direction in FIG. 2E), and is smallest in the direction that is orthogonal to this direction (up-down direction in FIG. 2E). The outline (projected shape) of the connector main body 3 of the present invention has a substantially elliptical shape having the major axis 15*a* in the direction in which the external dimension is largest and the minor axis 15*b* in the direction in which the external dimension is smallest. The substantially elliptical shape is based on the shape of the connector main body 3 at the position of the base 15 (or the lever base portions 39). The major axis 15*a* and the minor axis 15*b* intersect at right angles on the central axis 3*a*. The leading end 20*a* of the hood 20 has a circular shape that is coaxial with the central axis 3*a* and is inscribed in the above-described substantially elliptical outline of the connector main body 3.

As shown in FIG. 2A, the shape of an outer circumferential surface of the portion of the connector main body 3 that is located above the base 15 is substantially a curved surface that smoothly connects the circular shape of the leading end 20*a* of the hood 20 and the substantially elliptical shape at the position of the base 15. This curved surface is constituted by the outer circumferential surface of the hood 20 and the outer circumferential surfaces of the levers 30.

It is preferable that the connector main body 3 is made of a hard material. Specifically, a resin material such as polyacetal, polycarbonate, polystyrene, polyamide, polypropylene, or rigid polyvinyl chloride may be used. The connector main body 3 can be integrally produced as a single component through injection molding or the like using such a resin material.

1. 2. Shield

Figure 3A:
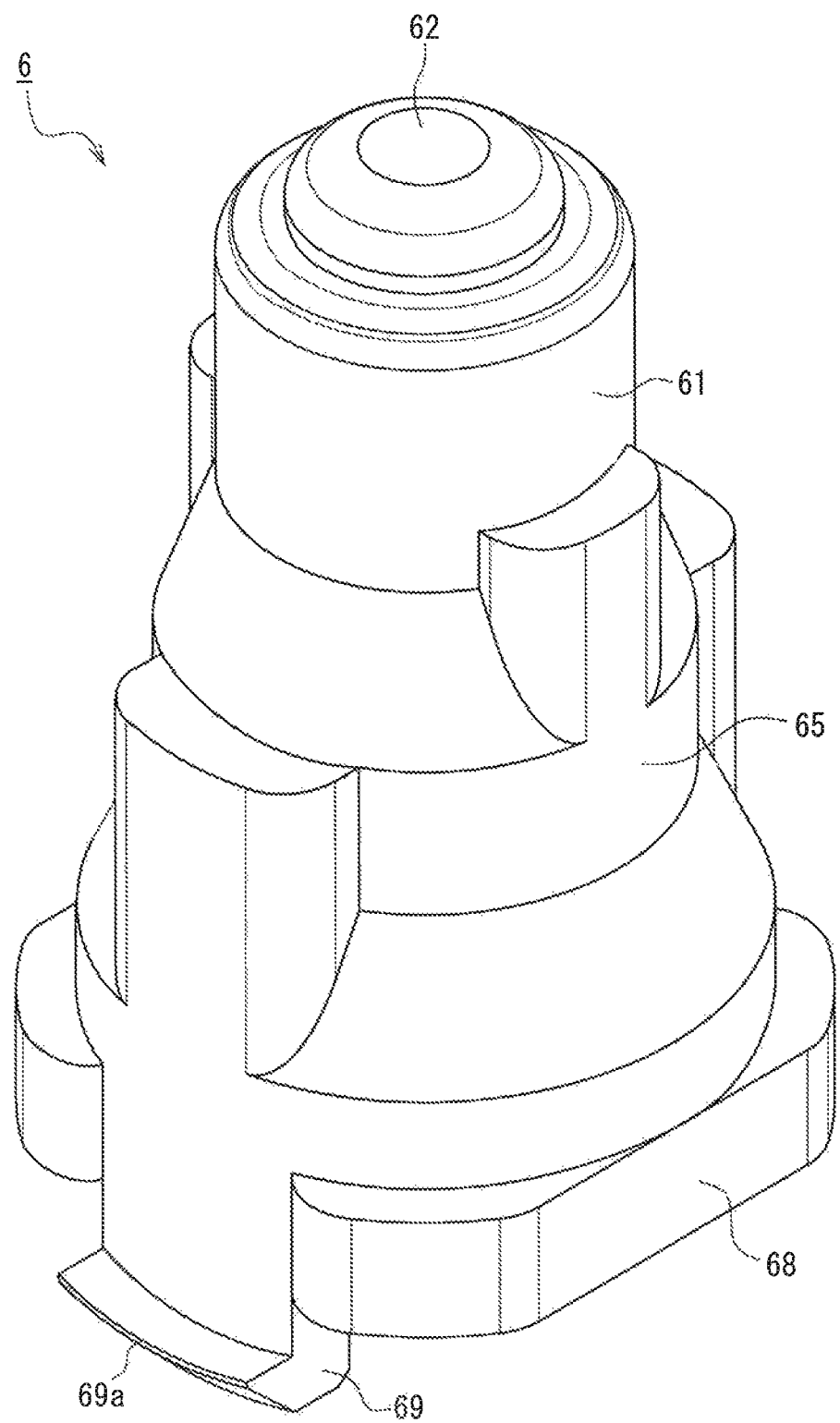
FIG. 3A is a perspective view of a shield according to the embodiment of the present invention when viewed from above.
Figure 3B:
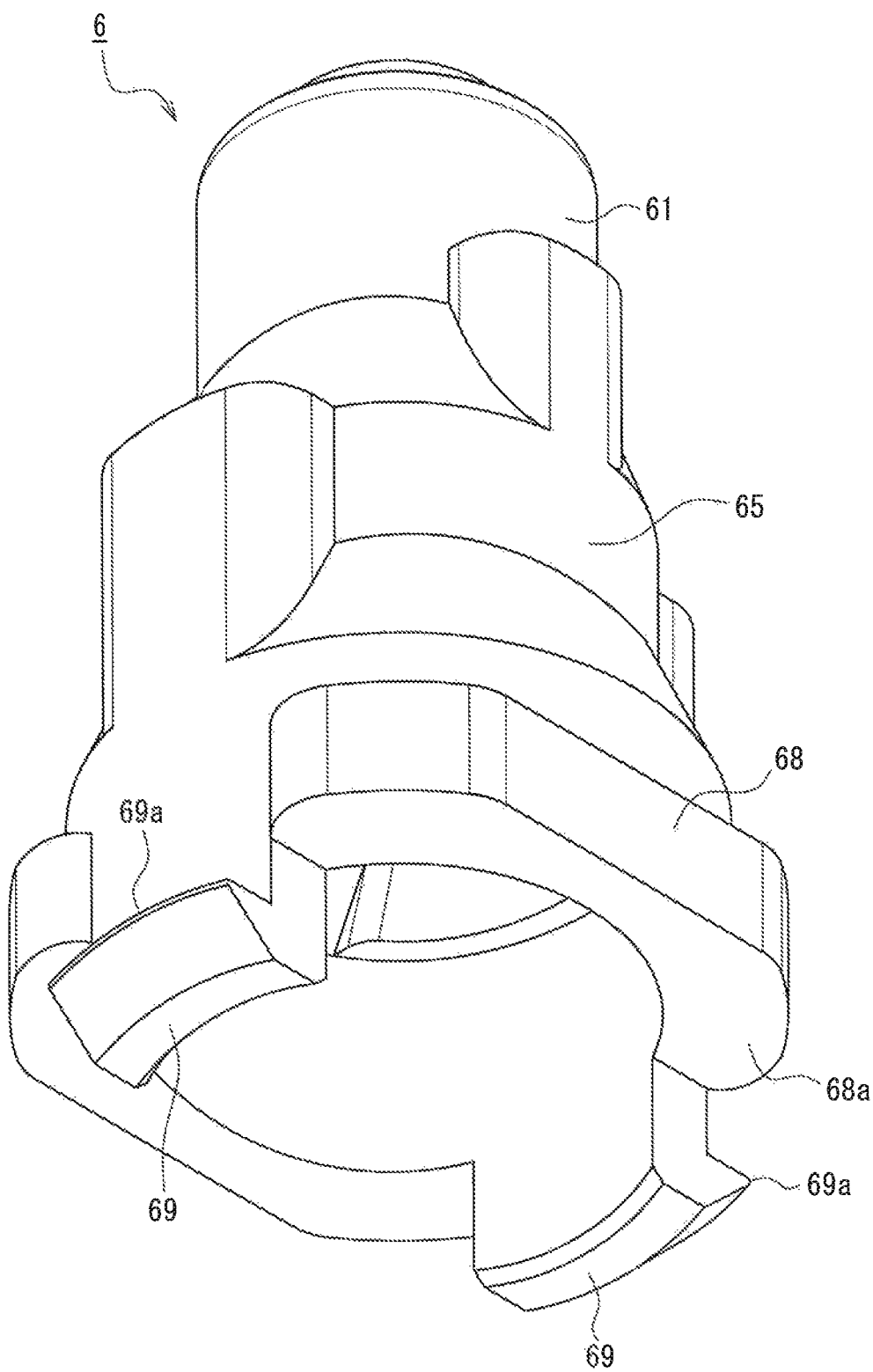
FIG. 3B is a perspective view of the shield when viewed from below.
Figure 3C:
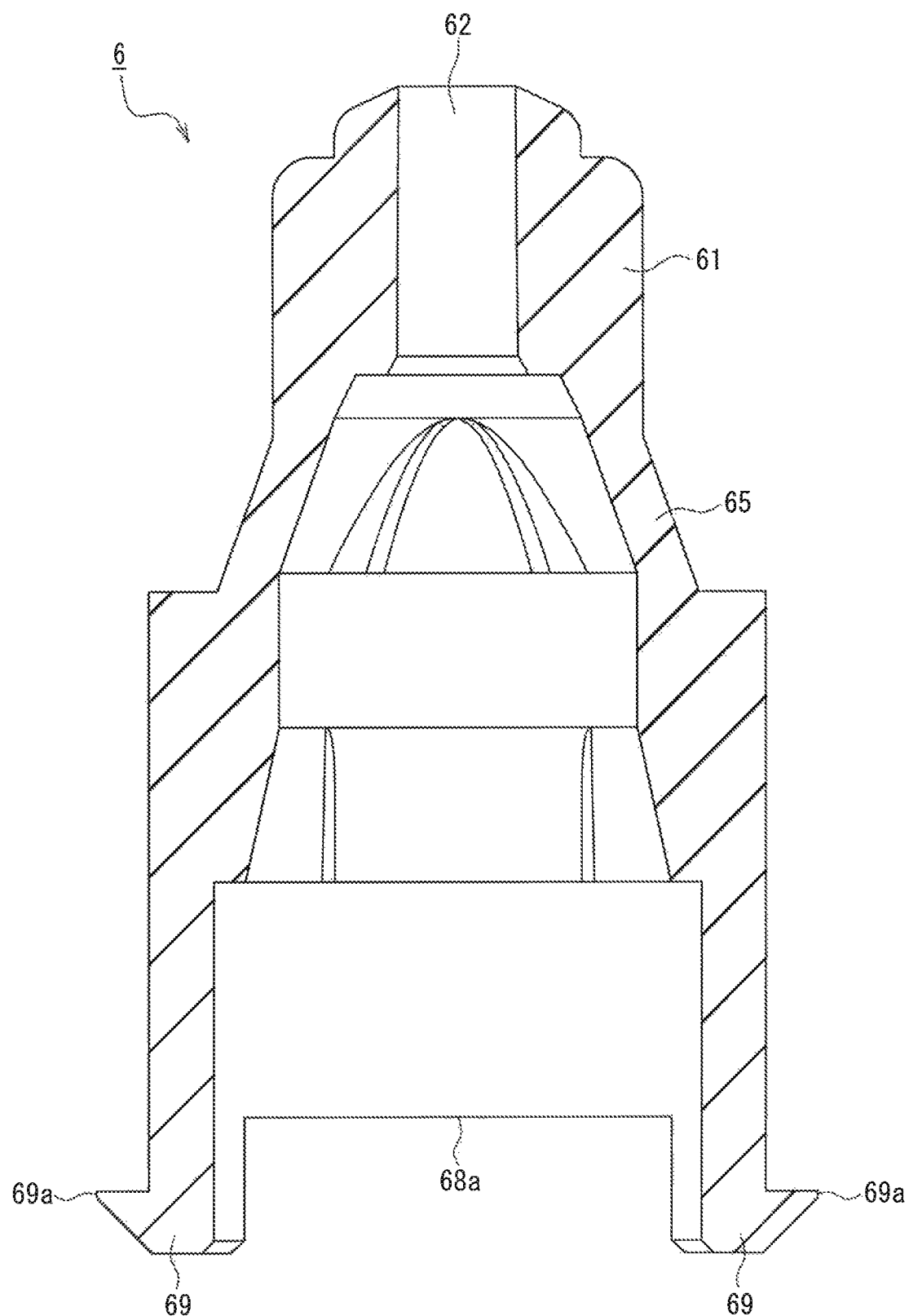
FIG. 3C is a cross-sectional view of the shield taken along a vertical plane.

The shield 6 that constitutes the male connector 2 will be described below. FIG. 3A is a perspective view of the shield 6 when viewed from above, FIG. 3B is a perspective view of the shield 6 when viewed from below, and FIG. 3C is a cross-sectional view of the shield. The shield 6 includes a head portion 61, an outer circumferential wall 65, and a base portion 68 in this order from the top to the bottom. As shown in FIG. 3C, the shield 6 has a substantially tubular shape having a space penetrating the shield 6 in the vertical direction.

The shield 6 is integrally formed as a single component using a soft material (so-called elastomer) having rubber elasticity (or flexibility). The material for the shield 6 is not limited, but, for example, isoprene rubber, silicone rubber, butyl rubber, a thermoplastic elastomer, and the like can be used.

As shown in FIG. 3C, a through hole 62 is formed penetrating the head portion 61 in the vertical direction. It is preferable that an inner circumferential surface of the through hole 62 has a shape that conforms to the outer circumferential surface of the male luer 10 so as to come into intimate contact with the outer circumferential surface of the male luer 10 of the connector main body 3. In the present embodiment, the inner circumferential surface of the through hole 62 constitutes a cylindrical tubular surface whose internal diameter is constant with respect to the vertical direction. It is preferable that the internal diameter of the through hole 62 is equal to or slightly smaller than the external diameter of the male luer 10 of the connector main body 3.

When a compressive force in the vertical direction is applied to the shield 6, the outer circumferential wall 65 is elastically compressively deformed such that its vertical dimension is reduced (see FIGS. 13D and 13E, which will be described later). As shown in FIG. 3C, the outer circumferential wall 65 has a larger internal diameter than the through hole 62 of the head portion 61. When the shield 6 is attached to the connector main body 3, the outer circumferential wall 65 is spaced apart from the male luer 10 in the radial direction (see FIGS. 5C and 5D, which will be described later). Thus, the likelihood of the inner circumferential surface of the outer circumferential wall 65 colliding with the male luer 10 when the outer circumferential wall 65 is compressively deformed in the vertical direction is reduced. This is advantageous in increasing the amount of compressive deformation of the outer circumferential wall 65 in the vertical direction.

Moreover, in the outer circumferential wall 65, tapered (conical) portions where the external and internal diameters of the outer circumferential wall 65 increase as the distance from the head portion 61 increases and cylindrical tubular portions where the external and internal diameters of the outer circumferential wall 65 are constant with respect to the vertical direction are alternatingly arranged in the vertical direction. Thus, the outer circumferential wall 65 as a whole has a conical shape that becomes gradually narrower toward the head portion 61. When a compressive force in the vertical direction is applied to the shield 6, this shape allows the outer circumferential wall 65 to deform such that the tapered portions are depressed into the cylindrical tubular portions directly under the respective tapered portions (see FIGS. 13D and 13E, which will be described later). This is advantageous in increasing the amount of compressive deformation of the outer circumferential wall 65 in the vertical direction.

The base portion 68 has a flat bottom surface 68a. A pair of fixing projections 69 protrude downward from the bottom surface 68a. A fixing claw 69a protrudes outward from an outer circumferential surface of each fixing projection 69. The fixing projections 69 and the fixing claws 69a are used to fix the shield 6 to the connector main body 3.

1. 3. Lock Ring

Figure 4A:
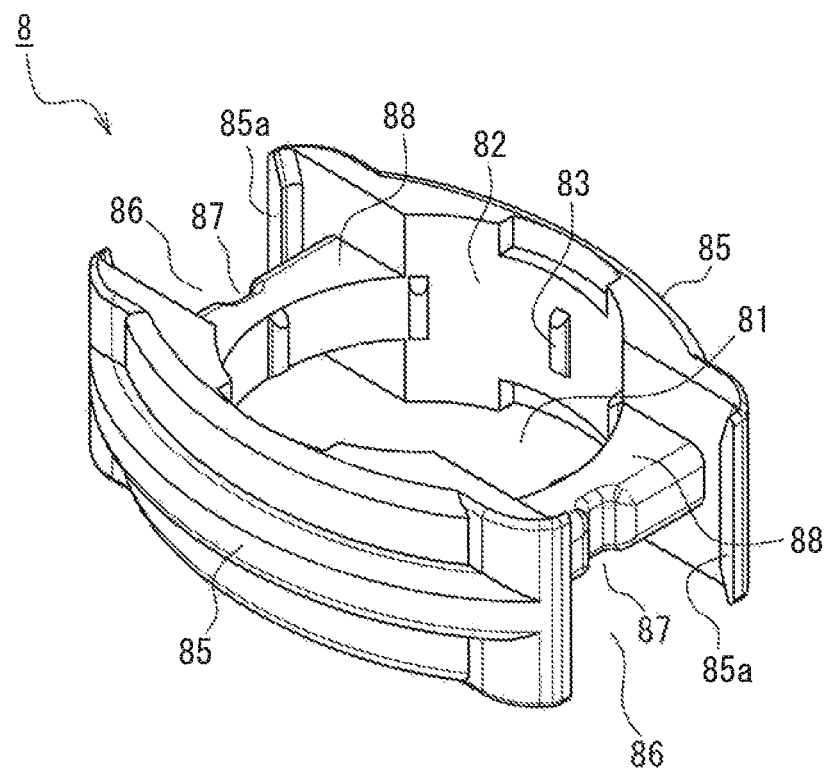
FIG. 4A is a perspective view of a lock ring according to the embodiment of the present invention when viewed from above.
Figure 4B:
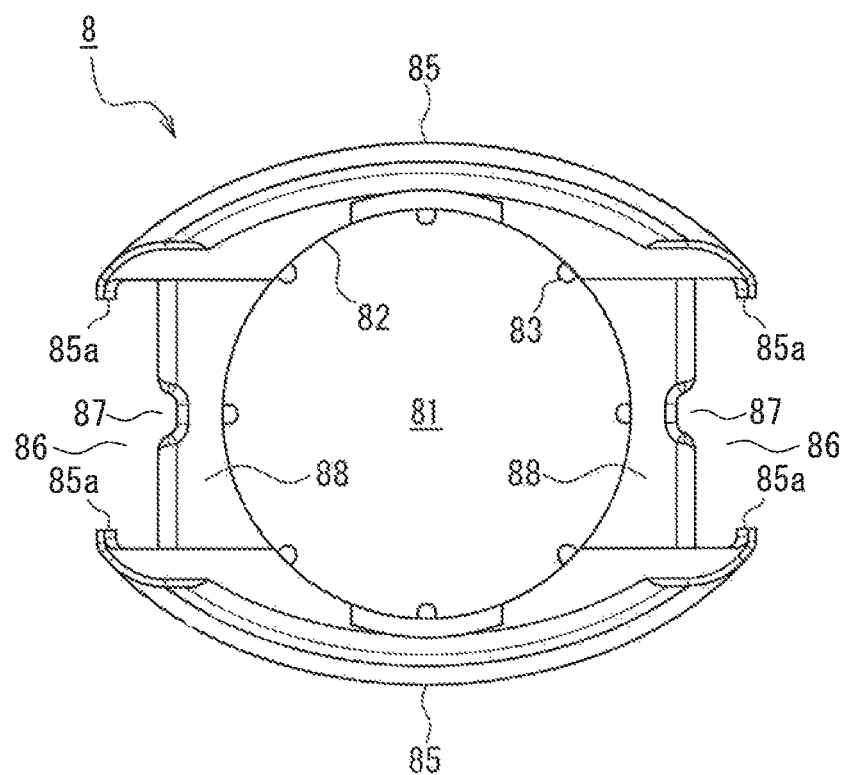
FIG. 4B is a plan view of the lock ring.

The lock ring 8 that constitutes the male connector 2 will be described below. FIG. 4A is a perspective view of the lock ring 8 when viewed from above, and FIG. 4B is a plan view of the lock ring 8.

The lock ring 8 has an annular shape in which a circular opening 81 is formed at the center. An inner circumferential surface 82 that surrounds the opening 81 constitutes a cylindrical tubular surface. A plurality of ribs 83 protrude from the inner circumferential surface 82 toward the inside of the opening 81. The ribs 83 extend along the vertical direction. In the present embodiment, the number of ribs 83 is eight; however, the present invention is not limited to this, and the number of ribs 83 may also be more than eight or less than eight. In the case where two or more ribs 83 are provided, preferably the ribs 83 are arranged at regular intervals in the circumferential direction.

The lock ring 8 includes a pair of arch-shaped portions 85 that are arranged opposing each other. A pair of bridging portions 88 couple the pair of arch-shaped portions 85 to each other. As shown in FIG. 4B, when the lock ring 8 is viewed from above (in plan view), outer surfaces of the arch-shaped portions 85 conform to a substantially elliptical shape that is almost the same as the substantially elliptical outline (see FIG. 2E) of the connector main body 3 in plan view. The arch-shaped portions 85 are disposed on the minor axis of the above-described elliptical shape. The bridging portions 88 are disposed on the major axis of the above-described ellipse and at respective positions that are individually shifted inward from the above-described ellipse. In other words, the substantially elliptical shape is cut out using a pair of cut-outs 86 that are provided on the major axis thereof. The surface of each bridging portion 88 that faces outward constitutes a flat surface that is parallel to the vertical direction. A groove 87 extending along the vertical direction is formed in this flat surface.

Sliding ribs 85a protrude from both ends of each arch-shaped portion 85 toward the opposing arch-shaped portion 85. The sliding ribs 85a extend along the vertical direction.

The lock ring 8 has two-fold rotational symmetry (when rotated 180 degrees, the lock ring 8 coincides with its state prior to rotation). Although omitted from the drawings, even if the lock ring 8 is inverted, the lock ring 8 has the same shape.

It is preferable that the lock ring 8 is made of a hard material. Specifically, a resin material such as polyacetal, polycarbonate, polystyrene, polyamide, polypropylene, or rigid polyvinyl chloride may be used. The lock ring 8 can be integrally produced as a single component through injection molding or the like using such a resin material.

1.4. Assembling of Male Connector

Figure 5A:
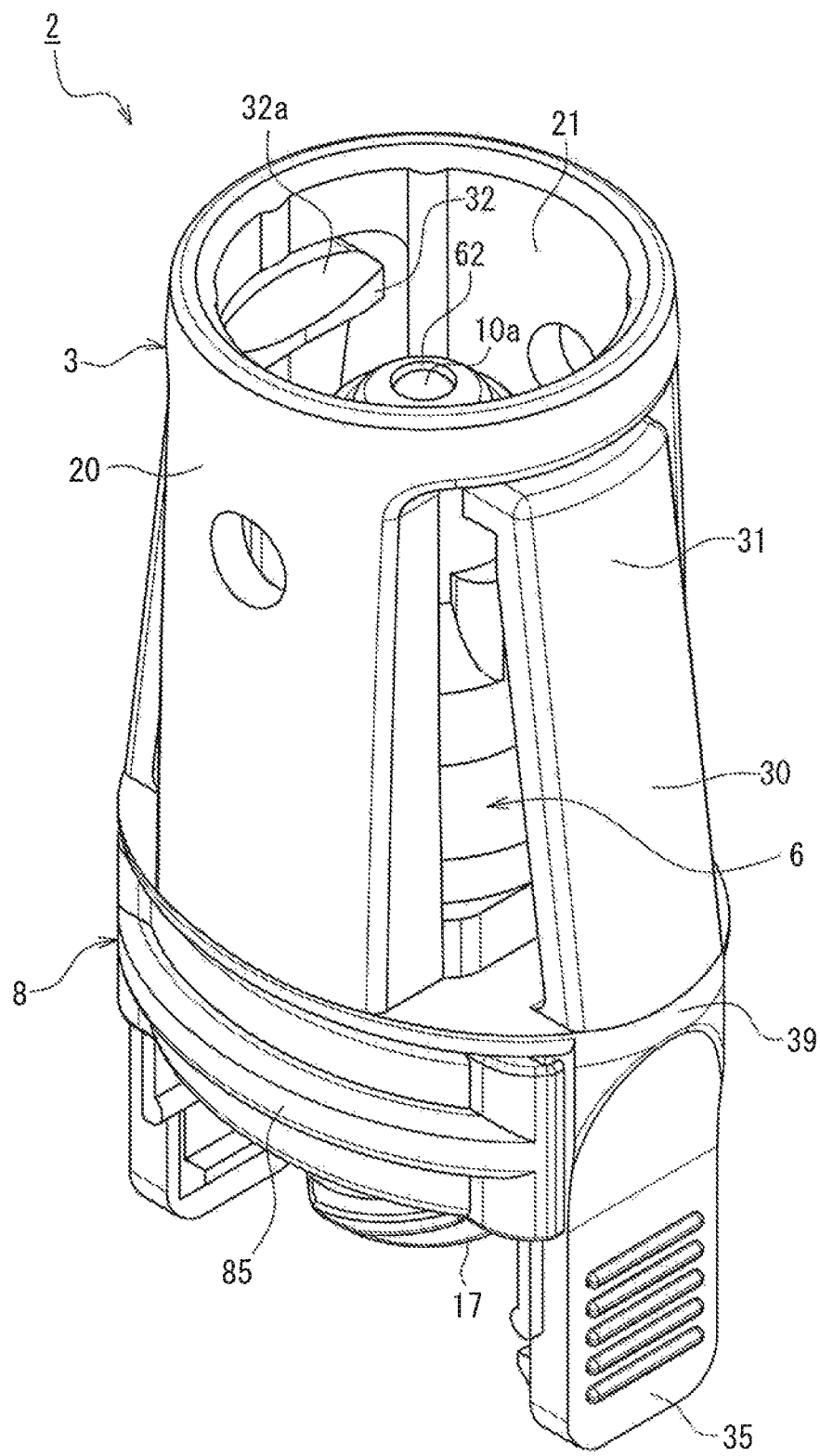
FIG. 5A is a perspective view of a lever lock male connector according to the embodiment of the present invention when viewed from above.
Figure 5B:
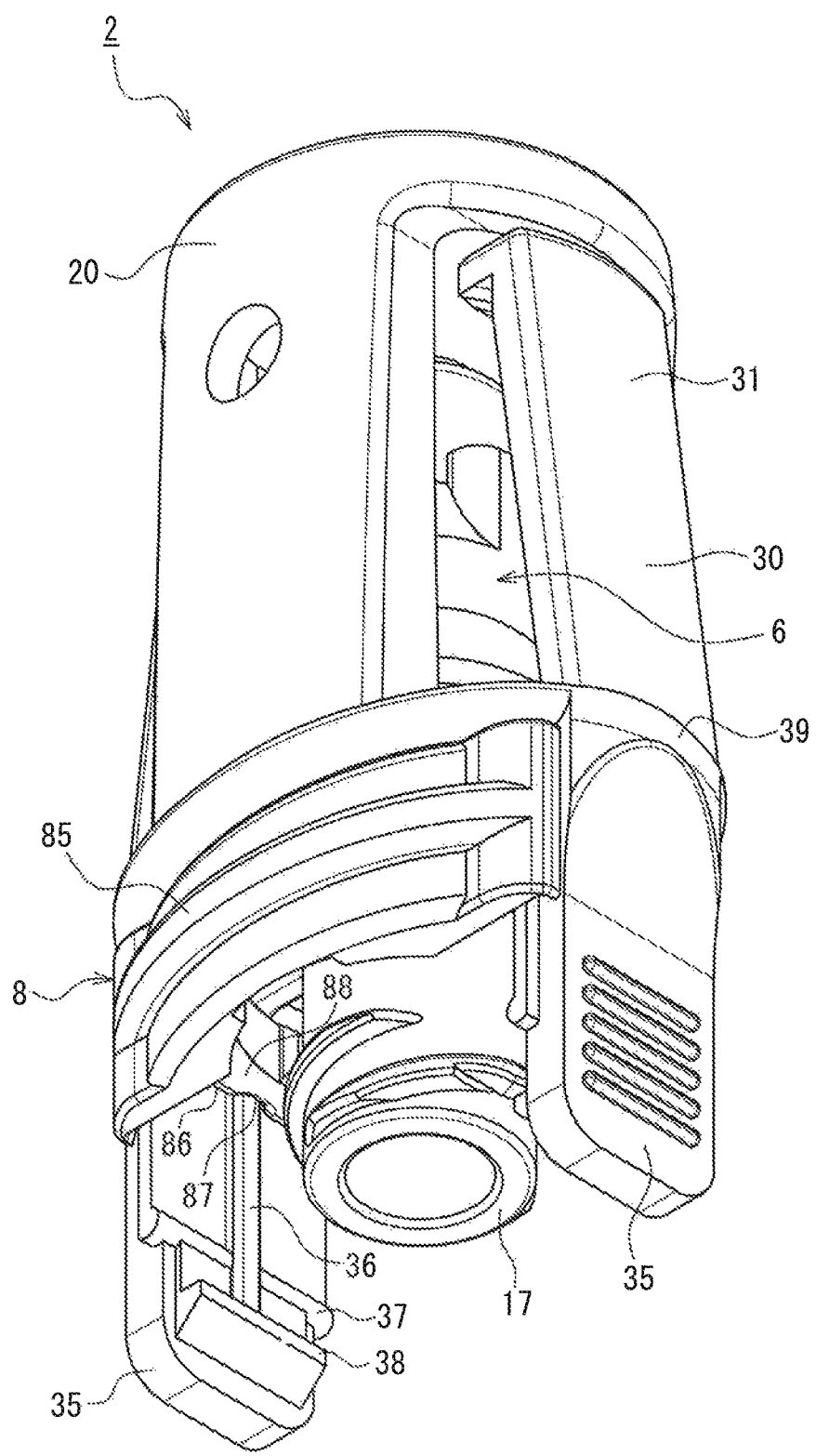
FIG. 5B is a perspective view of the lever lock male connector when viewed from below.
Figure 5C:
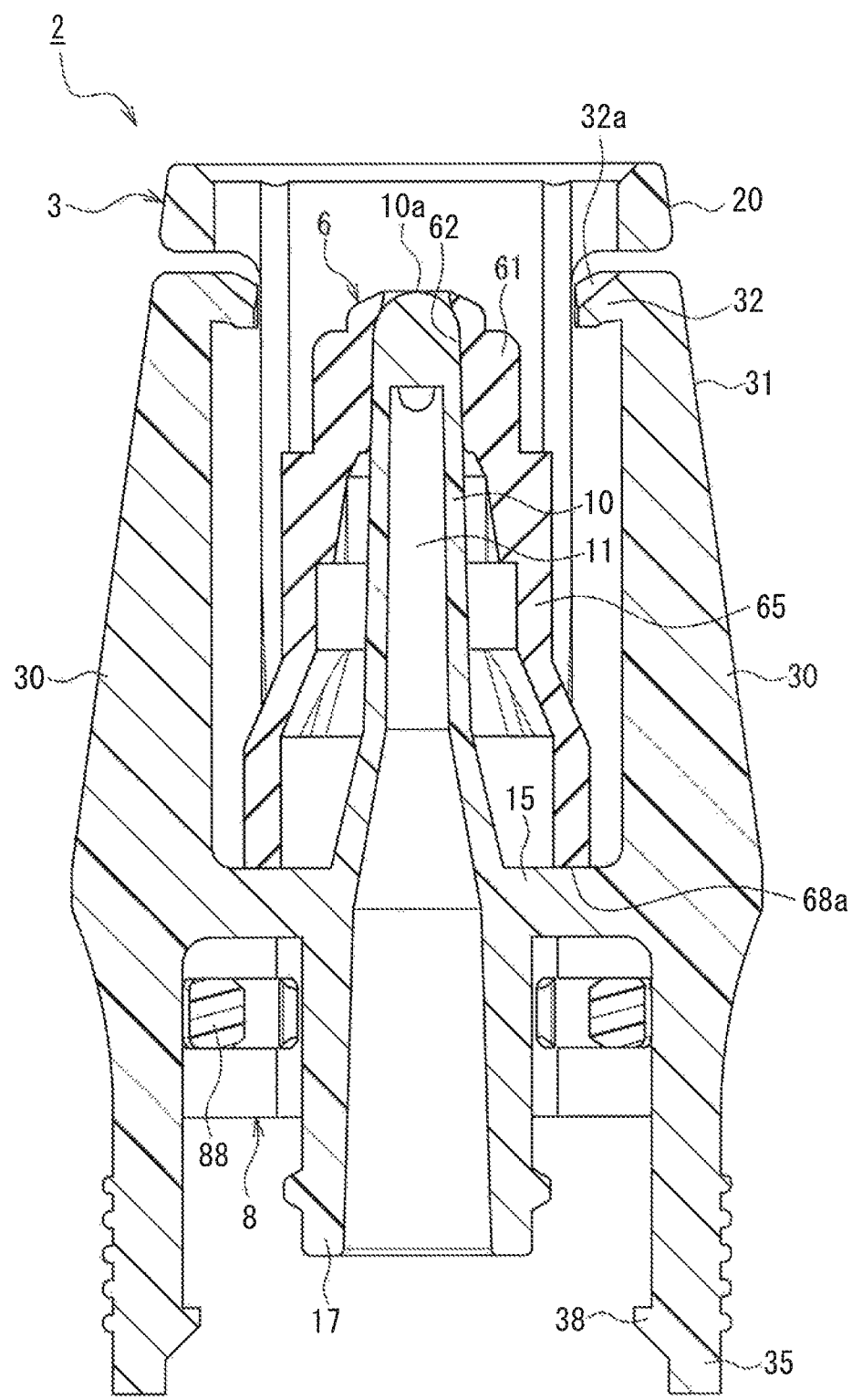
FIG. 5C is a cross-sectional view of the lever lock male connector.
Figure 5D:
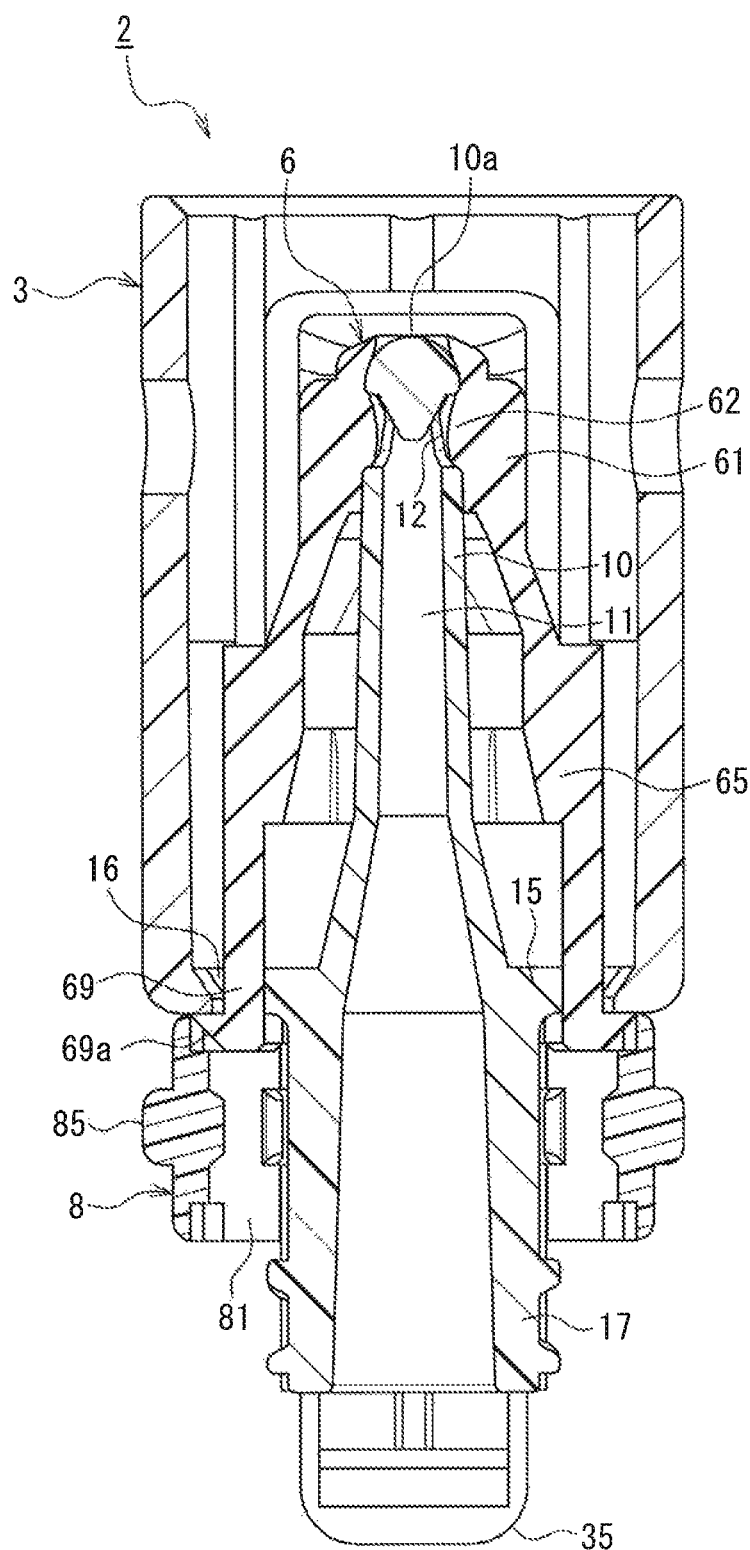
FIG. 5D is a cross-sectional view of the lever lock male connector taken along another plane.

As shown in FIG. 1, the shield 6 is inserted into the hood 20 from above the connector main body 3. Also, the lock ring 8 is inserted between the pair of operating portions 35 from below the connector main body 3. FIG. 5A is a perspective view of the male connector 2 when viewed from above, with the shield 6 and the lock ring 8 attached to the connector main body 3, and FIG. 5B is a perspective view of the male connector 2 when viewed from below. FIG. 5C is a cross-sectional view of the male connector 2 taken along a plane containing the central axis 3a and the major axis 15a, and FIG. 5D is a cross-sectional view of the male connector 2 taken along a plane containing the central axis 3a and the minor axis 15b. A plan view of the male connector 2 is not given because it is the same as that shown in FIG. 2E except that the shield 6 is provided.

As shown in FIG. 5D, the fixing projections 69 of the shield 6 are inserted in the respective holes 16 that are provided in the base 15 of the connector main body 3. The fixing claws 69a have passed through the holes 16 and are engaged with a lower surface of the base 15. The bottom surface 68a of the shield 6 is in intimate contact with an upper surface of the base 15 (FIG. 5C).

The leading end 10a and its neighboring portion of the male luer 10 are inserted into the through hole 62 of the head portion 61 of the shield 6. The leading end 10a of the male luer 10 is exposed in the through hole 62 of the head portion 61. The inner circumferential surface of the through hole 62 appropriately deforms in accordance with the external shape of the outer circumferential surface of the male luer 10 and is in intimate contact with that outer circumferential surface. The openings of the lateral holes 12 of the male luer 10 are closed off in a liquid-tight manner by the inner circumferential surface of the through hole 62.

The outer circumferential wall 65 of the shield 6 is spaced apart from the male luer 10 in the radial direction. Thus, a liquid-tight space is formed between the shield 6 and the connector main body 3. Moreover, the outer circumferential wall 65 is spaced apart from both the hood 20 and the levers 30 in the radial direction.

As shown in FIG. 5B, the tubular portion 17 of the connector main body 3 is inserted into the opening 81 of the lock ring 8 (see FIG. 4A). The operating portions 35 of the connector main body 3 are fitted in the respective cut-outs 86 of the lock ring 8 (see FIG. 4A). Furthermore, the ribs 36 provided on the operating portions 35 are fitted in the respective grooves 87 provided in the bridging portions 88. Thus, the lock ring 8 is not rotatable relative to the connector main body 3.

On the other hand, the lock ring 8 is movable in the vertical direction in a state in which it is held between the pair of operating portions 35 as described above. Upward movement of the lock ring 8 is restricted by the lock ring 8 colliding with the lower surface of the base 15. Downward movement of the lock ring 8 is restricted by the lock ring 8 colliding with the stopping projections 38 provided on the operating portions 35. FIGS. 5A to 5D show a state in which the lock ring 8 has been moved uppermost (highest position).

When the lock ring 8 is at its highest position, the sliding ribs 85a (see FIGS. 4A and 4B) of the lock ring 8 abut against the pressure contact ribs 35b (see FIG. 2B) of the operating portions 35a in the direction of the major axis 15a (FIG. 2E). The frictional force between the sliding ribs 85a and the pressure contact ribs 35b prevents the lock ring 8 from being lowered from the highest position due to gravity, vibrations, and the like. That is to say, the pressure contact ribs 35b abutting against the lock ring 8 constitute a "first movement prevention mechanism" that prevents the lock ring 8 at its highest position from being unintentionally lowered. Since the lock ring 8 is held at its highest position, the ease of operations for connecting and disconnecting the male connector 2 (FIGS. 5A to 5D) to and from the screw lock connector 100 (FIGS. 8A and 8B) (the details of which will be described later) and the ease of operations for connecting and disconnecting the male connector assembly 1 (FIGS. 9A and 9B) to and from a female connector 200 (FIGS. 10A and 10B) (the details of which will be described later) do not deteriorate.

In the present invention, a state in which, as shown in FIGS. 5A to 5D, substantially no external force acts on the levers 30, the shield 6 is not compressively deformed in the vertical direction, and the lock ring 8 has been moved to the highest position is referred to as the "initial state" of the male connector 2.

2. Screw Lock Connector 2. 1. Luer Main Body

Figures 6A, 6B:
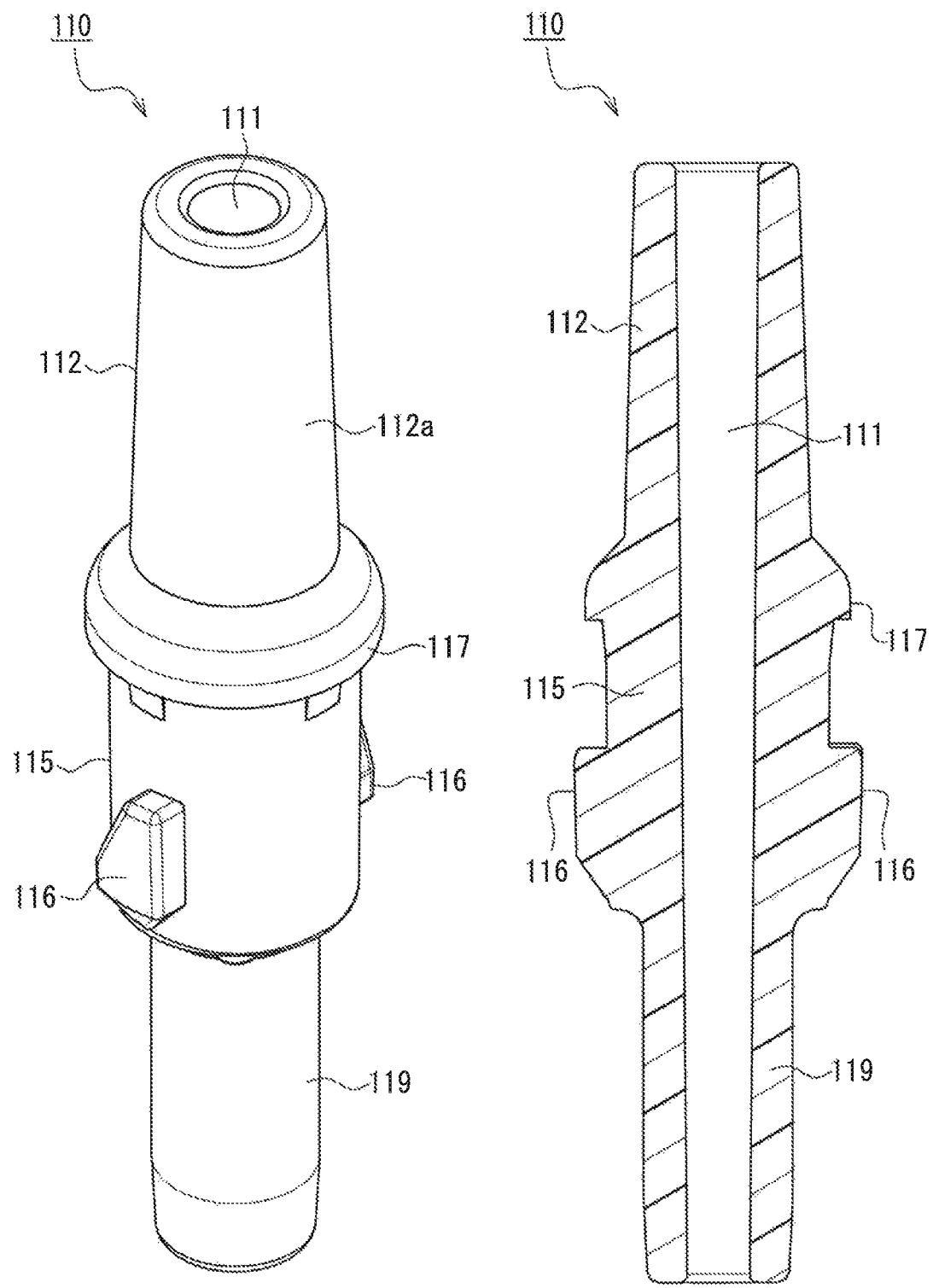
FIG. 6A is a perspective view of a luer main body according to the embodiment of the present invention.
FIG. 6B is a cross-sectional view of the luer main body.

The luer main body 110 that constitutes the screw lock connector 100 will be described below. FIG. 6A is a perspective view of the luer main body 110, and FIG. 6B is a cross-sectional view of the luer main body 110.

The luer main body 110 has a substantially cylindrical tubular shape as a whole, in which a through hole (flow channel) 111 along the longitudinal direction of the luer main body 110 is formed. The luer main body 110 includes a male luer 112, a tubular portion 115, and a connecting portion 119 in this order from the top to the bottom.

An outer circumferential surface 112a of the male luer 112 constitutes a male tapered surface (e.g., a 6% tapered surface) whose external diameter gradually decreases toward the leading end. An outer circumferential surface of the tubular portion 115 constitutes a cylindrical tubular surface whose external diameter is constant with respect to the vertical direction. A pair of protruding portions 116 protrude outward from the outer circumferential surface of the tubular portion 115. An annular projection 117 continuously extending in the circumferential direction is provided at the boundary between the male luer 112 and the tubular portion 115. The annular projection 117 has an external diameter that is larger than those of the male luer 112 and the tubular portion 115.

It is preferable that the luer main body 110 is made of a hard material. Specifically, a resin material such as polyacetal, polycarbonate, polystyrene, polyamide, polypropylene, or rigid polyvinyl chloride may be used. The luer main body 110 can be integrally produced as a single component through injection molding or the like using such a resin material.

2. 2. Lock Nut

Figure 7A:
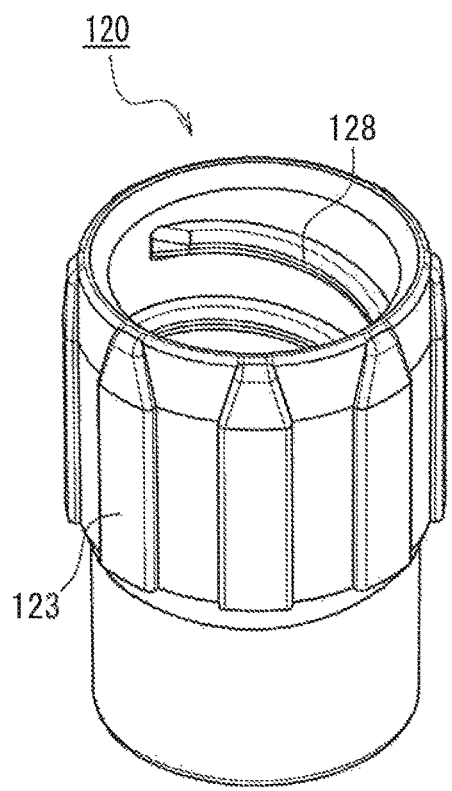
FIG. 7A is a perspective view of a lock nut according to the embodiment of the present invention when viewed from above.
Figure 7B:
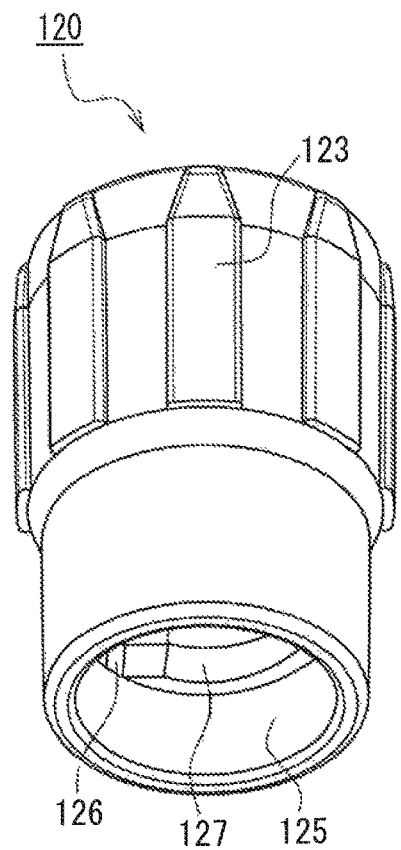
FIG. 7B is a perspective view of the lock nut when viewed from below.
Figure 7C:
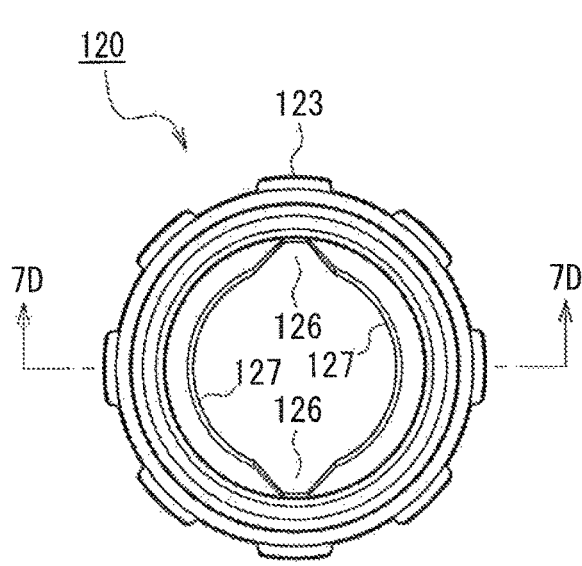
FIG. 7C is a plan view of the lock nut.
Figure 7D:
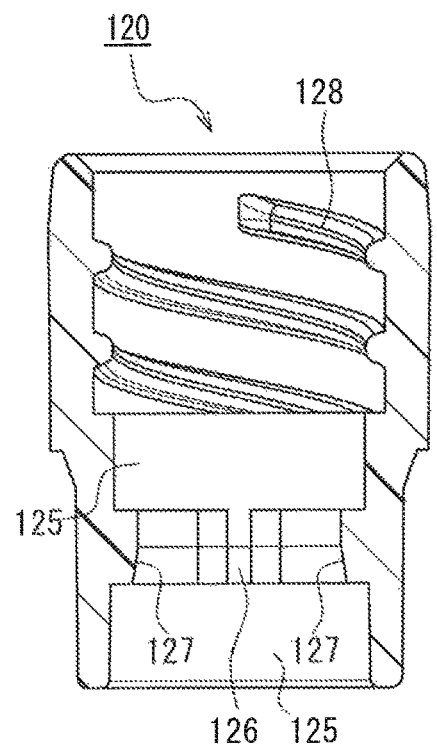
FIG. 7D is a cross-sectional view of the lock nut taken along a vertical plane containing line 7D-7D in FIG. 7C.

The lock nut 120 that constitutes the screw lock connector 100 will be described below. FIG. 7A is a perspective view of the lock nut 120 when viewed from above, FIG. 7B is a perspective view of the lock nut 120 when viewed from below, FIG. 7C is a plan view of the lock nut 120, and FIG. 7D is a cross-sectional view of the lock nut 120. The lock nut 120 has a hollow, substantially cylindrical tubular shape as a whole.

The outer circumferential surface of the lock nut 120 is constituted by two cylindrical tubular surfaces having different external diameters. A plurality of ribs 123 protrude outward from the upper cylindrical tubular surface having a relatively large external diameter. The ribs 123 extend along the vertical direction. In the present embodiment, the number of ribs 123 is eight; however, the present invention is not limited to this, and the number of ribs 123 may be more than eight or less than eight. In the case where two or more ribs 123 are provided, preferably the ribs 83 are arranged at regular intervals in the circumferential direction. In the present embodiment, the outer circumferential surface of the lock nut 120 is constituted by the two cylindrical tubular surfaces; however, the present invention is not limited to this. For example, the entire outer circumferential surface from the upper end to the lower end may be constituted by a single cylindrical tubular surface. Alternatively, the outer circumferential surface may contain a surface (e.g., a polygonal prism-shaped surface) other than a cylindrical tubular surface.

A female thread 128 is formed on an inner circumferential surface of the lock nut 120, the female thread 128 extending in a region from an upper end to the substantially middle of the inner circumferential surface of the lock nut 120. A portion of the inner circumferential surface of the lock nut 120 that is located below the female thread 128 constitutes a cylindrical tubular surface 125 having a constant internal diameter. A position-restricting projection 127 extending in the circumferential direction protrudes from the cylindrical tubular surface 125. A pair of guide passages 126 are formed in the position-restricting projection 127. The guide passages 126 extend in the vertical direction. The guide passages 126 divide the position-restricting projection 127 in the circumferential direction.

It is preferable that the lock nut 120 is made of a hard material. Specifically, a resin material such as polyacetal, polycarbonate, polystyrene, polyamide, polypropylene, or rigid polyvinyl chloride may be used. The lock nut 120 can be integrally produced as a single component through injection molding or the like using such a resin material.

2. 3. Assembling of Screw Lock Connector

As shown in FIG. 1, the flexible tube 190 is passed through the lock nut 120. Then, the connecting portion 119 of the luer main body 110 is inserted into an upper end of the tube 190. Subsequently, the lock nut 120 is moved upward. The luer main body 110 is inserted into the inside of the female thread 128 of the lock nut 120. The protruding portions 116 protruding from the outer circumferential surface of the luer main body 110 may possibly collide with the position-restricting projection 127 protruding from the inner circumferential surface of the lock nut 120. If this is the case, the lock nut 120 is slightly rotated relative to the luer main body 110. When the positions of the protruding portions 116 of the luer main body 110 with respect to the circumferential direction coincide with the positions of the respective guide passages 126 of the lock nut 120 with respect to the circumferential direction, the protruding portions 116 can pass through the guide passages 126. In this manner, the screw lock connector 100 can be assembled as shown in FIGS. 8A and 8B.

As shown in FIG. 8B, the position-restricting projection 127 of the lock nut 120 is located between the annular projection 117 and the protruding portions 116 of the luer main body 110. Due to the position-restricting projection 127 colliding with the annular projection 117 and the protruding portions 116, the lock nut 120 is restricted from moving upward (toward the tapered surface 112) and downward (toward the connecting portion 119) relative to the luer main body 110. However, the lock nut 120 can freely rotate around the luer main body 110.

3. Connection of Male Connector and Screw Lock Connector (Assembling of Male Connector Assembly)

The male connector 2 (FIGS. 5A to 5D) and the screw lock connector 100 (FIGS. 8A and 8B) can be connected to each other by inserting the male luer 112 of the luer main body 110 into the tubular portion 17 of the connector main body 3 and screwing the female thread 128 of the lock nut 120 onto the male thread 18 of the tubular portion 17.

Figure 9A:
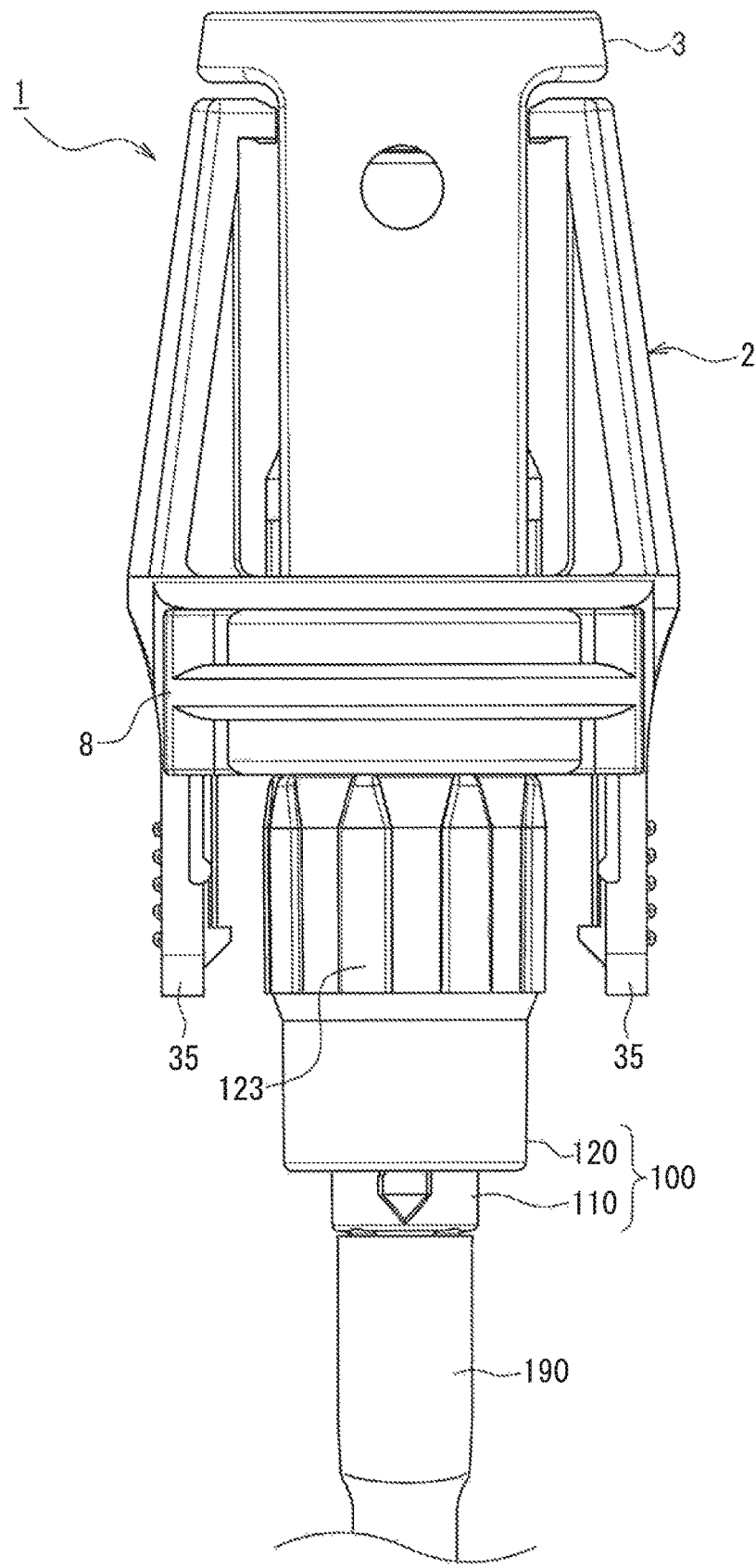
FIG. 9A is a side view of a male connector assembly according to the embodiment of the present invention.
Figure 9B:
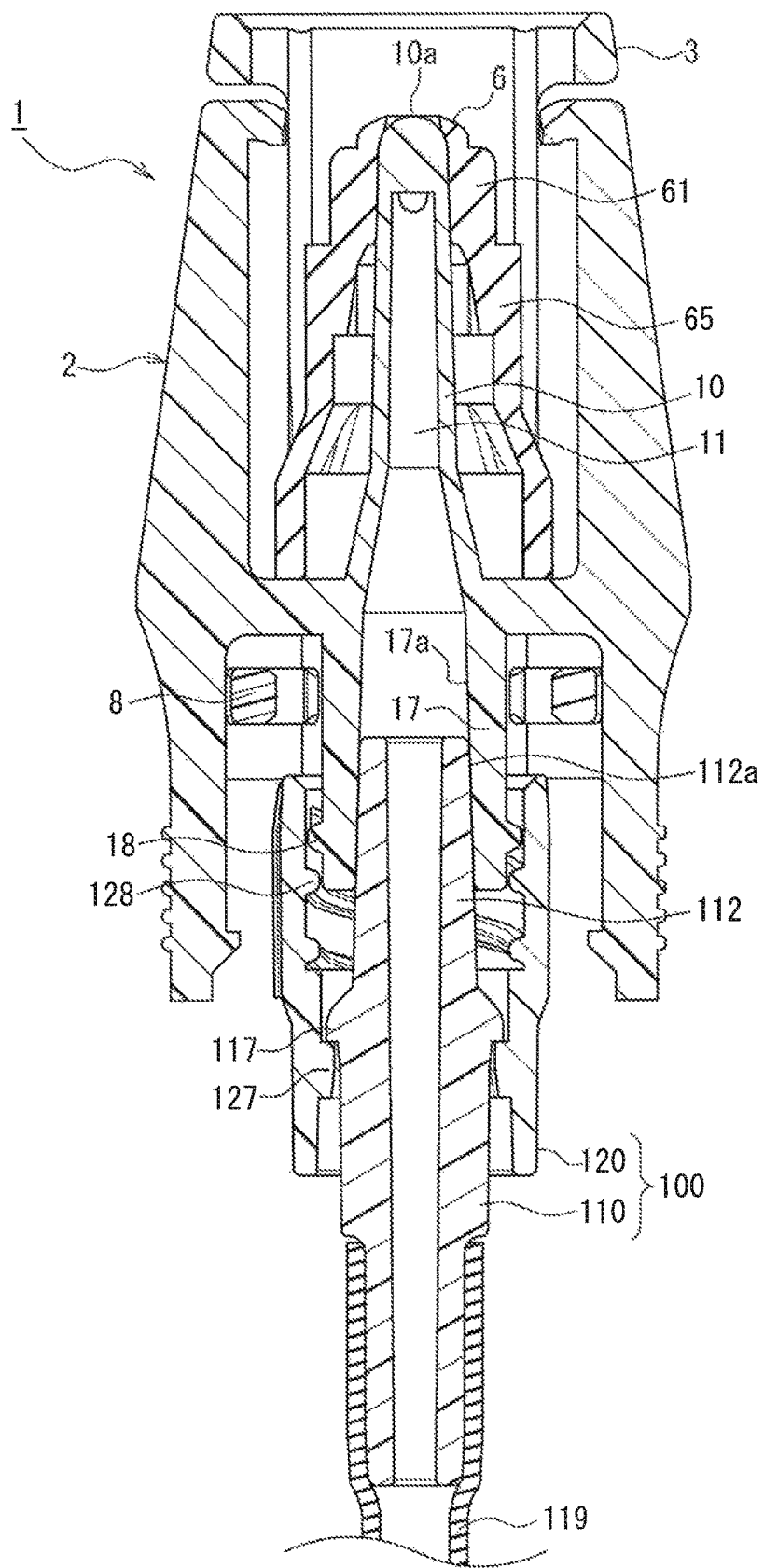
FIG. 9B is a cross-sectional view of the male connector assembly.

FIG. 9A is a side view of the male connector assembly 1 that is obtained by connecting the male connector 2 and the screw lock connector 100 to each other, and FIG. 9B is a cross-sectional view of the male connector assembly 1.

The outer circumferential surface 112a of the male luer 112 and the inner circumferential surface 17a of the tubular portion 17 are the tapered surfaces having the same diameter and taper angle. Accordingly, as shown in FIG. 9B, the outer circumferential surface 112a and the inner circumferential surface 17a come into intimate contact with each other in a liquid-tight manner. Thus, the tube 190 and the flow channel 11 of the male luer 10 are in communication with each other.

The female thread 128 of the lock nut 120 and the male thread 18 of the tubular portion 17 are screwed together. Moreover, the position-restricting projection 127 of the lock nut 120 and the annular projection 117 of the luer main body 110 are engaged with each other. Thus, the male luer 112 and the tubular portion 17 are securely connected to each other. Even when an unintentional pull force acts between the male connector 2 (or the connector main body 3) and the screw lock connector 100 (or the luer main body 110), the male connector 2 and the screw lock connector 100 will not be disconnected from each other.

As shown in FIG. 9A, the lock nut 120 is disposed between the pair of operating portions 35. In the initial state in which the lock ring 8 has been moved to its highest position, the lock nut 120 is located below the lock ring 8. Therefore, it is possible to rotate the lock nut 120 while using the ribs 123, which are formed on the outer circumferential surface of the lock nut 120, as an anti-slipping structure, to screw or unscrew the female thread 128 onto or from the male thread 18.

4. Method of Use 4. 1. Female Connector

The male connector assembly 1 is used connected to a female connector.

Figure 10A:
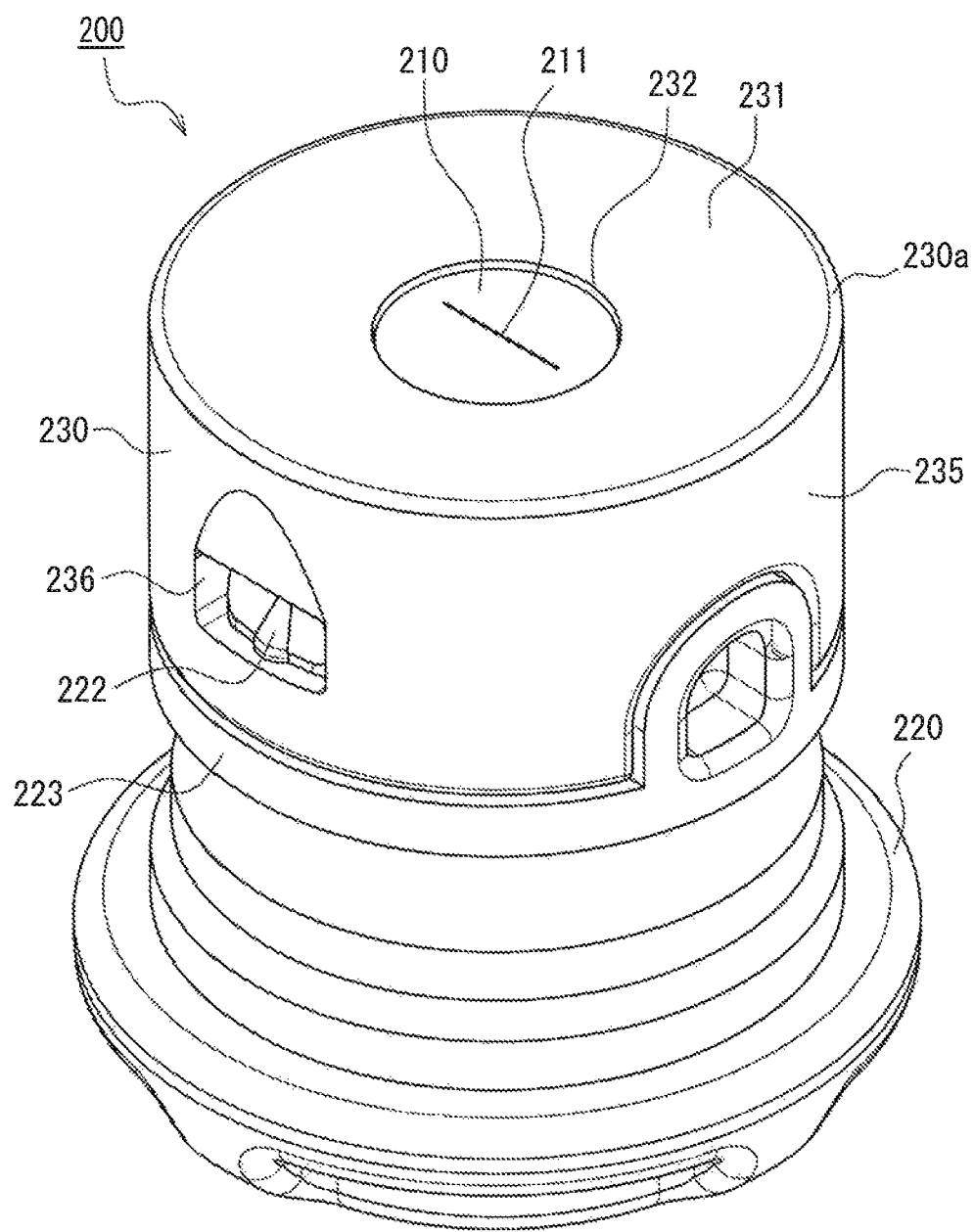
FIG. 10A is a perspective view of an example of a female connector to which the male connector assembly according to the embodiment of the present invention is connectable.
Figure 10B:
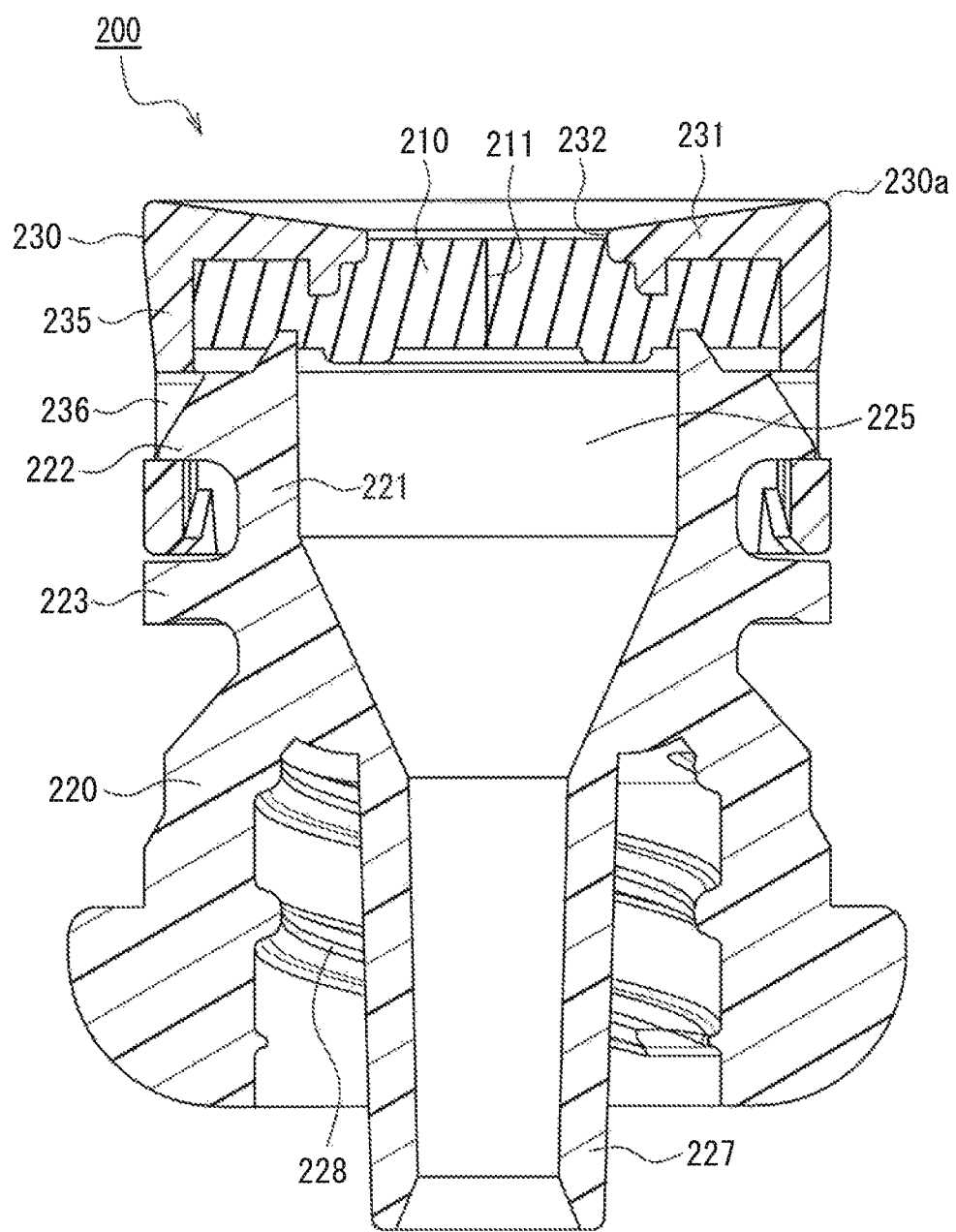
FIG. 10B is a cross-sectional view of the female connector.

FIGS. 10A and 10B show an example of the female connector. FIG. 10A is a perspective view of the female connector 200, and FIG. 10B is a cross-sectional view of the female connector 200.

The female connector 200 includes the circular plate-shaped partition member (hereinafter referred to as "septum") 210 as well as a mount 220 and a cap 230 that sandwich and fix the septum 210 in the vertical direction.

A straight line-shaped slit (cut portion) 211 penetrating the septum 210 in the vertical direction is formed at the center of the septum 210. The material for the septum 210 is not limited, but a soft material having rubber elasticity is preferable, and for example, isoprene rubber, silicone rubber, butyl rubber, a thermoplastic elastomer, and the like can be used.

The mount 220 includes, in an upper portion thereof, a seat 221 having a substantially cylindrical tubular shape. An outer circumferential surface of the seat 221 constitutes a cylindrical tubular surface. A pair of engagement claws 222 and an annular projection 223 protrude outward form the outer circumferential surface of the seat 221. The annular projection 223 is slightly spaced downward from the engagement claws 222.

A male luer 227 that is in communication with a cavity 225 in the seat 221 and a female thread 228 that is coaxial with the male luer 227 are provided below the seat 221. An outer circumferential surface of the male luer 227 constitutes a male tapered surface (conical surface) whose external diameter decreases as the distance to the leading end decreases (that is, as the distance from the seat 221 increases).

The cap 230 includes a top plate 231 having a circular plate-like shape, and a peripheral wall 235 extending downward from an outer circumferential end edge of the top plate 231 and having a cylindrical tubular shape. A circular opening (through hole) 232 is formed at the center of the top plate 231. A pair of engagement holes 236 are formed in the peripheral wall 235. The engagement holes 236 are through holes that penetrate the peripheral wall 235 in the radial direction.

As shown in FIG. 10B, the septum 210 is placed on the upper end of the seat 221, and the septum 210 is covered with the cap 230 from above. The engagement claws 222 formed on the seat 221 are fitted into the respective engagement holes 236 formed in the cap 230, and thus, the cap 230 is engaged with the engagement claws 222. As a result, the cap 230 is fixed to the mount 220 (see FIG. 10A). The septum 210 is sandwiched between the upper end of the seat 221 and the top plate 231 of the cap 230 in the thickness direction (i.e., vertical direction). The slit 211 of the septum 210 is exposed in the opening 232 that is formed in the top plate 231. The annular projection 223 formed on the mount 220 is located below and adjacent to the peripheral wall 235 of the cap 230. A top surface of the annular projection 223 constitutes a cylindrical tubular surface that is substantially the same as the outer circumferential surface of the peripheral wall 235.

The female connector 200 including the septum 210 in which the slit 211 is formed is generally called a needleless port.

4. 2. Connection and Disconnection of Male Connector Assembly and Female Connector The male connector assembly 1 and the female connector 200 can be connected to each other in the following manner.

Figure 11:
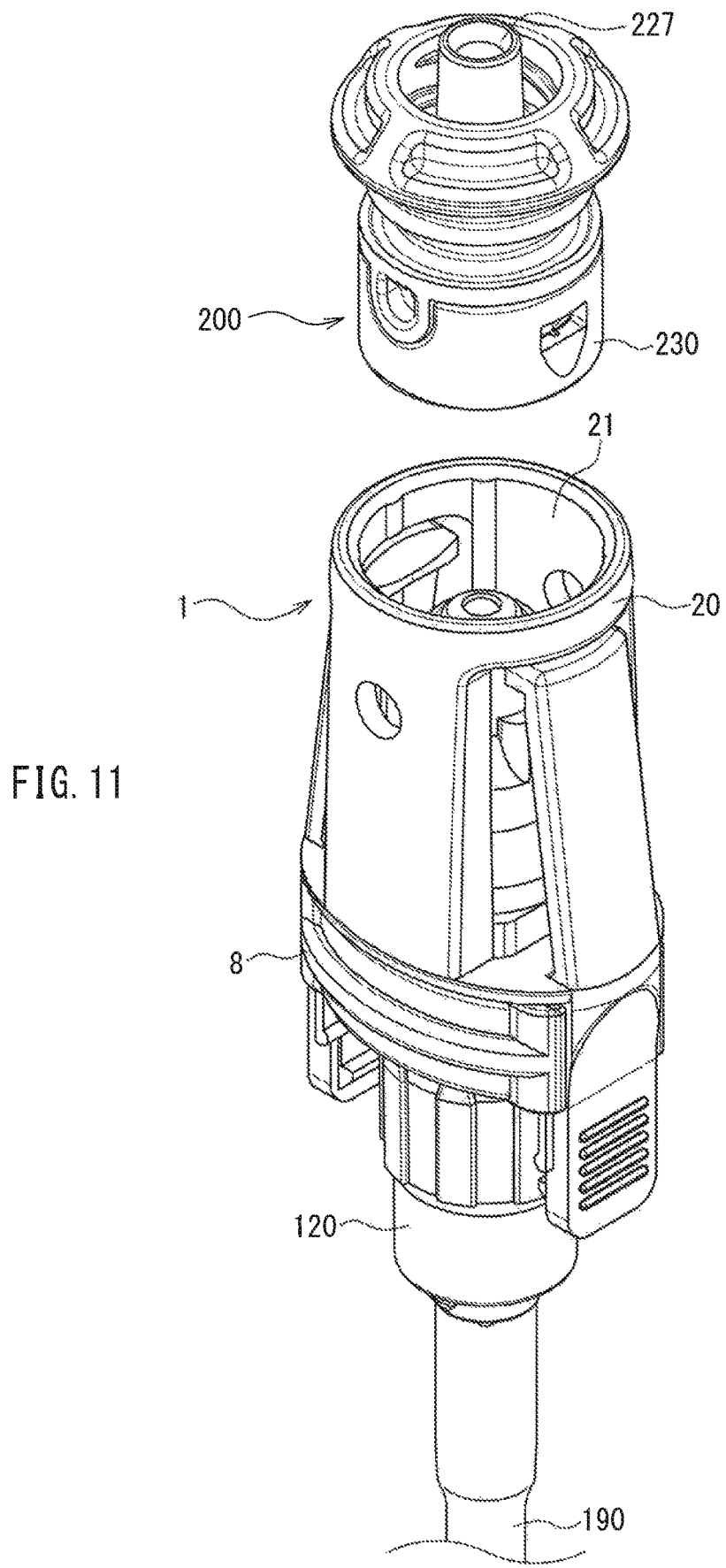
FIG. 11 is a perspective view of the male connector assembly according to the embodiment of the present invention immediately prior to being connected to the female connector.

First, as shown in FIG. 11, the male connector assembly 1 and the female connector 200 are placed opposing each other. Although not shown in the drawings, a flexible tube is connected to the male luer 227 of the female connector 200 directly or indirectly via a certain member.

From the state shown in FIG. 11, the male connector assembly 1 and the female connector 200 are brought close to each other. The cap 230 is inserted into the hood 20 and pushed further inward.

An outer end edge 230a (see FIGS. 10A and 10B) of the top plate 231 of the cap 230 abuts against the inclined surfaces 32a (see FIGS. 2F, 5A, and 5C) of the locking claws 32 of the levers 30. While sliding on the inclined surfaces 32a, the end edge 230a elastically displaces the levers 30 so as to move the locking claws 32 away from the male luer 10. Subsequently, the locking claws 32 slide on the peripheral wall 235 of the cap 230.

In parallel with this, the leading end 10a (see FIG. 9B) of the male luer 10 abuts against the septum 210 (see FIGS. 10A and 10B) that is exposed in the opening 232 of the cap 230, and subsequently advances into the slit 211 while deforming the septum 210. Almost simultaneously, the head portion 61 of the shield 6 abuts against the septum 210 or the top plate 231 of the cap 230. As the male luer 10 advances further into the septum 210, the shield 6 is compressed in the vertical direction, and the outer circumferential wall 65 deforms such that its vertical dimension is reduced.

Figure 12:
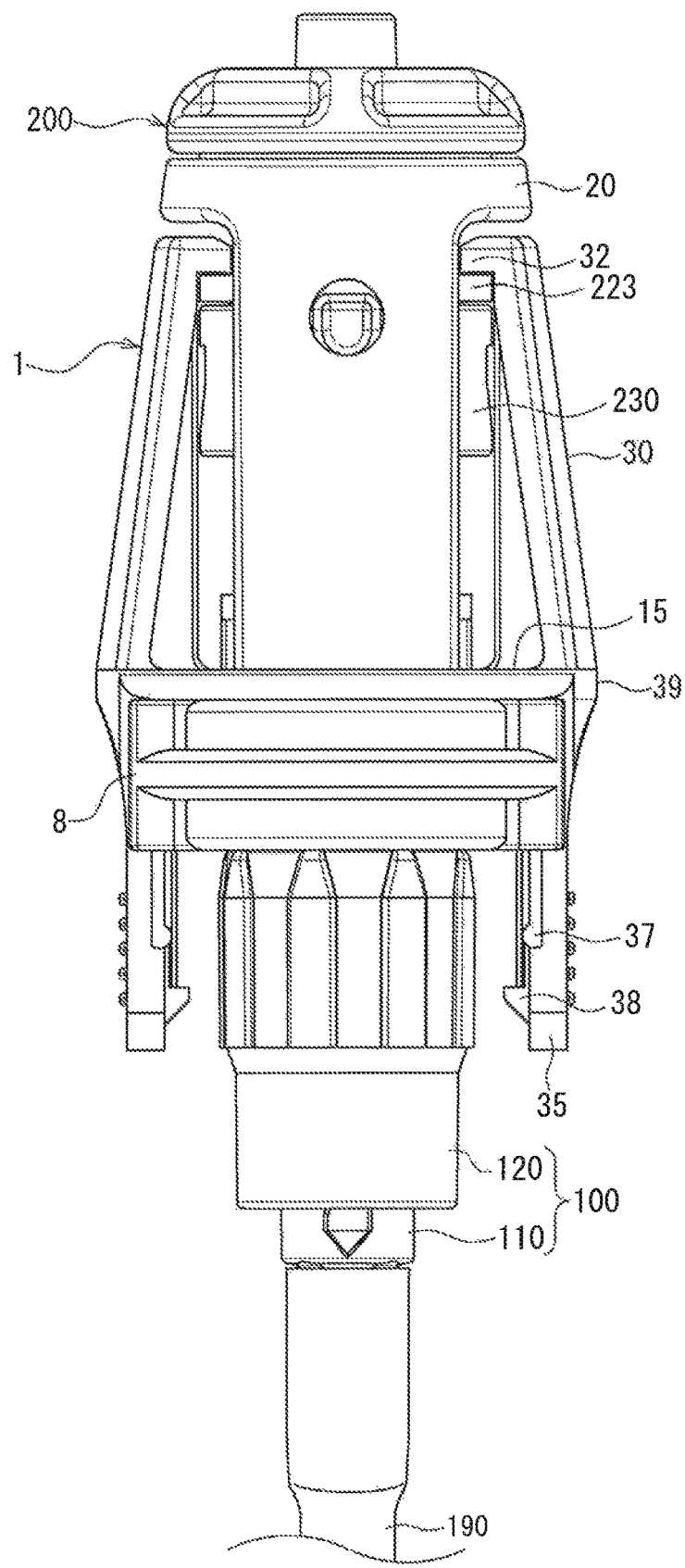
FIG. 12 is a perspective view of the male connector assembly according to the embodiment of the present invention in which locking claws of levers are engaged with the female connector and the lock ring is in the highest position.

The locking claws 32 of the levers 30 slide on the annular projection 223 after sliding on the peripheral wall 235 of the cap 230. When the locking claws 32 have passed the annular projection 223, the base 15 of the connector main body 3 elastically recovers, and the locking claws 32 are engaged with the annular projection 223 (locked state). FIG. 12 is a side view showing this state. The positions of the levers 30 and the lock ring 8 are the same as those in the initial state shown in FIGS. 5A and 9A.

Subsequently, the lock ring 8 is moved downward until it collides with the stopping projections 38 provided on the respective operating portions 35. The locking projections 37 are provided above the stopping projections 38, on the inner surfaces of the respective operating portions 35 (see FIG. 5B). In the process of moving the lock ring 8 downward, the bridging portions 88 move over the locking projections 37. When the bridging portions 88 move over the locking projections 37, the operator can feel a change in the force for moving the lock ring 8 as clicking sensation.

Figure 13A:
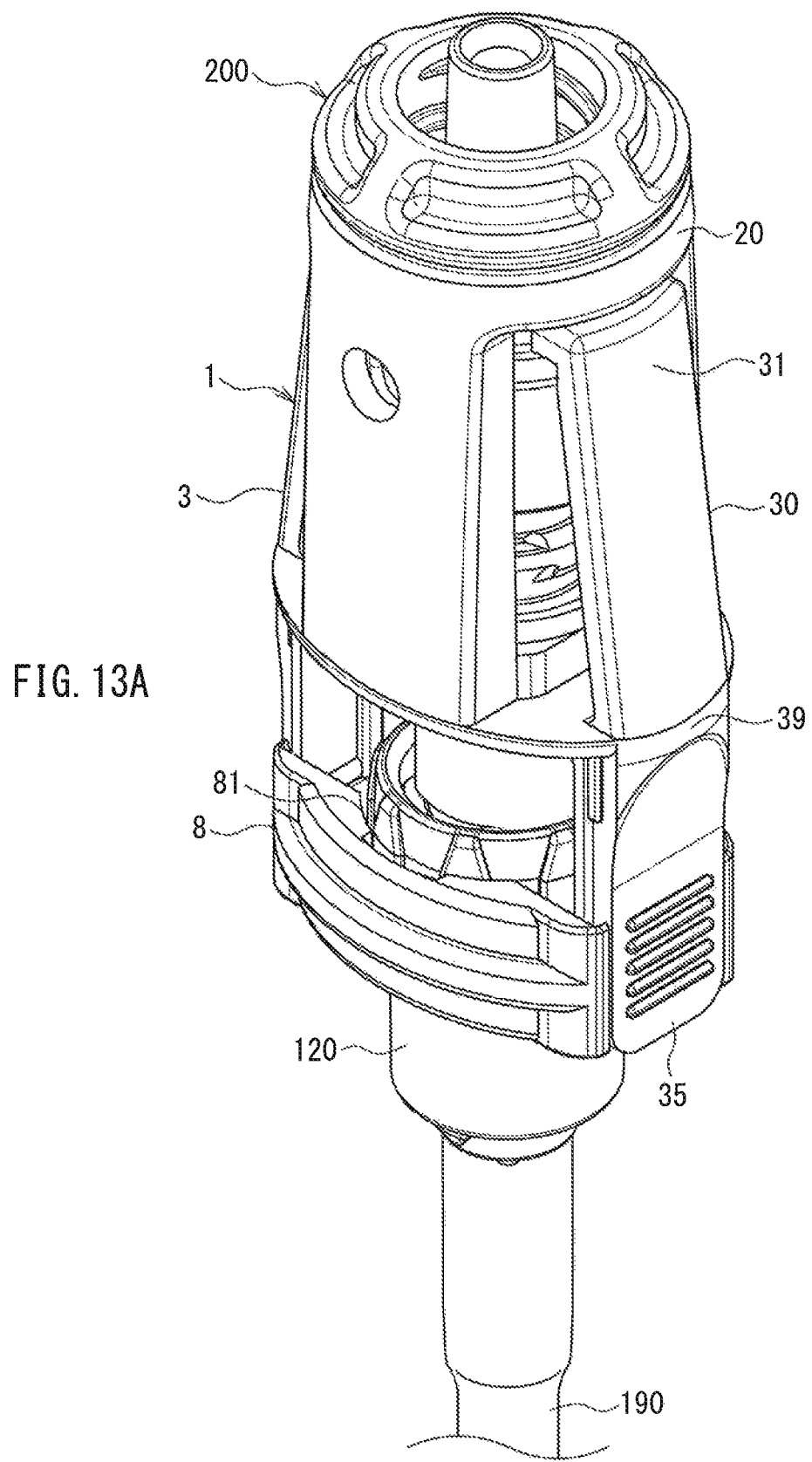
FIG. 13A is a perspective view of the male connector assembly according to the embodiment of the present invention after the connection to the female connector has been completed.
Figure 13B:
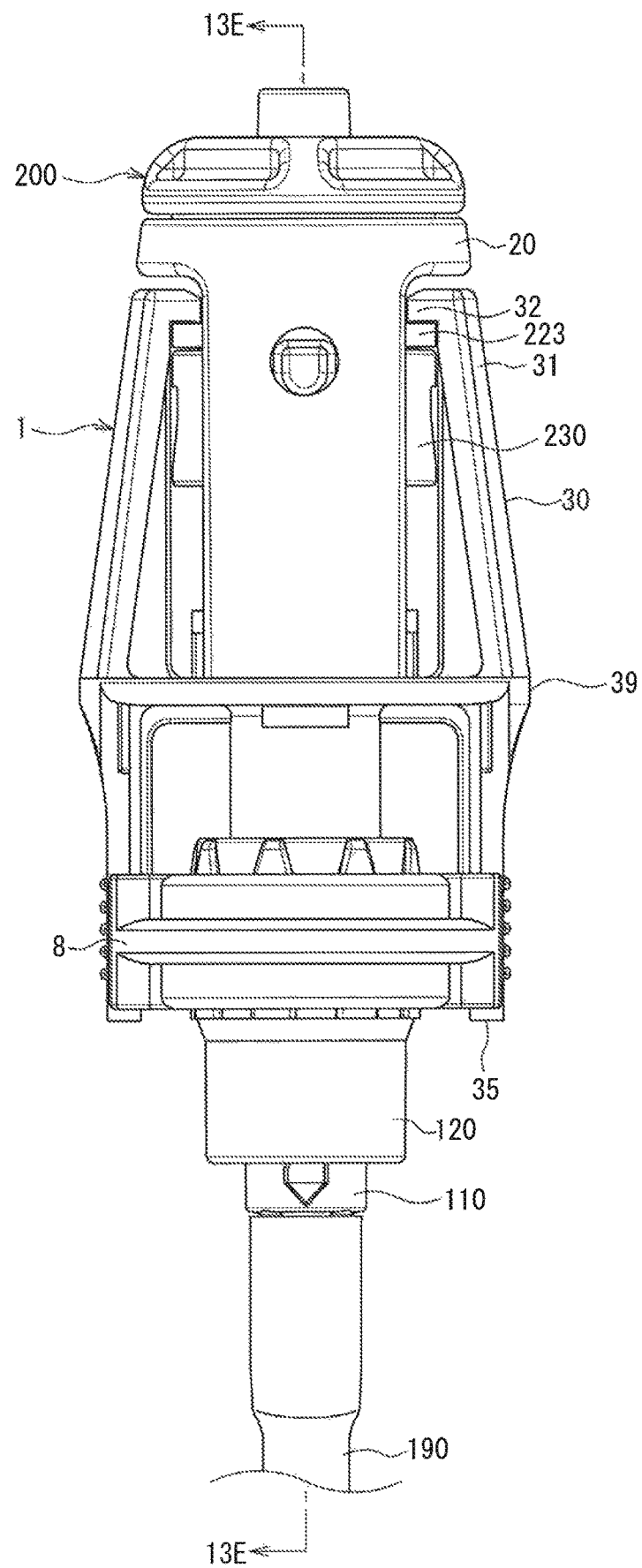
FIG. 13B is a front view of the male connector assembly in FIG. 13A.
Figure 13C:
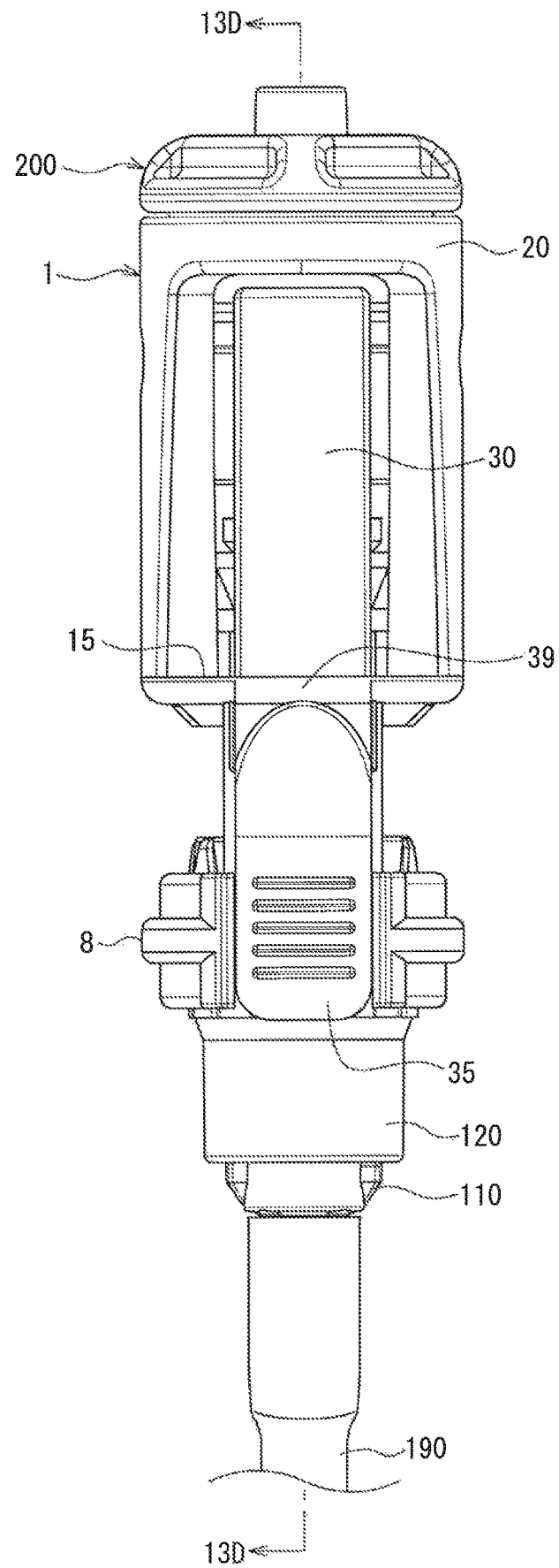
FIG. 13C is a side view of the male connector assembly in FIG. 13A.

FIGS. 13A, 13B, and 13C are a perspective view, a front view, and a side view, respectively, that show a state in which the lock ring 8 has been moved to its lowest position. FIG. 13D is a cross-sectional view taken along a plane containing line 13D-13D in FIG. 13C and seen in the direction of the arrows. FIG. 13E is a cross-sectional view taken along a plane containing line 13E-13E in FIG. 13B and seen in the direction of the arrows.

Figure 13D:
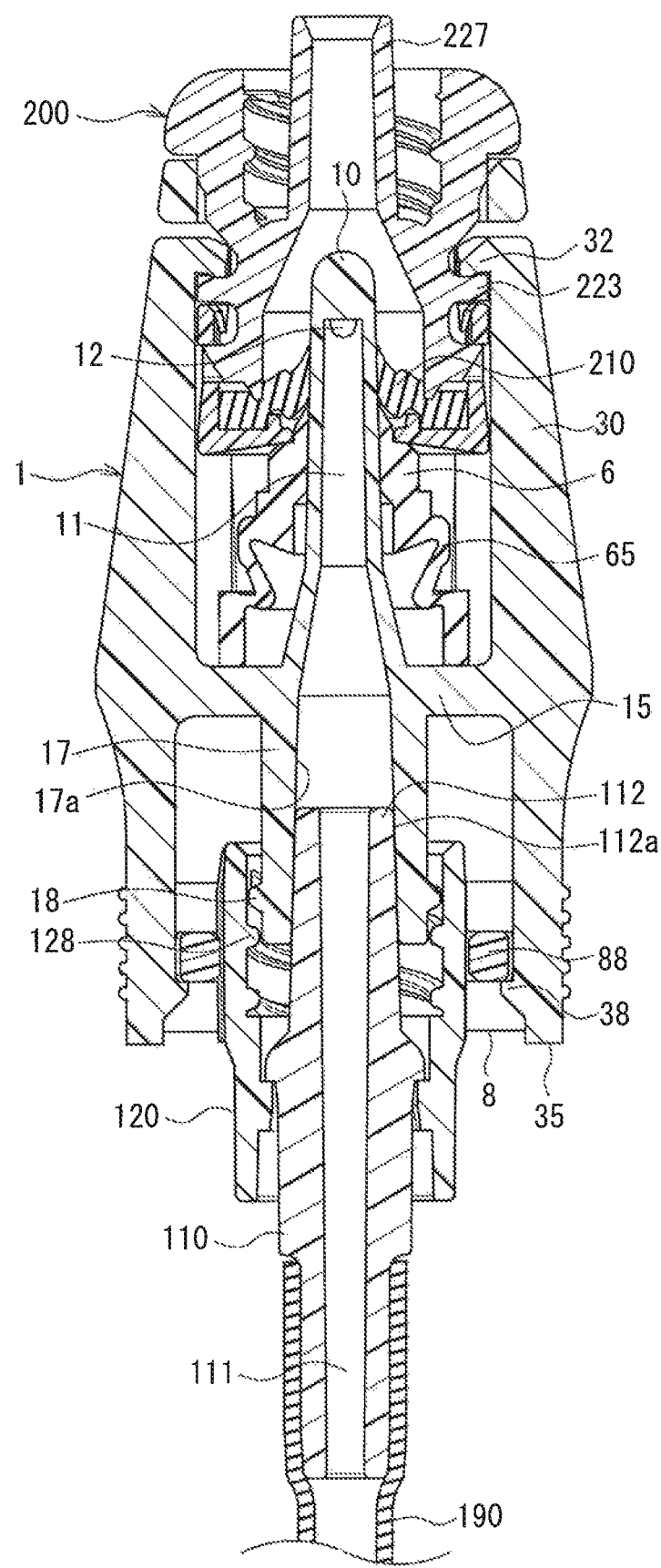
FIG. 13D is a cross-sectional view taken along a plane containing line 13D-13D in FIG. 13C and seen in the direction of the arrows.
Figure 13E:
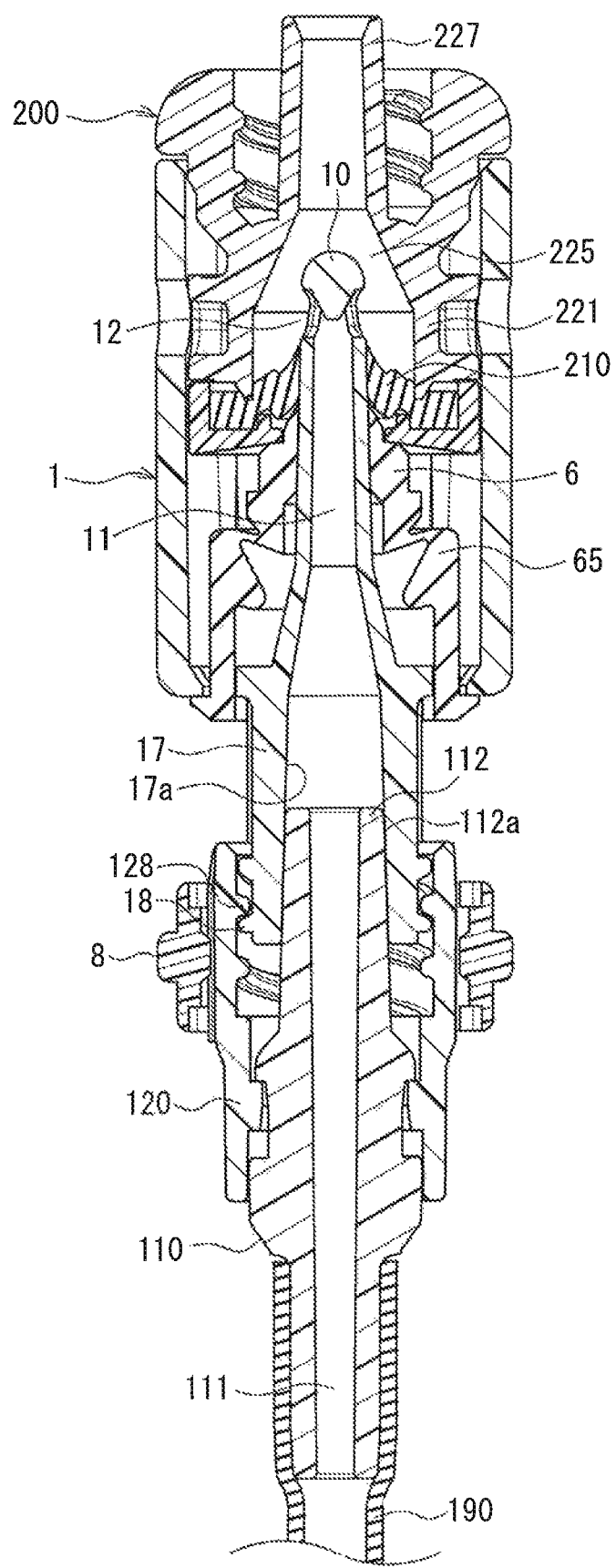
FIG. 13E is a cross-sectional view taken along a plane containing line 13E-13E in FIG. 13B and seen in the direction of the arrows.

As shown in FIG. 13E, the male luer 10 penetrates the slit 211 (see FIGS. 10A and 10B) of the septum 210, and thus, the septum 210 deforms toward the cavity 225 of the seat 221. The openings of the lateral holes 12 of the male luer 10 are exposed in the cavity 225 of the seat 221. Therefore, the flow channel 11 of the male luer 10 and the cavity 225 of the seat 221 are in communication with each other. In this state, a liquid is allowed to flow from the tube 190 to the flow channel 111 of the luer main body 110, the flow channel 11 of the male luer 10, the cavity 225 of the seat 221, and the male luer 227, or in the reverse direction.

The shield 6 receives the compressive force in the vertical direction. In particular, the outer circumferential wall 65 of the shield 6 deforms such that its vertical dimension is reduced.

As shown in FIGS. 13A and 13B, when the lock ring 8 is at its lowest position, an upper portion of the lock nut 120 is inserted into the opening 81 (see FIGS. 4A and 4B) of the lock ring 8. As described above, the plurality of ribs 83 protrude from the inner circumferential surface 82 of the opening 81 of the lock ring 8 (see FIG. 4A), while the plurality of ribs 123 protrude from the outer circumferential surface of the lock nut 120 (see FIG. 7A). Therefore, when the lock ring 8 is at its lowest position, each rib 123 of the lock nut 120 is fitted between two adjacent ribs 83 of the lock ring 8. Thus, the ribs 83 of the lock ring 8 are engaged with the ribs 123 of the lock nut 120. Also, as described above, the operating portions 35 and the ribs 36 of the connector main body 3 are fitted in the cut-outs 86 and the grooves 87 of the lock ring 8 (see FIG. 5B). Therefore, the lock nut 120 cannot be rotated relative to the connector main body 3. In this manner, the lock ring 8, when moved to its lowest position, functions as a "rotation prevention mechanism" that prevents the lock nut 120 from rotating.

Since the lock nut 120 cannot be rotated, an unforeseen situation resulting from loosening of the screwed connection between the female thread 128 of the lock nut 120 and the male thread 18 of the tubular portion 17, such as leakage of the liquid from between the outer circumferential surface 112a of the male luer 112 and the inner circumferential surface 17a of the tubular portion 17 or dislodgement of the male luer 112 from the tubular portion 17, does not occur As can be readily understood from FIG. 13D, when the lock ring 8 is at its lowest position, even if a force acting toward the tubular portion 17 is applied to the outer surfaces of the operating portions 35, the levers 30 cannot pivot because the inner surfaces of the operating portions 35 abut against the lock ring 8. That is to say, the lock ring 8, when moved to its lowest position, functions as a "lever pivotal movement prevention mechanism" that prevents the levers 30 from pivoting.

Since the levers 30 cannot pivot, the state (locked state) in which the locking claws 32 are engaged with the annular projection 223 cannot be cancelled. For this reason, an unforeseen situation in which the locking claws 32 are disengaged from the annular projection 223 by an unintentional external force acting on the operating portions 35, and the male connector assembly 1 (or the male connector 2) and the female connector 200 are disconnected from each other will not occur.

The lock ring 8 functions as both the "rotation prevention mechanism" that prevents the lock nut 120 from rotating and the "lever pivotal movement prevention mechanism" that prevents the levers 30 from pivoting. Thus, the number of members that constitute the male connector assembly 1 can be reduced, and the configuration of the male connector assembly 1 can be simplified.

When the lock ring 8 is at its highest position (first position, see FIG. 12), both of the mechanisms do not function, and if the lock ring 8 is moved to its lowest position (second position, see FIGS. 13A to 13E), both of the mechanisms function. In this manner, activation and deactivation of the rotation prevention mechanism and the lever pivotal movement prevention mechanism can be simultaneously switched through an extremely simple operation of moving a single member, the lock ring 8, along the central axis 3a.

As shown in FIG. 13D, when the lock ring 8 is at its lowest position, the stopping projections 38 abut against the bridging portions 88 of the lock ring 8. Therefore, the stopping projections 38 prevent the lock ring 8 from being dislodged downward from between the operating portions 35.

Although not shown in the drawings, when the lock ring 8 is at its lowest position, the locking projections 37 (see FIG. 5B) abut against the upper ends of the bridging portions 88. For this reason, the lock ring 8 is prevented from being unintentionally moved upward from the lowest position due to vibrations, an external force, and the like. That is to say, the locking projections 37 constitute a "second movement prevention mechanism" that prevents the lock ring 8 at its lowest position from being unintentionally moved upward. The lock ring 8 is held at its lowest position, and thus, the likelihood of the state in which the rotation prevention mechanism and the lever pivotal movement prevention mechanism are activated being unintentionally cancelled is reduced.

Briefly, the male connector assembly 1 and the female connector 200 can be disconnected from each other by performing the above-described procedures in reverse order.

That is to say, in the state shown in FIGS. 13A to 13E, the lock ring 8 is moved upward until it collides with the lower surface of the base 15, that is, until it reaches its highest position (first position, see FIG. 12). In the process of moving the lock ring 8 upward, it is necessary for the bridging portions 88 to move over the respective locking projections 37. As in the case of lowering the lock ring 8, the operator can feel a change in force when the bridging portions 88 move over the locking projections 37 as clicking sensation.

After the lock ring 8 has been moved to its highest position, an external force is applied to the outer surfaces of the operating portions 35 to cause the levers 30 to pivot, and thus, the locking claws 32 are disengaged from the annular projection 223. Subsequently, in the state in which the levers 30 have pivoted, the male connector assembly 1 and the female connector 200 are pulled apart from each other, and thus, the male connector assembly 1 and the female connector 200 can be disconnected from each other (see FIG. 11). The septum 210 elastically recovers immediately after the removal of the male luer 10, and thus, the slit 211 is closed. The shield 6 expands due to the elastic recovery force it has, and the inner circumferential surface of the head portion 62 closes the openings of the lateral holes 12 of the male luer 10. If the external force applied to the operating portions 35 is released, the levers 30 elastically return to the initial state.

Furthermore, if necessary, the female thread 128 and the male thread 18 may be unscrewed by rotating the lock nut 120, and then, the male connector 2 and the screw lock connector 100 may be disconnected from each other.

5. Effects

In the male connector assembly 1 of the present embodiment, the levers 30 including the locking claws 32 function as the "lever lock mechanism" for maintaining (locking) the state in which the male connector assembly 1 is connected to the female connector 200. In order to connect the male connector assembly 1 to the female connector 200, it is only necessary to insert the female connector 200 into the opening 21 of the hood 20 and push the female connector 200 further inward into the male connector assembly 1. Since the locking claws 32 are provided with the inclined surfaces 32a, when the female connector 200 is advanced into the hood 20, the levers 30 pivot. Afterward, when the female connector 200 has been inserted to a predetermined depth into the hood 20, the levers 30 return to their initial positions, and the locking claws 32 are engaged with the female connector 200. The engagement of the locking claws 32 with the female connector 200 (locked state) can be easily confirmed based on changes in the positions of the levers 30 (in particular, the locking portions 31) with respect to the radial direction, and furthermore, based on a "click" sound that is produced when the locking claws 32 are engaged with the female connector 200 and the levers 30 return to their initial positions. Since the end edge of the opening 21 of the hood 20 positions the female connector 200 with respect to the horizontal direction, a stable engagement operation can be performed at any time. The operator is not required to touch the levers 30 in order to engage the locking claws 32 with the female connector 200.

Moreover, the locking claws 32 can be disengaged from the female connector 200 simply by pressing the outer surfaces of the operating portions 35 to slightly pivot the levers 30.

As described above, the male connector assembly 1 of the present embodiment including the lever lock mechanism provides excellent ease of operations for connecting and disconnecting the male connector assembly 1 to and from the female connector 200.

The horizontal dimension of the connector main body 3 is largest in the direction in which the male luer 10 opposes the levers 30. More specifically, the outline (or projected shape of the connector main body 3) of the connector main body 3 when viewed from above is a substantially elliptical shape having the major axis 15a in the direction in which the male luer 10 opposes the levers 30 (FIG. 2E). The lock ring 8 also does not protrude outward from the above-described outline of the connector main body 3. A leading end portion (i.e., the cap 230) of the female connector 200 is housed in the hood 20. Therefore, if the male connector assembly 1 is pinned under a patient with the central axis 3a extending in the horizontal direction, the male connector assembly 1 can easily rotate so that the direction of the major axis 15a becomes the horizontal direction, and the likelihood of the weight of the patient acting on the male connector assembly 1 along the direction of the major axis 15a is low. Therefore, the likelihood of the weight of the patient acting on the operating portions 35 is low. Consequently, the likelihood of the state (locked state) in which the locking claws 32 of the levers 30 are engaged with the female connector 200 being unintentionally cancelled is low compared with that of a male connector provided with a conventional lever lock mechanism.

Furthermore, the operating portions 35 of the levers 30 are set back toward the central axis 3a from the lever base portions 39. Therefore, if the male connector assembly 1 is pinned under the patient, the likelihood of the weight of the patient being applied to the operating portions 35 of the levers 30 along the direction of the major axis 15a is even lower.

Moreover, an external force that is applied to the male connector assembly 1 when the male connector assembly 1 collides with a member thereabound or the male connector assembly 1 is pinned under the patient's body is highly likely to be applied to the lever base portions 39, which protrude furthest outward. The likelihood of the above-described external force being applied to the operating portions 35, which are set back toward the central axis 3a from the lever base portions 39, is low.

As described above, since the lever base portions 39 protrude furthest outward in the radial direction, and the operating portions 35 are located nearer to the central axis 3a than the lever base portions 39, the likelihood of the state (locked state) in which the locking claws 32 of the levers 30 are engaged with the female connector 200 being unintentionally cancelled is even lower.

Furthermore, when the lock ring 8 is moved to the lowest position, the levers 30 can no longer pivot even if a force is applied to the outer surfaces of the operating portions 35. Thus, the likelihood of the state (locked state) in which the locking claws 32 are engaged with the female connector 200 being unintentionally cancelled is yet even lower.

The lock ring 8 is disposed so as to abut against the inner surfaces of the operating portions 35. Thus, the lock ring 8 that does not protrude from the substantially elliptical outline of the connector main body 3 when viewed from above can be easily realized. If the male connector assembly 1 is pinned under the patient, this configuration is advantageous in rotating the male connector assembly 1 so that the direction of the major axis 15*a* becomes the horizontal direction. Also, if the male connector assembly 1 is pinned under the patient, this configuration is advantageous in reducing the patient's pain that is caused by the lock ring 8. Furthermore, this configuration is advantageous in simplifying the configuration of the lever pivotal movement prevention mechanism that prevents the levers 30 from pivoting and also improving the reliability of the operation of the lever pivotal movement prevention mechanism.

In the present embodiment, the leading end 20*a* of the hood 20 has a circular shape that is coaxial with the central axis 3*a*. The external diameter of the hood 20 at the leading end 20*a* of the hood 20 is approximately the same as the diameter (minor diameter) of the substantially elliptical outline of the connector main body 3 in the direction of the minor axis 15*b*. As described above, the external dimension of the hood 20 at the leading end 20*a* is set at the minimum dimension that is necessary for housing the female connector 200 and positioning the female connector 200 with respect to the horizontal direction. Thus, the size of the male connector assembly 1 (in particular, the connector main body 3) can be reduced. This is advantageous in reducing the patient's pain caused by the male connector assembly 1 if the male connector assembly 1 is pinned under the patient.

In the present embodiment, the portions of the male connector assembly 1 that protrude furthest from the central axis 3*a* in the radial direction are the lever base portions 39 (see FIG. 13B). The male connector assembly 1 has the largest horizontal dimension at the position of the lever base portions 39 (or the base 15). The locking portions 31 of the levers 30 are inclined such that the distance from the central axis 3*a* decreases as the distance from the lever base portions 39 increases. Thus, a smooth curved surface in which the outer surfaces of the locking portions 31 are continuous with the outer surface of the hood 20 can be formed in the male connector assembly 1 (in particular, the connector main body 3). This is advantageous in improving the design value of the male connector assembly 1. Also, this is advantageous in reducing the patient's pain caused by the male connector assembly 1 if the male connector assembly 1 is pinned under the patient.

The shield 6 is attached to the male luer 10. When the male connector assembly 1 is not connected to the female connector 200, the shield 6 closes the openings of the lateral holes 12 that are provided in the male luer 10 and that are in communication with the flow channel 11. Thus, when the male connector assembly 1 is not connected to the female connector 200, the liquid can be prevented from leaking to the outside through the lateral holes 12. Therefore, the shield 6 functions as a safety mechanism (fail-safe mechanism) that prevents the liquid from leaking even if all of the above-described various mechanisms that prevent unintentional cancellation of the connection between the male connector assembly 1 and the female connector 200 do not function.

6. Various Modifications

It should be understood that the foregoing embodiment is given by way of example only. The present invention is not limited to the foregoing embodiment, and modifications can be made thereto as appropriate.

The external shape of the male connector assembly 1 (in particular, the connector main body 3) is not limited to that of the foregoing embodiment.

Figure 14:
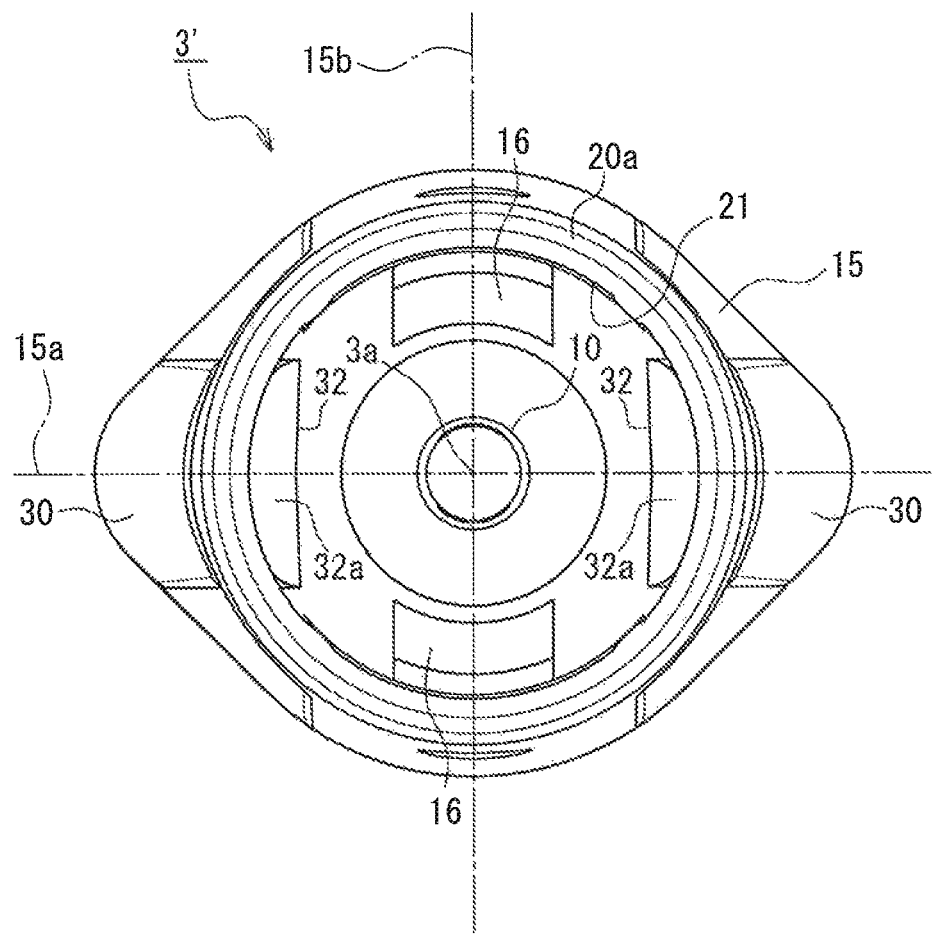
FIG. 14 is a plan view of a connector main body according to another embodiment of the present invention.
Figure 15:
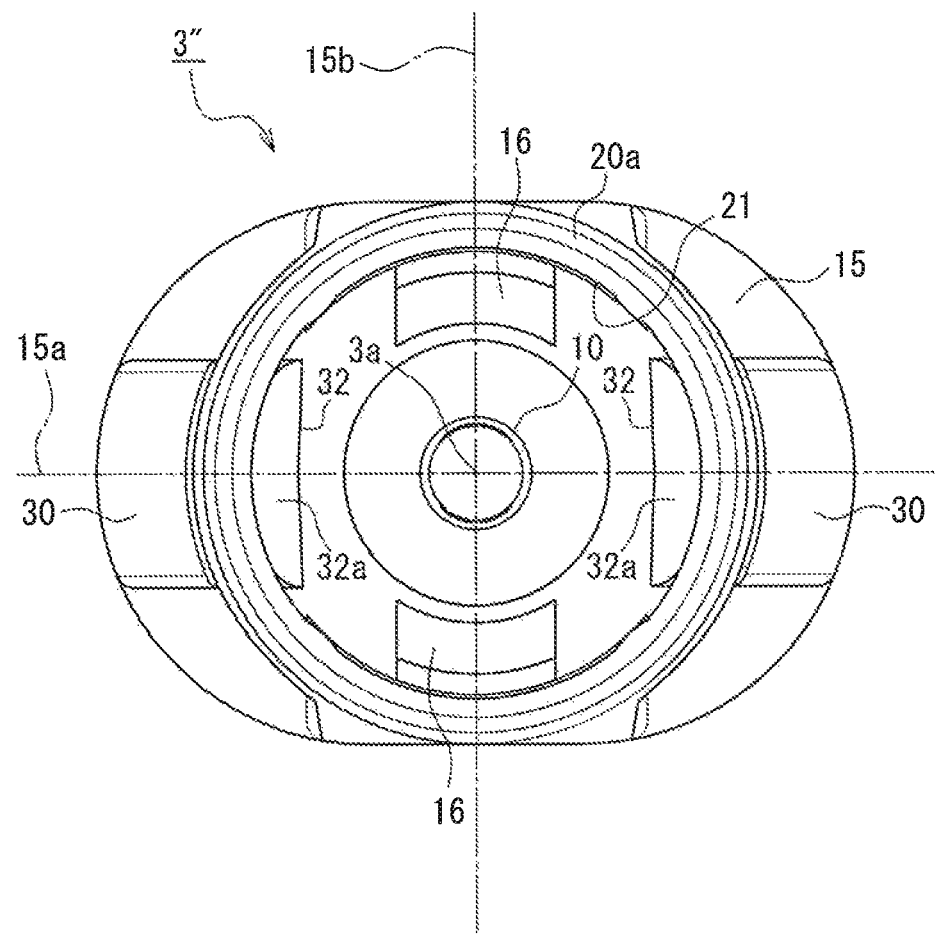
FIG. 15 is a plan view of a connector main body according to another embodiment of the present invention.

The outline (shape in plan view) of the connector main body 3 when the connector main body 3 is viewed along the central axis 3*a* is not required to be an exact ellipse. FIG. 14 is a plan view of a connector main body 3' having a substantially rhombic outline, and FIG. 15 is a plan view of a connector main body 3" whose outline has a shape (hereinafter referred to as "substantially track shape") that approximates the shape of a track of an athletic field. In FIGS. 14 and 15, members that correspond to the members shown in FIG. 2E are denoted by the same reference numerals as those in FIG. 2E. As is the case with the connector main body 3 shown in FIG. 2E, the outlines of the connector main bodies 3' and 3" are defined by the outline of the base 15. The outline of the connector main body 3' in FIG. 14 is not an exact rhombus, because the four corners of a rhombus that are located on the major axis 15*a* and the minor axis 15*b* are chamfered and rounded. The outline of the connector main body 3" in FIG. 15 is constituted by two semicircles that have the same radius and that oppose each other in the direction of the major axis 15*a*, and two straight lines that connect the two semicircles and that are parallel to the major axis 15*a*. The radius of the two semicircles and the length of the two straight lines can be set as desired. For this reason, the outline of the connector main body 3" in FIG. 15 may also be a shape that is not similar to the exact shape of a track of an athletic field.

Generally, an outline having a "substantially elliptical shape" in the present invention means that, when an axis (axis extending in the direction in which the male luer 10 opposes the levers 30) which is orthogonal to the central axis 3*a* and on which the external dimension is largest is taken as the major axis 15*a*, the horizontal dimension along the major axis 15*a* is larger than the horizontal dimension in a direction that is perpendicular to the major axis 15*a* (excluding the case where the two horizontal dimensions are equal to each other). Preferably, the "substantially elliptical shape" of the present invention is symmetrical with respect to the major axis 15*a*. Specifically, the "substantially elliptical shape" of the present invention includes, in addition to an exact ellipse (excluding circles), a substantially rhombic shape (see FIG. 14) and a substantially track shape (see FIG. 15). It can safely be said that the outline of the outline (see FIG. 2E) of the above-described connector main body 3 has the shape of an exact ellipse.

In the present invention, the male connector and the male connector assembly of the present invention can be configured in the same manner as those of the foregoing embodiment using the connector main body 3' (see FIG. 14), which has the substantially rhombic shape, the connector main body 3" (see FIG. 15), which has the substantially track shape, or even a connector main body whose outline has a substantially elliptical shape other than these shapes. As is the case with the foregoing embodiment, if such a male connector or a male connector assembly is pinned under the patient with the central axis 3*a* extending in the horizontal direction, the male connector or the male connector assembly can easily rotate so that the direction of the major axis 15*a* becomes the horizontal direction. Therefore, the above-described effect of the present invention that the likelihood of the state (locked state) in which the locking claws 32 of the levers 30 are engaged with the female connector 200 being unintentionally cancelled is low can be achieved. It is preferable that the shape of the lock ring 8 (the lever pivotal movement prevention mechanism and the rotation prevention mechanism) in plan view is changed as appropriate in accordance with the outline of the connector main body so that the lock ring 8 does not protrude outward from the outline of the connector main body when viewed along the central axis 3*a* of the connector main body.

In the foregoing embodiment, when viewed along the minor axis 15b, the shape of the portion of the connector main body 3 that is located above the base 15 is a tapered shape whose horizontal dimension decreases as the distance from the base 15 increases in the upward direction (see FIGS. 2C and 13B). However, the present invention is not limited to this, and for example, a rectangular shape having a constant horizontal dimension may also be possible. In this case, the locking portions 31 of the levers 30 extend parallel to the central axis 3a.

In the foregoing embodiment, when viewed along the major axis 15a, the portion of the connector main body 3 that is located above the base 15 has a substantially rectangular shape having a constant horizontal dimension (see FIGS. 2D and 13C). However, the present invention is not limited to this, and for example, a tapered shape whose horizontal dimension decreases as the distance from the base 15 increases in the upward direction may also be possible. That is to say, the external diameter of the hood 20 at the leading end 20a may be smaller than the diameter (minor diameter) of the connector main body 3 along the minor axis 15b (see FIG. 14).

In the foregoing embodiment, the outer surfaces of the operating portions 35 of the levers 30 are located nearer to the central axis 3a than the outer surfaces of the lever base portions 39 (see FIGS. 2C and 13B). However, the present invention is not limited to this. For example, when viewed along the minor axis 15b, the operating portions 35 may be located at the same positions as the lever base portions 39 with respect to the horizontal direction or may protrude outward compared with the lever base portions 39 in the horizontal direction. The further away the positions of the operating portions 35 from the central axis 3a in the horizontal direction, the higher the likelihood of an unintentional external force acting on the operating portions 35 and thereby causing cancellation of the state (locked state) in which the locking claws 32 are engaged with the female connector 200. However, the likelihood of the locked state being unintentionally cancelled can be reduced by increasing the rigidity of the base 15 that supports the levers 30, increasing the flattening of the substantially elliptical shape of the outline of the connector main body 3 when viewed along the central axis 3a, moving the lock ring 8 to its lowest position, and other methods.

In the foregoing embodiment, the levers 30 and the hood 20 are provided on the substantially elliptical base 15. However, the present invention is not limited to this. For example, a configuration may also be adopted in which the base 15 is divided into four segments by forming four cut-outs or four slits along the radial direction in the substantially elliptical base 15, and the levers 30 are supported by the two segments that are located along the major axis 15a and the hood 20 by the two segments that are located along the minor axis 15b. The four cut-outs or four slits may be advantageous in facilitating the pivotal movement of the levers 30 while securely coupling the hood 20 to the male luer 10.

Figure 16A:
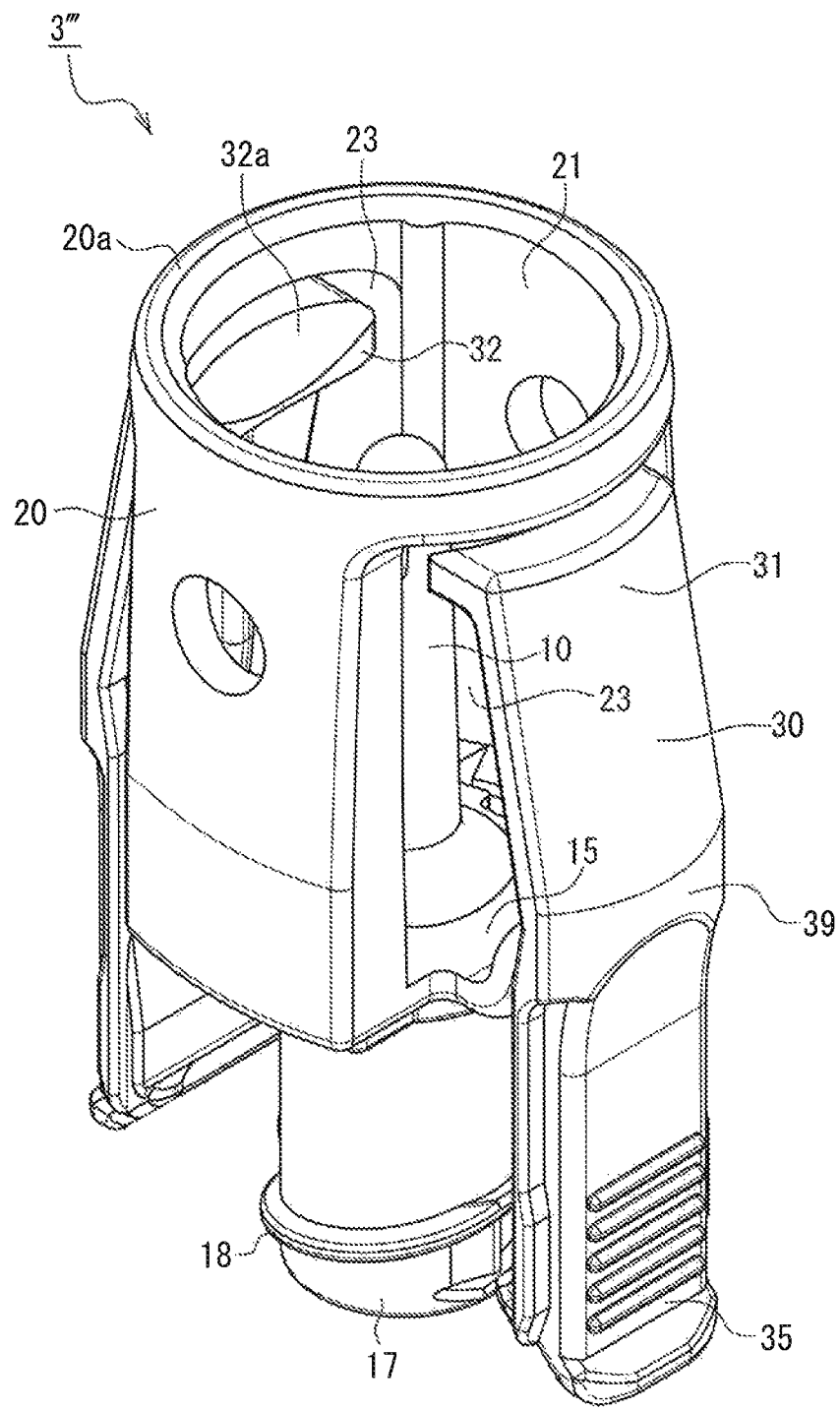
FIG. 16A is a perspective view of a connector main body according to yet another embodiment of the present invention when viewed from above.
Figure 16B:
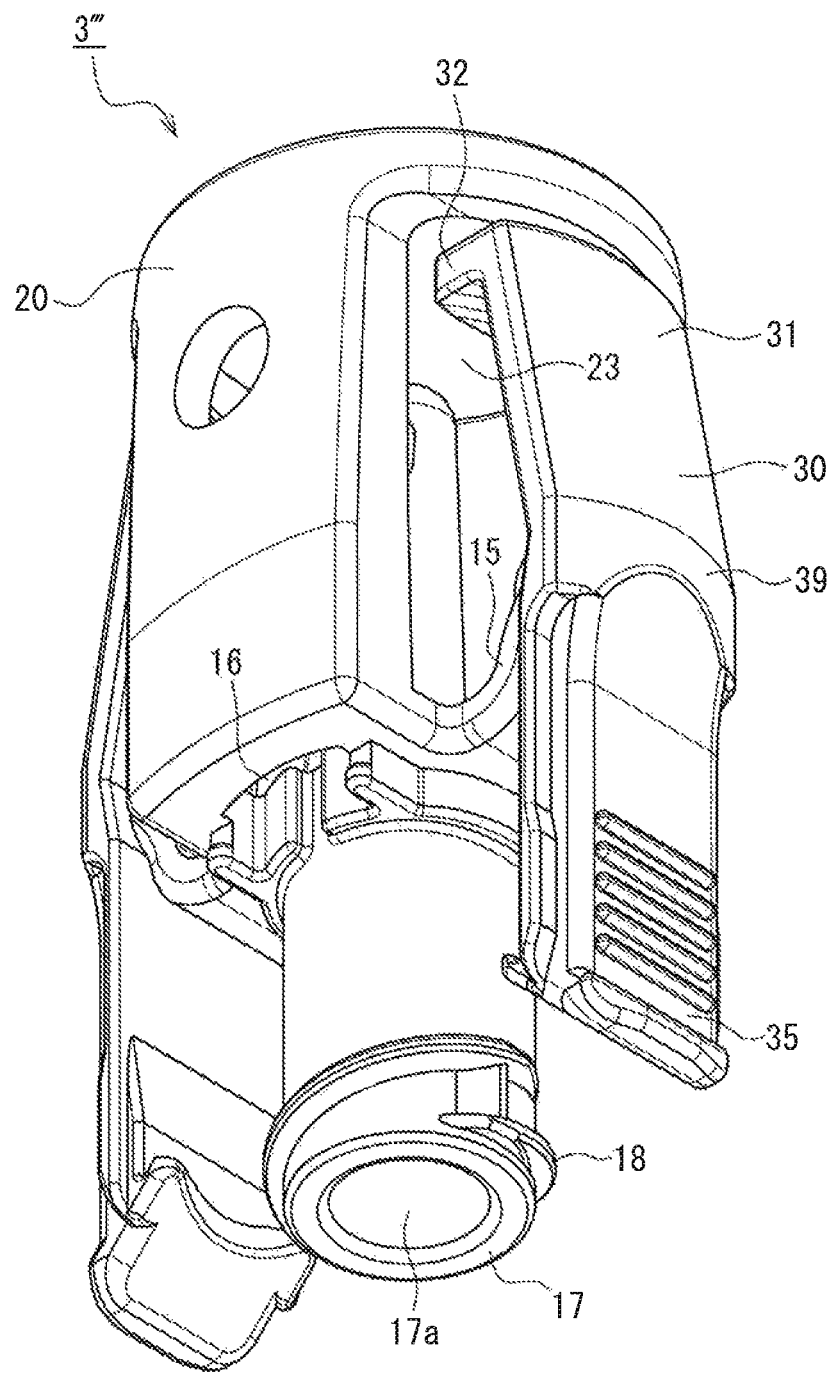
FIG. 16B is a perspective view of the connector main body shown in FIG. 16A when viewed from below.
Figure 16C:
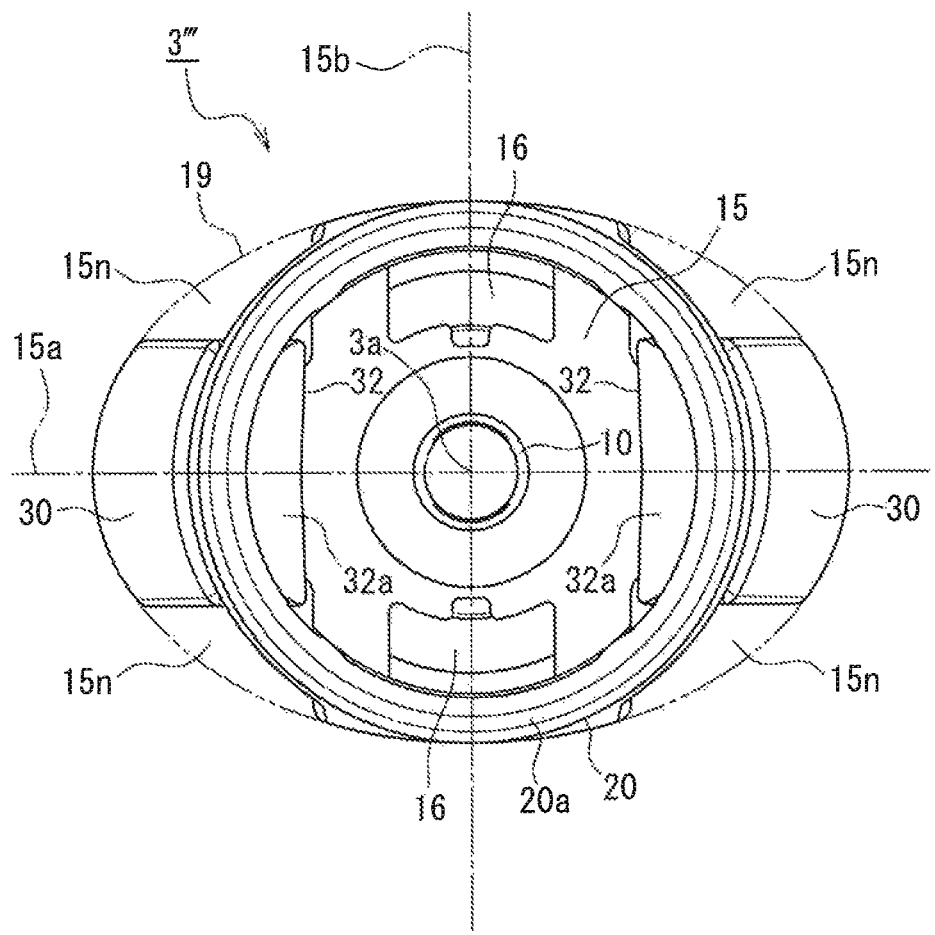
FIG. 16C is a plan view of the connector main body shown in FIG. 16A.

FIGS. 16A to 16C show an embodiment of this configuration. In FIGS. 16A to 16C, members that correspond to the members shown in FIGS. 2A to 2G are denoted by the same reference numerals as those in FIGS. 2A to 2G. As can be readily understood by comparing FIG. 16C with FIG. 2E, four cut-outs 15n are provided in the base 15 of a connector main body 3'''. The cut-outs 15n are provided in regions of the outer end edge of the base 15 excluding the portions (portions on the major axis 15a and the minor axis 15b) on which the levers 30 and the hood 20 are provided. When viewed from above along the central axis 3a (in plan view), the base 15 is substantially cross-shaped. The external dimension of the connector main body 3''' in plan view is largest in the direction (direction of the major axis 15a) in which the male luer 10 opposes the levers 30 and is smallest in the direction (direction of the minor axis 15b) that is orthogonal to this direction. The outline of the connector main body 3''' in plan view is recessed at the cut-outs 15n. The outline of the connector main body 3''' excluding the cut-outs 15n conforms to an ellipse 19 indicated by the long dashed double-short dashed line.

Figure 17A:
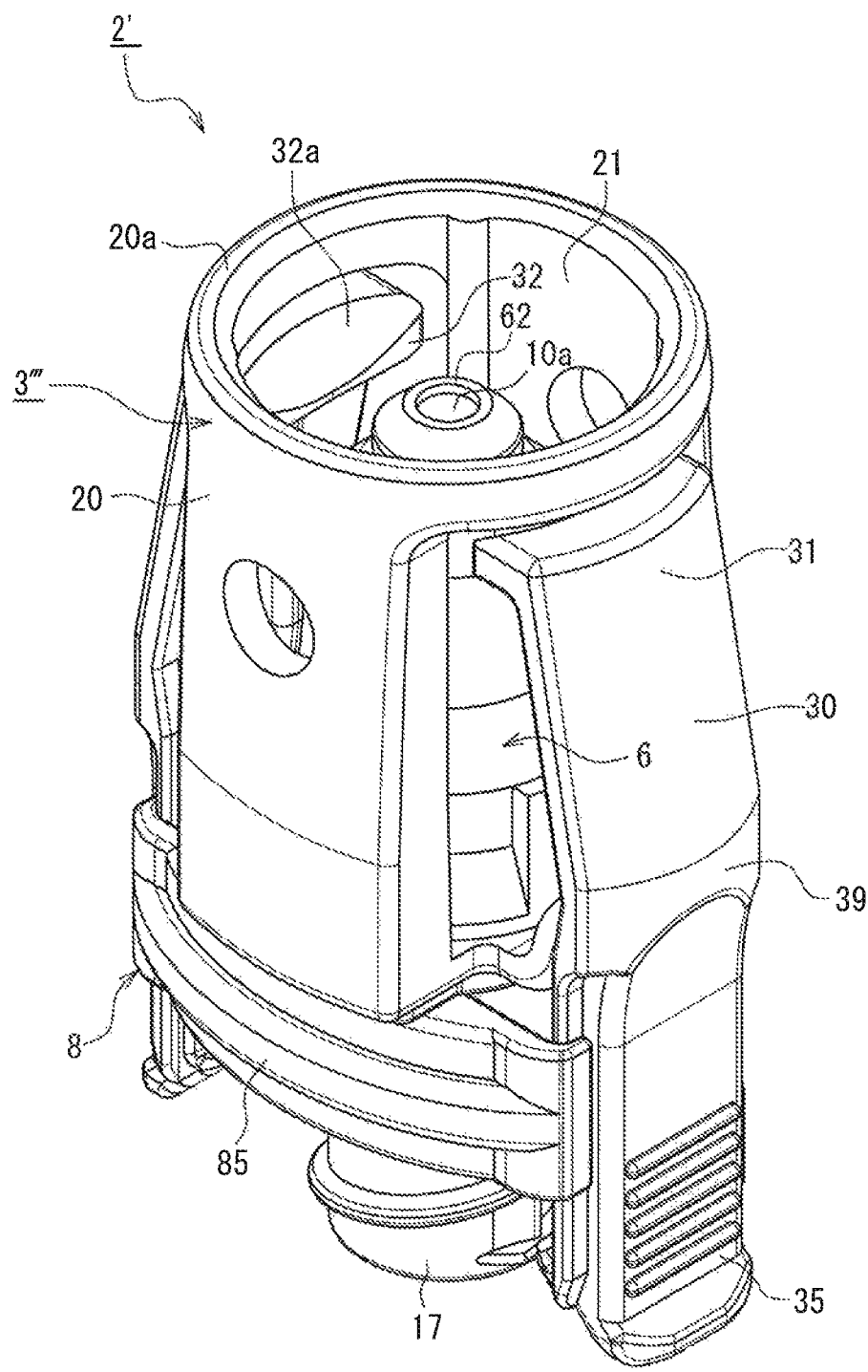
FIG. 17A is a perspective view of a lever lock male connector using the connector main body shown in FIGS. 16A to 16C.
Figure 17B:
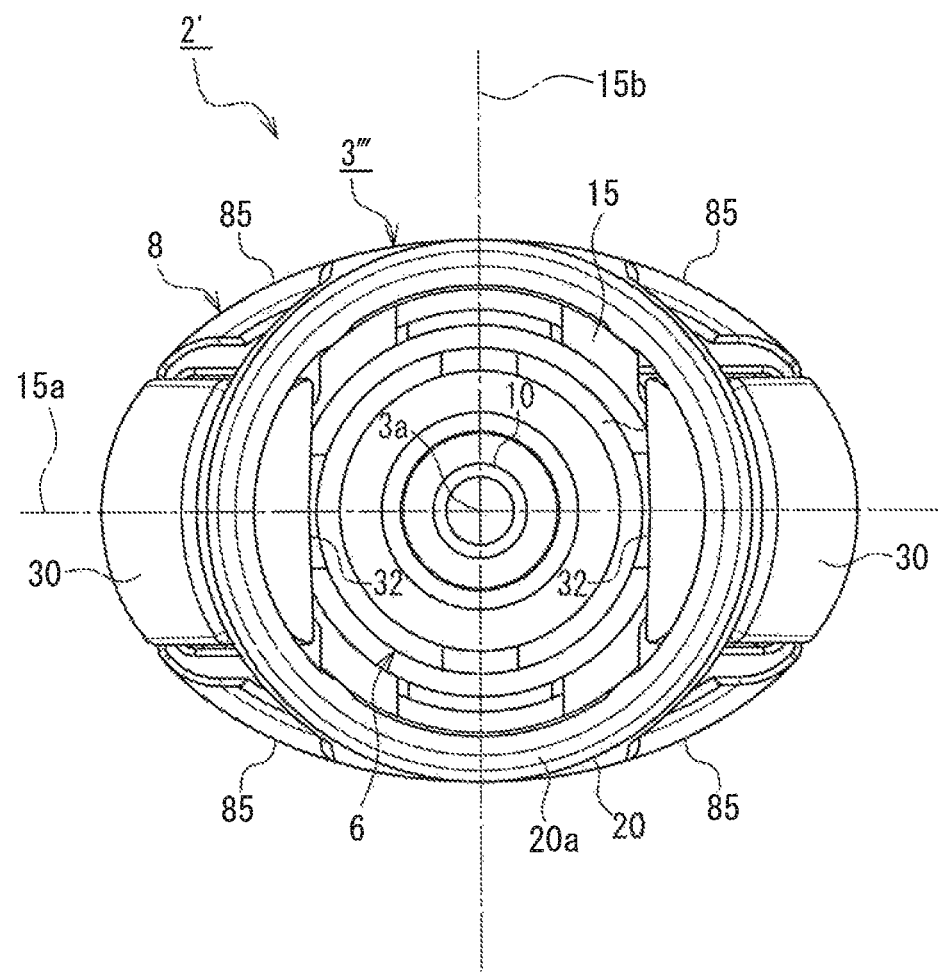
FIG. 17B is a plan view of the lever lock male connector shown in FIG. 17A.

A lever lock male connector 2' of the present invention can be configured by attaching the shield 6 (see FIGS. 3A to 3C) and the lock ring 8 (see FIGS. 4A and 4B) to the connector main body 3'''. FIG. 17A is a perspective view of the male connector 2', and FIG. 17B is a plan view of the male connector 2'. As described above, when the lock ring 8 is viewed from above (in plan view), the outer surfaces of the arch-shaped portions 85 of the lock ring 8 conform to an ellipse (see FIG. 4B). The ellipse to which the arch-shaped portions 85 conform coincides with the ellipse 19 shown in FIG. 16C. For this reason, as shown in FIG. 17B, when viewed from above along the central axis 3a (in plan view), the outline of the male connector 2' has an elliptical shape having the major axis 15a and the minor axis 15b. This elliptical outline is constituted by the connector main body 3''' and the lock ring 8. In this manner, even though the cut-outs 15n are provided in the outer end edge of the base 15 of the connector main body 3''', the outer surface of the lock ring 8 compensates for the cut-outs 15n, and thus, the male connector 2' having an elliptical outline in plan view can be realized. As is the case with the male connector 2 and the male connector assembly 1 that have been described above, if the male connector 2' or a male connector assembly using the male connector 2' is pinned under the patient with the central axis 3a extending in the horizontal direction, the male connector 2' or the male connector assembly can easily rotate so that the direction of the major axis 15a becomes the horizontal direction. Therefore, the likelihood of the state (locked state) in which the locking claws 32 of the levers 30 are engaged with the female connector 200 being unintentionally cancelled is low compared with that of a male connector including a conventional lever lock mechanism.

The cut-outs 15n as in the connector main body 3''' may also be provided in the base 15 of the connector main body 3' in FIG. 14. In this case as well, a male connector having a substantially rhombic outline in plan view can be realized by attaching a lock ring that can compensate for the cut-outs 15n to the connector main body 3'. The same holds true when the cut-outs 15n are provided in the base 15 of the connector main body 3'' in FIG. 15.

As described above, even when the shape of the outline of a connector main body alone is not substantially elliptical, a male connector having a substantially elliptical outline shape can be realized by attaching a lock ring to the connector main body. In the case where a substantially elliptical outline shape is configured by combining a connector main body with a lock ring as described above, the connector main body and the lock ring are not required to individually have a substantially elliptical outline shape. Thus, for example, it is possible to provide the cut-outs 15n in the base 15 of the connector main body 3''' (see FIGS. 16A to 16C) and to provide the cut-outs 86 in the lock ring (see FIGS. 4A and 4B), and therefore, the degree of freedom of design of the connector main body and the lock ring is improved As shown in FIGS. 16A and 16B, the base 15 of the connector main body 3''' is not a flat plate in the strict sense of the word. The base 15 has a stepped shape (or inclined shape) such that portions near the levers 30 are located higher than the portions near the male luer 10. This stepped shape (or inclined shape) increases the distance from the male luer 10 to each lever 30 along the surface of the base 15 without changing the external dimension of the connector main body in the direction of the major axis 15a. This configuration expands those regions of the base 15 that are capable of elastic bending deformation, and is therefore advantageous in facilitating the pivotal movement of the levers 30.

In the foregoing embodiment, the hood 20 is provided on the base 15 that connects the base end portion 13 of the male luer 10 and the levers 30. However, the method for connecting the hood 20 to the base end portion 13 is not limited to this. For example, the hood 20 may also be coupled to the male luer 10 via a member that is different from the base 15, which holds the levers 30. This configuration can also make it possible to facilitate the pivotal movement of the levers 30 while securely coupling the hood 20 to the male luer 10.

In the present invention, the number of levers 30 is not limited to two. For example, the male connector 2 may include only one lever 30. If the number of locking claws 32 is two or more, all of the locking claws 32 need to be simultaneously engaged with or disengaged from the female connector 200, and therefore, there is a possibility that the operations for connecting and disconnecting the male connector 2 to and from the female connector 200 may become complicated. If the number of levers 30 is only one, there is a possibility that the ease of the connecting and disconnecting operations may be improved.

In the foregoing embodiment, the locking claws 32 are engaged with the annular projection 223 of the female connector 200. However, the portion of the female connector 200 with which the locking claws 32 are engaged may be changed as appropriate in accordance with the configuration of the female connector 200. The shape and position of the locking claws 32 can be changed in accordance with the portions thereof that are to be engaged with the female connector 200.

The shape of the male luer 10 can be changed as desired. The number of lateral holes 12 that are in communication with the flow channel 11 is not necessarily required to be two, and may be one, or three or more. A configuration may also be adopted in which the lateral holes 12 are omitted, and the flow channel 11 is open into the leading end 10a of the male luer 10.

The configuration of the female connector to which the male connector assembly 1 is connected can be changed as desired. For example, the female connector may be a rubber stopper that seals an opening of a vial. A through hole like the slit 211 of the septum 210 is not formed in the rubber stopper in advance. Therefore, in this case, the male luer may be provided with a sharp leading end so as to be able to puncture the rubber stopper. Furthermore, in order to suppress fluctuations in air pressure within the vial when a liquid is flowing out of and into the vial, a liquid flow channel and a gas flow channel that are independent of each other may also be formed in the male luer. The levers (in particular, the locking claws 32) can be changed as appropriate so as to be engageable with the opening of the vial.

The configuration of the shield 6 can also be changed as desired. For example, the outer circumferential wall 65 may also have a bellows-like shape in which two tapered portions that are tapered in opposite directions are connected to each other. A configuration may also adopted in which a slit similar to the slit 211 of the septum 210 is provided in an upper surface of the head portion 61, and, in a state in which the male connector assembly 1 is not connected to a female connector, the upward opening of the through hole 62 is closed in a liquid-tight manner. The method for fixing the shield 6 to the base 15 is not limited to the method of locking the fixing claws 69a onto the base 15, and any methods such as adhesion, welding, fitting, and the like can be used.

In the present invention, the shield 6 may be omitted.

Also, the configuration of the lock ring 8 can be changed as desired. For example, the structure for preventing the lock nut 120 from rotating is not limited to the ribs 83 that are provided on the inner circumferential surface 82. For example, regular polygonal prism-shaped surfaces (e.g., regular octagonal prism-shaped surfaces) that can be fitted to each other may be provided on the inner circumferential surface of the lock ring 8 and the outer circumferential surface of the lock nut 120. Instead of fitting (engaging) the inner circumferential surface of the lock ring 8 and the outer circumferential surface of the lock nut 120 to (with) each other, shapes that can be fitted (including engagement) to each other when the lock ring 8 is moved downward may be provided on the lower surface of the lock ring 8 and the upper end surface of the lock nut 120.

The rotation prevention mechanism that prevents the lock nut 120 from rotating may be omitted. For example, either or both of the ribs 83 provided on the inner circumferential surface 82 of the lock ring 8 and the ribs 123 provided on the outer circumferential surface of the lock nut 120 may be omitted. When the rotation prevention mechanism is provided, a situation may occur in which it is difficult to move the lock nut 120 from its highest position (see FIG. 12) to its lowest position (see FIG. 13B) due to the ribs 83 and the ribs 123 colliding depending on the position of the lock nut 120 with respect to its rotating direction. A configuration in which the rotation prevention mechanism is omitted is advantageous in avoiding the occurrence of such a situation.

In the foregoing embodiment, the lock ring 8 at its highest position is prevented from being unintentionally moved downward by using the frictional force between the pressure contact ribs 35b of the operating portion 35 and the sliding ribs 85a of the lock ring 8. Moreover, in the foregoing embodiment, the lock ring 8 at its lowest position is prevented from being unintentionally moved upward by the locking projections 37, which protrude from the inner surfaces of the operating portions 35, being engaged with the lock ring 8. However, the mechanism (movement prevention mechanism) that prevents movement of the lock ring 8 is not limited to this. A mechanism that prevents movement of the lock ring 8 using a frictional force may also be applied to the lock ring 8 at its lowest position. Alternatively, a mechanism that is engageable with the lock ring may also be applied to the lock ring 8 at its highest position. Any protruding portion or recessed portion that can be fitted to or engaged with the lock ring 8, other than the mechanisms described in the foregoing embodiment, may also be provided on or in the operating portions 35. Alternatively, the movement prevention mechanism that prevents movement of the lock ring 8 at its highest position and/or the lowest position may be omitted.

In the present invention, the lock ring 8 may be omitted.

The tube 190 may also be connected directly to the tubular portion 17 of the male connector 2. For example, the tube 190 can be inserted into the tubular portion 17 and fixed through adhesion or the like. In this case, the screw lock connector 100 is no longer necessary. Moreover, the necessity for the lock ring 8 to function as the rotation prevention mechanism that prevents the lock nut 120 from rotating is eliminated, and therefore, the ribs 83 can be omitted.

INDUSTRIAL APPLICABILITY

While there is no particular limitation on the field of use of the present invention, the present invention can be extensively used in the field of medicine as a connecting device for forming a circuit (line) in order to convey various liquids such as a medicinal solution, an infusion solution, and blood. Furthermore, the present invention can also be used in various fields in which liquids are handled, such as the field of food other than medicine.

LIST OF REFERENCE NUMERALS

1 Male connector assembly
2, 2' Lever lock male connector
3, 3', 3", 3''' Connector main body
3a Central axis
6 Shield
8 Lock ring (lever pivotal movement prevention mechanism, rotation prevention mechanism)
10 Male luer
11 Flow channel of male luer
13 Base end portion of male luer
15 Base
15a Major axis
15b Minor axis
17 Tubular portion
17a Female tapered surface
18 Male thread
20 Hood
20a Leading end of hood
23 Cut-out
30 Lever
31 Locking portion
32 Locking claw
35 Operating portion
35b Pressure contact rib (first movement prevention mechanism)
37 Locking projection (second movement prevention mechanism)
39 Lever base portion
81 Opening of lock ring
100 Screw lock connector
110 Luer main body
112a Male tapered surface
120 Lock nut
128 Female thread
200 Female connector

The invention claimed is:

1. A lever lock male connector having a connector main body comprising a rod-shaped male luer, a tubular hood surrounding the male luer, and a lever connected to a base end portion of the male luer via a base, and a lever pivotal movement prevention mechanism,
wherein the male luer is disposed coaxially with a central axis of the connector main body,
the lever includes a locking portion that is disposed on a same side as the male luer relative to the base, an operating portion that is disposed on a side opposite to the male luer relative to the base, and a locking claw that protrudes toward the male luer from a surface of the locking portion that is located on a side facing the male luer,
the locking portion is disposed within a cut-out that is formed in the hood,
the lever is elastically pivotable so that, when an outer surface of the operating portion is pressed, the locking claw moves away from the male luer,
the lever pivotal movement prevention mechanism prevents the lever from pivoting such that the locking claw moves away from the male luer,
when the male connector is viewed along the central axis, the male connector has a major axis in a direction in which the male luer opposes the lever,
wherein the lever pivotal movement prevention mechanism is movable between a first position that is close to the base and a second position that is spaced apart from the base along the central axis of the connector main body, wherein further
when the lever pivotal movement prevention mechanism is at the first position, the lever is elastically pivotable so that the locking claw moves away from the male luer,
when the lever pivotal movement prevention mechanism is at the second position, the lever pivotal movement prevention mechanism prevents the lever from pivoting such that the locking claw moves away from the male luer, and
the lever pivotal movement prevention mechanism opposes the operating portion in a radial direction at both the first position and the second position.

2. The lever lock male connector according to claim 1, wherein the male connector has a substantially elliptical outline when viewed along the central axis.

3. The lever lock male connector according to claim 2, wherein the substantially elliptical outline is constituted by the connector main body and the lever pivotal movement prevention mechanism.

4. The lever lock male connector according to claim 2,
wherein a leading end of the hood has a circular shape that is coaxial with the central axis, and
an external diameter of the hood at the leading end is equal to or smaller than a minor diameter of the substantially elliptical shape along a minor axis that is perpendicular to the major axis.

5. The lever lock male connector according to claim 1, wherein the lever pivotal movement prevention mechanism is disposed so as to abut against an inner surface of the operating portion.

6. The lever lock male connector according to claim 1, comprising a first movement prevention mechanism that prevents the lever pivotal movement prevention mechanism at the first position from moving toward the second position or a second movement prevention mechanism that prevents the lever pivotal movement prevention mechanism at the second position from moving toward the first position.

7. The lever lock male connector according to claim 1, wherein the operating portion of the lever is located nearer to the central axis than a portion of the lever that is connected to the base.

8. The lever lock male connector according to claim 1, wherein a portion of the male connector that protrudes furthest from the central axis in the radial direction is a portion of the lever that is connected to the base.

9. The lever lock male connector according to claim 1,
wherein a flow channel through which a liquid flows is provided in the male luer,
an opening that is in communication with the flow channel is provided in an outer circumferential surface of the male luer, the male connector further includes a shield that closes the opening, and when the male luer is inserted into a female connector, the shield is compressively deformed in a longitudinal direction of the male luer, and the opening is exposed.

10. The lever lock male connector according to claim 1, the lever lock male connector comprising another lever, wherein the lever and the another lever are arranged at symmetrical positions with respect to the central axis.

11. A male connector assembly comprising the lever lock male connector according to claim 1 and a screw lock connector, wherein the connector main body further includes a tubular portion on the opposite side to the male luer relative to the base, the tubular portion being in communication with the male luer, a female tapered surface is formed on an inner circumferential surface of the tubular portion, the female tapered surface having an internal diameter that increases as the distance to a leading end of the tubular portion decreases, a male thread is formed on an outer circumferential surface of the tubular portion, the screw lock connector includes a luer main body provided with a male tapered surface that is fitted to the female tapered surface of the tubular portion and a lock nut that is rotatable around the luer main body, and the lock nut is provided with a female thread that is screwed onto the male thread of the tubular portion.

12. The male connector assembly according to claim 11, further comprising a rotation prevention mechanism that prevents the lock nut from rotating in a state in which the male tapered surface of the luer main body has been fitted to the female tapered surface of the tubular portion and the female thread of the lock nut has been screwed onto the male thread of the tubular portion.

13. The male connector assembly according to claim 12, wherein the rotation prevention mechanism also functions as the lever pivotal movement prevention mechanism that prevents the lever from pivoting such that the locking claw moves away from the male luer.

14. The male connector assembly according to claim 12, wherein the rotation prevention mechanism has an annular shape with an opening formed at a center thereof, and the tubular portion or the luer main body is disposed in the opening of the rotation prevention mechanism.

* * * * *